(12) United States Patent
Okano et al.

(10) Patent No.: US 11,993,650 B2
(45) Date of Patent: May 28, 2024

(54) PHARMACEUTICAL COMPOSITION FOR TREATMENT AND PREVENTION OF CANCER

(71) Applicant: TORAY INDUSTRIES, INC., Tokyo (JP)

(72) Inventors: Fumiyoshi Okano, Kanagawa (JP); Takanori Saito, Kanagawa (JP); Takayoshi Ido, Kanagawa (JP); Masaki Shimizu, Ehime (JP)

(73) Assignee: Toray Industries, Inc., Tokyo (JP)

( * ) Notice: Subject to any disclaimer, the term of this patent is extended or adjusted under 35 U.S.C. 154(b) by 330 days.

(21) Appl. No.: 16/800,852

(22) Filed: Feb. 25, 2020

(65) Prior Publication Data

US 2020/0247888 A1 Aug. 6, 2020

Related U.S. Application Data

(62) Division of application No. 13/002,636, filed as application No. PCT/JP2009/062573 on Jul. 10, 2009, now Pat. No. 10,611,835.

(30) Foreign Application Priority Data

Jul. 10, 2008 (JP) ............................... 2008-180057
Mar. 31, 2009 (JP) ............................... 2009-087379

(51) Int. Cl.
*A61K 39/00* (2006.01)
*C07K 16/28* (2006.01)
*C07K 16/30* (2006.01)
*A61K 39/395* (2006.01)

(52) U.S. Cl.
CPC ...... *C07K 16/2803* (2013.01); *C07K 16/3015* (2013.01); *C07K 16/3061* (2013.01); *A61K 39/39558* (2013.01); *A61K 2039/505* (2013.01); *C07K 2317/732* (2013.01); *C07K 2317/734* (2013.01)

(58) Field of Classification Search
CPC .............................................. A61K 2039/505
See application file for complete search history.

(56) References Cited

U.S. PATENT DOCUMENTS

| 5,595,756 A | 1/1997 | Bally et al. |
| 8,227,455 B2 | 7/2012 | Masuda et al. |
| 2011/0130343 A1 | 6/2011 | Okano et al. |
| 2012/0100162 A1* | 4/2012 | Brodsky ............ A61K 31/664 424/184.1 |

FOREIGN PATENT DOCUMENTS

| EP | 0419858 A1 | 4/1991 | |
| EP | 1001020 A1 | 5/2000 | |
| JP | 10-513348 | 12/1998 | |
| JP | 2006-014637 | 1/2006 | |
| JP | 2007-53501 | 12/2007 | |
| WO | WO-96/023071 | 12/1998 | |
| WO | WO-200177332 A2 | 10/2001 | |
| WO | WO-2003060080 A2 | 7/2003 | |
| WO | WO-2004024750 A2 | 3/2004 | |
| WO | WO-2004048938 A2 | 6/2004 | |
| WO | WO-2005083074 A1 | 9/2005 | |
| WO | WO-2005118869 A2 | 12/2005 | |
| WO | WO-06/117910 | 11/2006 | |
| WO | WO-07/128231 | 11/2007 | |
| WO | WO-05/000901 | 12/2007 | |
| WO | WO-07/143098 | 12/2007 | |
| WO | WO-08/034076 | 3/2008 | |
| WO | WO-2008034074 A2 * | 3/2008 | ........... A61K 31/664 |
| WO | WO-2008034076 A2 * | 3/2008 | ........... A61K 31/664 |
| WO | WO-2008141197 A1 | 11/2008 | |

OTHER PUBLICATIONS

Kiyokawa et al. (Mod. Pathol. Apr. 2004; 17 (4): 423-9).*
Hammer (MAbs. Sep.-Oct. 2012; 4 (5): 571-7).*
Clark et al. (Ann. Rheum. Dis. Nov. 2005; 64; Suppl. 4: iv77-80; pp. 1-4).*
Adams, et al., "Monoclonal Antibody Therapy of Cancer", Nature Biotechnology, 23(9): 1147-1157, Sep. 2005, 11 pages.
Albanesi et al., "Neutrophils mediate antibody-induced antitumor effects in mice," Blood, vol. 122, No. 18, pp. 3160-3164, Oct. 2013, Supplemental Data.
Albanesi et al., "Neutrophils mediate antibody-induced antitumor effects in mice," Blood, vol. 122, No. 18, pp. 3160-3164, Oct. 2013.
Auerbach, et al., "Angiogenesis Assays: Problems and Pitfalls," Cancer and Metastasis Reviews, 19:167-172, Jun. 2000, 6 pages.
Berendsen, "A Glimpse of the Holy Grail?", Science, pp. 642-643, Oct. 23, 1998, 2 pages.
Bradley, et al., "Limits of Cooperativity in a Structurally Modular Protein: Response of the Notch Ankyrin Domain to Analogous Alanine Substitutions in Each Repeat", Journal Mol. Biol., 324:373-386, Nov. 2002, 14 pages.
Chiaretti et al., "Diagnosis and Subclassification of Acute Lymphoblastic Leukemia," Mediterranean Journal of Hematology and Infectious Diseases, Nov. 1, 2014, vol. 6, No. 1. 14 pages.
Cooper, et al., "Production of Antibodies", Current Protocols in Immunology, Supplement 13, pp. 2.4.1-2.4.9, No Month Listed 1995, 9 pages.
Definition of "Prophylaxis", Dictionary.Com, accessed Aug. 9, 2012, 3 pages.

(Continued)

*Primary Examiner* — Stephen L Rawlings
(74) *Attorney, Agent, or Firm* — Wilmer Cutler Pickering Hale and Dorr LLP

(57) ABSTRACT

An antibody or a fragment thereof having immunoreactivity to a polypeptide comprising not less than 7 continuous amino acids in the CD179b protein, which was identified as a cancer antigen protein specifically expressed on the surfaces of cancer cells, can be used as a pharmaceutical composition for therapy and/or prophylaxis of cancer.

5 Claims, 2 Drawing Sheets

Specification includes a Sequence Listing.

(56) References Cited

OTHER PUBLICATIONS

Designing Custom Peptides, SIGMA Genosys Website, www.sigma-genosys.com/peptide_design.asp, accessed Dec. 16, 2004, 2 pages.
European Search Report issued in European Patent Application No. 09794513.3, dated Oct. 9, 2012, 8 pages.
Favaro et al., "FMNL1 promotes proliferation and migration of leukemia cells," Journal of Leukocyte Biology, vol. 94, No. 3, pp. 503-512, Sep. 2013.
Hollis et al., "Immunoglobulin a light-chain-related genes 14.1 and 16.1 are expressed in pre-B cells and may encode the human immunoglobulin omega light-chain protein," Proc. Natl. Acad. Sci. USA, Jul. 1989, vol. 86, pp. 5552-5556.
Human CD176b Amino Acid Sequence-P15814, www.uniprot.org/uniprot/P15814, accessed Dec. 1, 2013, 9 pages.
Hussain et al., "Lymphoblastoid Cell lines: a Continuous in Vitro Source of Cells to Study Carcinogen Sensitivity and DNA Repair", Int. J. Mol. Cell. Med. vol. 1, No. 2, pp. 75-87, Spring 2012.
Hystad et al., "Characterization of Early States of Human B Cell Development by Gene Expression Profiling", The Journal of Immunology, Sep. 15, 2015, vol. 179, No. 6, pp. 3662-3671.
Imamura et al., "A novel infant acute lymphoblastic leukemia cell line with MLL-AF5q31 fusion transcript," Leukemia, vol. 16, No. 11, pp. 2302-2308, Nov. 2002.
International Search Report issued in PCT/JP2009/062574, dated Aug. 25, 2009, 5 pages.
Jain, "Barriers to Drug Delivery in Solid Tumors", Scientific American, pp. 58-65, Jul. 1994, 9 pages.
Jeschkeit, et al., "Amino Acids, Peptides, Proteins", Mir, pp. 366-374, original German language publication 1981, Russian language translation 1985, No Month Listed. 24 pages.
Karasuyama et al., "Surrogate Light Chain in B Cell Development," Advances in Immunology, (1996), vol. 63. 41 pages.
Kharbanda et al., "BDCM: a novel B-cell line with genetic functional similarity to dendritic cells," British Journal of Haematology, Dec. 2002, vol. 119, issue 3, pp. 819-825.
Kiyokawa et al., "Diagnostic importance of CD179a/b as markers of precursor B-cell lymphoblastic lymphoma," Mod Pathol., vol. 17, pp. 423-429 (2004).
Kiyokawa, "Usability of CD176a/b as Diagnostic Markers for Precursor B Cell Lymphoblastic Lymphoma", Nippon Byorai Gakkai Kaishi, vol. 93, p. 413, No Month Listed, 2004, 2 pages.
LeBien, T. "Fates of human B-cell precursors", Blood, Jul. 1, 2000, vol. 96, No. 1, pp. 9-23.
Lemmers et al., "Fine characterization of childhood and adult acute lymphoblastic leukemia (ALL) by a proB and preB surrogate light chain-specific m-AB and proposal for a new B cell ALL classification," Leukemia, Dec. 2000, vol. 14, No. 12, pp. 2103-2111.
Leukemia, B-Cell: MeSH Descriptor Data 2017, NIH U.S. National Library of Medicine, 8 pages, retrieved from: https://meshb.nlm.nih.gov/record/ui?ui=D015448. [First reviewed Apr. 13, 2017].
Merck Manual, "Cellular and Molecular Basis of Cancer", 2008, accessed Nov. 7, 2012, 5 pages.
Merck Manual, "Clinical Aspects of Cancer", Accessed Mar. 5, 2008, 4 pages.
Merck Manual, "Introduction: Overview of Cancer", Accessed Mar. 5, 2008, 1 page.
Mufson, "Tumor Antigen Targets and Tumor Immunotherapy", Frontiers in Bioscience, 11:337-343, Jan. 1, 2006, 7 pages.
Murohashi et al., "Gene Profiling Mechanisms of Cell Density-Dependent Growth in Myeloid and Lymphoid Leukemia Cell Lines," Blood Journal, vol. 114, Issue 22, Abstract 4420, (2009).
Namalwa (ATCC® CRL-1432™), ATCC.org, Product pages, 18 pages, retrieved from: https://www.atcc.org/Products/All/CRL-1432.aspx#generalinformation. [First reviewed Oct. 17, 2016].
Neidle, "Cancer Drug Design and Discovery", Elsevier/Academic Press, pp. 427-431, No Month Listed 2008, 5 pages.
Ngo, "Computational Complexity, Protein Structure Prediction, and the Levinthal Paradox", The Protein Folding Problem and Tertiary Structure Prediction, pp. 491-494, 1994, 4 pages.
Oka, et al., "Induction of WT1 (Wilms' tumor gene)-Specific Cytotoxic T Lymphocytes by WT1 Peptide Vaccine and the Resultant Cancer Regression", PNAS, 101(38):13885-13890, Sep. 21, 2004, 6 pages.
Presta, et al., "Engineering Therapeutic Antibodies for Improved Function", Biochemical Society Transactions, 30(4):487-490, Aug. 2002, 4 pages.
PubMed Publication on Amino Acid Mutation in Protein in 2009, accessed Jul. 12, 2013, 3 pages.
Rudinger, "Characteristics of the Amino Acids as Components of a Peptide Hormone Sequence", Chapter 1 in Peptide Hormones, Parsons, Ed., pp. 1-7, No Month Listed 1976, 8 pages.
Schirle, et al., "Combining Computer Algorithms with Experimental Approaches Permits the Rapid and Accurate Identification of T Cell Epitopes from Defined Antigens", Journal of Immunological Methods, 257:1-16, Nov. 2001, 16 pages.
Sporn et al., "Chemoprevention of Cancer." Carcinogenesis. Vol. 21, No. 3, No Month Listed 2000, pp. 525-530. 6 pages.
Tsuganezawa et al., "Flow Cytometric Diagnosis of the Cell Lineage and Developmental State of Acute Lymphoblastic Leukemia by Novel Monoclonal Antibodies Specific to Human Pre-B-Cell Receptor," Blood, Dec. 1, 1998, vol. 92, No. 11, pp. 4317-4324.
Van'tVeer, et al., "Gene Expression Profiling Predicts Clinical Outcome of Breast Cancer", Nature, 415:530-530, Jan. 31, 2002,7 pages.
Voet, et al., Biochemistry: Second Edition, John Wiley & Sons, Inc., pp. 235-241, No Month Listed, 1995, 9 pages.
Wang et al., "Differential surrogate light chain expression governs B-cell differentiation," Blood, Apr. 1, 2002, vol. 99, No. 7, pp. 2459-2467.
Zhu, et al., "Toll like receptor-3 ligand poly-ICLC promotes the efficacy of peripheral vaccinations with tumor antigen-derived peptide epitopes in murine CNS tumor models", Journal of Translational Medicine, Feb. 12, 2007, 15 pages.
Chintalacharuvu et al., "Chimeric Antibodies: Production and Applications," Methods: A companion to Methods in Enzymology, Oct. 1995, vol. 8, pp. 73-82.
Uike et al., "Phase I Study of KW-0761, a Humanized Anti-CCR4 Antibody, in Patients (Pts) with Relapsed or Refractory Adult T-Cell Leukemia-Lymphoma (ATLL) and Peripheral T-Cell Lymphoma (PTCL): Preliminary Results," Abstract, Blood, Nov. 16, 2007, vol. 110(11). 2 pages (https://doi.org/10.1182/blood.V110.11.4492.4492).

* cited by examiner

```
                         SEQUENCE LISTING

<160> NUMBER OF SEQ ID NOS: 121

<210> SEQ ID NO 1
<211> LENGTH: 901
<212> TYPE: DNA
<213> ORGANISM: Homo sapiens
<220> FEATURE:
<221> NAME/KEY: CDS
<222> LOCATION: (119)..(757)
<220> FEATURE:
<221> NAME/KEY: sig_peptide
<222> LOCATION: (119)..(229)

<400> SEQUENCE: 1
ggccacatgg actggggtgc aatgggacag ctgctgccag cgagagggac cagggcacca        60
ctctctaggg agcccacact gcaagtcagg ccacaaggac ctctgaccct gagggccg        118 atg agg cca ggg aca ggc cag ggg ggc ctt gag gcc cct ggt gag cca        166
Met Arg Pro Gly Thr Gly Gln Gly Gly Leu Glu Ala Pro Gly Glu Pro
1               5                   10                  15 ggc ccc aac ctc agg cag cgc tgg ccc ctg ctg ctg ggt ctg gcc        214
Gly Pro Asn Leu Arg Gln Arg Trp Pro Leu Leu Leu Leu Gly Leu Ala
                20                  25                  30 gtg gta acc cat ggc ctg ctg cgc cca aca gct gca tcg cag agc agg        262
Val Val Thr His Gly Leu Leu Arg Pro Thr Ala Ala Ser Gln Ser Arg
            35                  40                  45 gcc ctg ggc cct gga gcc cct gga gga agc agc cgg tcc agc ctg agg        310
Ala Leu Gly Pro Gly Ala Pro Gly Gly Ser Ser Arg Ser Ser Leu Arg
        50                  55                  60 agc cgg tgg ggc agg ttc ctc ctc cag cgc ggc tcc tgg act ggc ccc        358
Ser Arg Trp Gly Arg Phe Leu Leu Gln Arg Gly Ser Trp Thr Gly Pro
65                  70                  75                  80 agg tgc tgg ccc cgg ggg ttt caa tcc aag cat aac tca gtg acg cat        406
Arg Cys Trp Pro Arg Gly Phe Gln Ser Lys His Asn Ser Val Thr His
                85                  90                  95 gtg ttt ggc agc ggg acc cag ctc acc gtt tta agt cag ccc aag gcc        454
Val Phe Gly Ser Gly Thr Gln Leu Thr Val Leu Ser Gln Pro Lys Ala
            100                 105                 110 acc ccc tcg gtc act ctg ttc ccg ccg tcc tct gag gag ctc caa gcc        502
Thr Pro Ser Val Thr Leu Phe Pro Pro Ser Ser Glu Glu Leu Gln Ala
        115                 120                 125 aac aag gct aca ctg gtg tgt ctc atg aat gac ttt tat ccg gga atc        550
Asn Lys Ala Thr Leu Val Cys Leu Met Asn Asp Phe Tyr Pro Gly Ile
    130                 135                 140 ttg acg gtg acc tgg aag gca gat ggt acc ccc atc acc cag ggc gtg        598
Leu Thr Val Thr Trp Lys Ala Asp Gly Thr Pro Ile Thr Gln Gly Val
145                 150                 155                 160 gag atg acc acg ccc tcc aaa cag agc aac aac aag tac gcg gcc agc        646
Glu Met Thr Thr Pro Ser Lys Gln Ser Asn Asn Lys Tyr Ala Ala Ser
```

```
Glu Met Thr Thr Pro Ser Lys Gln Ser Asn Asn Lys Tyr Ala Ala Ser
            165                 170                 175 agc tac ctg agc ctg acg ccc gag cag tgg agg tcc cgc aga agc tac        694
Ser Tyr Leu Ser Leu Thr Pro Glu Gln Trp Arg Ser Arg Arg Ser Tyr
        180                 185                 190 agc tgc cag gtc atg cac gaa ggg agc acc gtg gag aag acg gtg gcc        742
Ser Cys Gln Val Met His Glu Gly Ser Thr Val Glu Lys Thr Val Ala
    195                 200                 205 cct gca gaa tgt tca taggttccca gccccgaccc cacccaaagg ggcctggagc        797
Pro Ala Glu Cys Ser
    210 tgcaggatcc caggggaagg gtctctctct gcatcccaag ccatccagcc cttctccctg      857 tacccagtaa accctaaata aatacccctct ttgtcaacca gaaa                      901

<210> SEQ ID NO 2
<211> LENGTH: 213
<212> TYPE: PRT
<213> ORGANISM: Homo sapiens

<400> SEQUENCE: 2

Met Arg Pro Gly Thr Gly Gln Gly Gly Leu Glu Ala Pro Gly Glu Pro
1               5                   10                  15

Gly Pro Asn Leu Arg Gln Arg Trp Pro Leu Leu Leu Gly Leu Ala
            20                  25                  30

Val Val Thr His Gly Leu Leu Arg Pro Thr Ala Ala Ser Gln Ser Arg
        35                  40                  45

Ala Leu Gly Pro Gly Ala Pro Gly Gly Ser Ser Arg Ser Ser Leu Arg
    50                  55                  60

Ser Arg Trp Gly Arg Phe Leu Leu Gln Arg Gly Ser Trp Thr Gly Pro
65                  70                  75                  80

Arg Cys Trp Pro Arg Gly Phe Gln Ser Lys His Asn Ser Val Thr His
                85                  90                  95

Val Phe Gly Ser Gly Thr Gln Leu Thr Val Leu Ser Gln Pro Lys Ala
            100                 105                 110

Thr Pro Ser Val Thr Leu Phe Pro Pro Ser Ser Glu Glu Leu Gln Ala
        115                 120                 125

Asn Lys Ala Thr Leu Val Cys Leu Met Asn Asp Phe Tyr Pro Gly Ile
    130                 135                 140

Leu Thr Val Thr Trp Lys Ala Asp Gly Thr Pro Ile Thr Gln Gly Val
145                 150                 155                 160

Glu Met Thr Thr Pro Ser Lys Gln Ser Asn Asn Lys Tyr Ala Ala Ser
                165                 170                 175

Ser Tyr Leu Ser Leu Thr Pro Glu Gln Trp Arg Ser Arg Arg Ser Tyr
            180                 185                 190

Ser Cys Gln Val Met His Glu Gly Ser Thr Val Glu Lys Thr Val Ala
        195                 200                 205

Pro Ala Glu Cys Ser
    210

<210> SEQ ID NO 3
<211> LENGTH: 176
<212> TYPE: PRT
<213> ORGANISM: Homo sapiens

<400> SEQUENCE: 3

Leu Leu Arg Pro Thr Ala Ala Ser Gln Ser Arg Ala Leu Gly Pro Gly
1               5                   10                  15
```

```
Ala Pro Gly Gly Ser Ser Arg Ser Ser Leu Arg Ser Arg Trp Gly Arg
            20                  25                  30

Phe Leu Leu Gln Arg Gly Ser Trp Thr Gly Pro Arg Cys Trp Pro Arg
         35                  40                  45

Gly Phe Gln Ser Lys His Asn Ser Val Thr His Val Phe Gly Ser Gly
     50                  55                  60

Thr Gln Leu Thr Val Leu Ser Gln Pro Lys Ala Thr Pro Ser Val Thr
 65                  70                  75                  80

Leu Phe Pro Pro Ser Ser Glu Glu Leu Gln Ala Asn Lys Ala Thr Leu
                 85                  90                  95

Val Cys Leu Met Asn Asp Phe Tyr Pro Gly Ile Leu Thr Val Thr Trp
            100                 105                 110

Lys Ala Asp Gly Thr Pro Ile Thr Gln Gly Val Glu Met Thr Thr Pro
        115                 120                 125

Ser Lys Gln Ser Asn Asn Lys Tyr Ala Ala Ser Ser Tyr Leu Ser Leu
    130                 135                 140

Thr Pro Glu Gln Trp Arg Ser Arg Ser Tyr Ser Cys Gln Val Met
145                 150                 155                 160

His Glu Gly Ser Thr Val Glu Lys Thr Val Ala Pro Ala Glu Cys Ser
                165                 170                 175

<210> SEQ ID NO 4
<211> LENGTH: 513
<212> TYPE: DNA
<213> ORGANISM: Canis familiaris
<220> FEATURE:
<221> NAME/KEY: CDS
<222> LOCATION: (2)..(361)

<400> SEQUENCE: 4 c agg gct cct ctt ttc ggc gga ggc acc cac ctg acc gtc ctc ggt cag     49
  Arg Ala Pro Leu Phe Gly Gly Gly Thr His Leu Thr Val Leu Gly Gln
   1               5                  10                  15 ccc aag gcc tcc ccc tcg gtc aca ctc ttc ccg ccc tcc tct gag gag       97
Pro Lys Ala Ser Pro Ser Val Thr Leu Phe Pro Pro Ser Ser Glu Glu
             20                  25                  30 ctc ggc gcc aac aag gcc acc ctg gtg tgc ctc atc agc gac ttc tac      145
Leu Gly Ala Asn Lys Ala Thr Leu Val Cys Leu Ile Ser Asp Phe Tyr
         35                  40                  45 ccc agc ggc gtg acg gtg gcc tgg aag gca gac ggc agc ccc gtc acc      193
Pro Ser Gly Val Thr Val Ala Trp Lys Ala Asp Gly Ser Pro Val Thr
     50                  55                  60 cag ggc gtg gag acc acc aag ccc tcc aag cag agc aac aac aag tac      241
Gln Gly Val Glu Thr Thr Lys Pro Ser Lys Gln Ser Asn Asn Lys Tyr
 65                  70                  75                  80 gcg gcc agc agc tac ctg agc ctg acg cct gac aag tgg aaa tct cac      289
Ala Ala Ser Ser Tyr Leu Ser Leu Thr Pro Asp Lys Trp Lys Ser His
                 85                  90                  95 agc agc ttc agc tgc ctg gtc acg cac gag ggg agc acc gtg gag aag      337
Ser Ser Phe Ser Cys Leu Val Thr His Glu Gly Ser Thr Val Glu Lys
            100                 105                 110 aag gtg gcc ccc gca gag tgc tct taggttcccg acggccccgc ccaccgaagg     391
Lys Val Ala Pro Ala Glu Cys Ser
        115                 120 gggcccggag cctcaggacc tccaggagga tcttgcctcc catctgggtc atcccgccct    451
tctccccgca cccaggcagc actcaataaa gtgttctttg ttcaatcaga aaaaaaaaaa    511
aa                                                                   513
```

<210> SEQ ID NO 5
<211> LENGTH: 120
<212> TYPE: PRT
<213> ORGANISM: Canis familiaris

<400> SEQUENCE: 5

Arg Ala Pro Leu Phe Gly Gly Thr His Leu Thr Val Leu Gly Gln
1               5                   10                  15

Pro Lys Ala Ser Pro Ser Val Thr Leu Phe Pro Pro Ser Ser Glu Glu
            20                  25                  30

Leu Gly Ala Asn Lys Ala Thr Leu Val Cys Leu Ile Ser Asp Phe Tyr
        35                  40                  45

Pro Ser Gly Val Thr Val Ala Trp Lys Ala Asp Gly Ser Pro Val Thr
    50                  55                  60

Gln Gly Val Glu Thr Thr Lys Pro Ser Lys Gln Ser Asn Asn Lys Tyr
65                  70                  75                  80

Ala Ala Ser Ser Tyr Leu Ser Leu Thr Pro Asp Lys Trp Lys Ser His
                85                  90                  95

Ser Ser Phe Ser Cys Leu Val Thr His Glu Gly Ser Thr Val Glu Lys
            100                 105                 110

Lys Val Ala Pro Ala Glu Cys Ser
        115                 120

<210> SEQ ID NO 6
<211> LENGTH: 659
<212> TYPE: DNA
<213> ORGANISM: Canis familiaris
<220> FEATURE:
<221> NAME/KEY: CDS
<222> LOCATION: (2)..(481)

<400> SEQUENCE: 6 c tcg ggg gtc ccg gat cga ttc tct acc tcc agg tca ggc tac aca gcc     49
  Ser Gly Val Pro Asp Arg Phe Ser Thr Ser Arg Ser Gly Tyr Thr Ala
   1               5                   10                  15 acc ctg acc atc tct ggg ctc cag gct gag gac gaa ggt gat tat tac       97
Thr Leu Thr Ile Ser Gly Leu Gln Ala Glu Asp Glu Gly Asp Tyr Tyr
            20                  25                  30 tgc tca aca tgg gac aac gat ctc aaa ggc agt gtt ttc ggc ggg ggc      145
Cys Ser Thr Trp Asp Asn Asp Leu Lys Gly Ser Val Phe Gly Gly Gly
        35                  40                  45 acc cat ctg acc gtc ctc ggt cag ccc aag gcc tcc ccc tcg gtc aca      193
Thr His Leu Thr Val Leu Gly Gln Pro Lys Ala Ser Pro Ser Val Thr
    50                  55                  60 ctc ttc ccg ccc tcc tct gag gaa ctc ggc gcc aac aag gcc acc ctg      241
Leu Phe Pro Pro Ser Ser Glu Glu Leu Gly Ala Asn Lys Ala Thr Leu
65                  70                  75                  80 gtg tgc ctc atc agc gac ttc tac ccc agt ggc gtg acg gtg gcc tgg      289
Val Cys Leu Ile Ser Asp Phe Tyr Pro Ser Gly Val Thr Val Ala Trp
                85                  90                  95 aag gca gac ggc agc ccc gtc acc cag ggc gtg gag acc acc aag ccc      337
Lys Ala Asp Gly Ser Pro Val Thr Gln Gly Val Glu Thr Thr Lys Pro
            100                 105                 110 tcc aag cag agc aac aac aag tac gcg gcc agc agc tac ctg agc ctg      385
Ser Lys Gln Ser Asn Asn Lys Tyr Ala Ala Ser Ser Tyr Leu Ser Leu
        115                 120                 125 acg cct gac aag tgg aaa tct cac agc agc ttc agc tgc ctg gtc aca      433
Thr Pro Asp Lys Trp Lys Ser His Ser Ser Phe Ser Cys Leu Val Thr
    130                 135                 140

```
cac gag ggg agc acc gtg gag aag aag gtg gcc ccc gca gag tgc tct    481
His Glu Gly Ser Thr Val Glu Lys Lys Val Ala Pro Ala Glu Cys Ser
145                 150                 155                 160 taggttcccg acgccccgc ccacctaagg gggcccggag cctcaggacc tccaggagga    541
tcttgcctcc tatctgggtc atcccgccct tctccccaca cccaggcagc actcaataaa    601
gtgttctttg ttcaatctga aaaaaaaaaa aaaaaaaaaa aaaaaaaaaa aaaaaaa       659

<210> SEQ ID NO 7
<211> LENGTH: 160
<212> TYPE: PRT
<213> ORGANISM: Canis familiaris

<400> SEQUENCE: 7

Ser Gly Val Pro Asp Arg Phe Ser Thr Ser Arg Ser Gly Tyr Thr Ala
1               5                   10                  15

Thr Leu Thr Ile Ser Gly Leu Gln Ala Glu Asp Glu Gly Asp Tyr Tyr
            20                  25                  30

Cys Ser Thr Trp Asp Asn Asp Leu Lys Gly Ser Val Phe Gly Gly Gly
        35                  40                  45

Thr His Leu Thr Val Leu Gly Gln Pro Lys Ala Ser Pro Ser Val Thr
    50                  55                  60

Leu Phe Pro Pro Ser Ser Glu Glu Leu Gly Ala Asn Lys Ala Thr Leu
65                  70                  75                  80

Val Cys Leu Ile Ser Asp Phe Tyr Pro Ser Gly Val Thr Val Ala Trp
                85                  90                  95

Lys Ala Asp Gly Ser Pro Val Thr Gln Gly Val Glu Thr Thr Lys Pro
            100                 105                 110

Ser Lys Gln Ser Asn Asn Lys Tyr Ala Ala Ser Ser Tyr Leu Ser Leu
        115                 120                 125

Thr Pro Asp Lys Trp Lys Ser His Ser Ser Phe Ser Cys Leu Val Thr
    130                 135                 140

His Glu Gly Ser Thr Val Glu Lys Lys Val Ala Pro Ala Glu Cys Ser
145                 150                 155                 160

<210> SEQ ID NO 8
<211> LENGTH: 634
<212> TYPE: DNA
<213> ORGANISM: Canis familiaris
<220> FEATURE:
<221> NAME/KEY: CDS
<222> LOCATION: (2)..(493)

<400> SEQUENCE: 8 g gac act gaa cgg ccc tct ggg atc cct gac cgc ttc tct ggc tcc agt    49
  Asp Thr Glu Arg Pro Ser Gly Ile Pro Asp Arg Phe Ser Gly Ser Ser
  1               5                   10                  15 tca ggg aac aca cac acc ctg acc atc aga ggg gct cgg gcc gag gac      97
Ser Gly Asn Thr His Thr Leu Thr Ile Arg Gly Ala Arg Ala Glu Asp
            20                  25                  30 gag gct gac tat tac tgc gag tca gca gtc agt act gat atc ggc gtg     145
Glu Ala Asp Tyr Tyr Cys Glu Ser Ala Val Ser Thr Asp Ile Gly Val
        35                  40                  45 ttc ggc gga ggc acc cac ctg acc gtc ctc ggt cag ccc agg gcc tcc     193
Phe Gly Gly Gly Thr His Leu Thr Val Leu Gly Gln Pro Arg Ala Ser
    50                  55                  60 ccc tcg gtc aca ctc ttc ccg ccc tcc tct gag gag ctc ggc gcc aac     241
Pro Ser Val Thr Leu Phe Pro Pro Ser Ser Glu Glu Leu Gly Ala Asn
65                  70                  75                  80
```

```
aag gcc acc ctg gtg tgc ctc atc agc gac ttc tac ccc agc ggt gtg      289
Lys Ala Thr Leu Val Cys Leu Ile Ser Asp Phe Tyr Pro Ser Gly Val
             85                  90                  95 acg gtg gcc tgg aag gca gac ggc agc ccc gtc acc cag ggc gtg gag      337
Thr Val Ala Trp Lys Ala Asp Gly Ser Pro Val Thr Gln Gly Val Glu
        100                 105                 110 acc acc aag ccc tcc aag cag agc aac aac aag tac gcg gcc agc agc      385
Thr Thr Lys Pro Ser Lys Gln Ser Asn Asn Lys Tyr Ala Ala Ser Ser
        115                 120                 125 tac ctg agc ctg acg cct gac aag tgg aaa tct cac agc agc ttc agc      433
Tyr Leu Ser Leu Thr Pro Asp Lys Trp Lys Ser His Ser Ser Phe Ser
    130                 135                 140 tgc ctg gtc acg cac gag ggg agc acc gtg gag aag aag gtg gcc ccc      481
Cys Leu Val Thr His Glu Gly Ser Thr Val Glu Lys Lys Val Ala Pro
145                 150                 155                 160 gca gag tgc tct taggttcccg acggcccgc ccaccgaagg gggcccggag           533
Ala Glu Cys Ser cctcaggacc tccaggagga tcttgcctcc catctgggtc atcccgctct tctccccgca    593
cccaggcagc actcaataaa gtgttctttg ttcaatcaaa a                        634

<210> SEQ ID NO 9
<211> LENGTH: 164
<212> TYPE: PRT
<213> ORGANISM: Canis familiaris

<400> SEQUENCE: 9

Asp Thr Glu Arg Pro Ser Gly Ile Pro Asp Arg Phe Ser Gly Ser Ser
1               5                   10                  15

Ser Gly Asn Thr His Thr Leu Thr Ile Arg Gly Ala Arg Ala Glu Asp
            20                  25                  30

Glu Ala Asp Tyr Tyr Cys Glu Ser Ala Val Ser Thr Asp Ile Gly Val
        35                  40                  45

Phe Gly Gly Gly Thr His Leu Thr Val Leu Gly Gln Pro Arg Ala Ser
    50                  55                  60

Pro Ser Val Thr Leu Phe Pro Pro Ser Ser Glu Glu Leu Gly Ala Asn
65                  70                  75                  80

Lys Ala Thr Leu Val Cys Leu Ile Ser Asp Phe Tyr Pro Ser Gly Val
                85                  90                  95

Thr Val Ala Trp Lys Ala Asp Gly Ser Pro Val Thr Gln Gly Val Glu
        100                 105                 110

Thr Thr Lys Pro Ser Lys Gln Ser Asn Asn Lys Tyr Ala Ala Ser Ser
    115                 120                 125

Tyr Leu Ser Leu Thr Pro Asp Lys Trp Lys Ser His Ser Ser Phe Ser
130                 135                 140

Cys Leu Val Thr His Glu Gly Ser Thr Val Glu Lys Lys Val Ala Pro
145                 150                 155                 160

Ala Glu Cys Ser

<210> SEQ ID NO 10
<211> LENGTH: 635
<212> TYPE: DNA
<213> ORGANISM: Canis familiaris
<220> FEATURE:
<221> NAME/KEY: CDS
<222> LOCATION: (2)..(487)

<400> SEQUENCE: 10
```

```
c cga cct gca ggg gta ccc gat cga ttc tct ggg tcc aag tca ggc ggg        49
  Arg Pro Ala Gly Val Pro Asp Arg Phe Ser Gly Ser Lys Ser Gly Gly
  1               5                   10                  15 tca gcc atc ctg acc atc tct ggg ctc cag cct gag gac gaa tgt gat          97
Ser Ala Ile Leu Thr Ile Ser Gly Leu Gln Pro Glu Asp Glu Cys Asp
            20                  25                  30 tat tac tgt tcg tct tgg gat aag ggt ctc agc agg tcc gtg ttc ggc         145
Tyr Tyr Cys Ser Ser Trp Asp Lys Gly Leu Ser Arg Ser Val Phe Gly
        35                  40                  45 gga ggc acc cac ctg acc gtc ctc ggt cag ccc aag gcc tcc ccc tcg         193
Gly Gly Thr His Leu Thr Val Leu Gly Gln Pro Lys Ala Ser Pro Ser
50                  55                  60 gtc aca ctc ttc ccg ccc tcc tct gag gag ctc ggc gcc aac aag gcc         241
Val Thr Leu Phe Pro Pro Ser Ser Glu Glu Leu Gly Ala Asn Lys Ala
65              70                  75                  80 acc ctg gtg tgc ctc atc agc gac ttc tac ccc agc ggc gtg acg gtg         289
Thr Leu Val Cys Leu Ile Ser Asp Phe Tyr Pro Ser Gly Val Thr Val
                85                  90                  95 gcc tgg aag gca gac ggc agc ccc gtc acc cag ggc gtg gag acc acc         337
Ala Trp Lys Ala Asp Gly Ser Pro Val Thr Gln Gly Val Glu Thr Thr
            100                 105                 110 aag ccc tcc aag cag agc aac aac aag tac gcg gcc agc agc tac ctg         385
Lys Pro Ser Lys Gln Ser Asn Asn Lys Tyr Ala Ala Ser Ser Tyr Leu
        115                 120                 125 agc ctg acg cct gac aag tgg aaa tct cac agc agc ttc agc tgc ctg         433
Ser Leu Thr Pro Asp Lys Trp Lys Ser His Ser Ser Phe Ser Cys Leu
    130                 135                 140 gtc acg cac gag ggg agc acc gtg gag aag aag gtg gcc ccc gca gag         481
Val Thr His Glu Gly Ser Thr Val Glu Lys Lys Val Ala Pro Ala Glu
145                 150                 155                 160 tgc tct taggttcccg acggccccgc ccaccgaagg gggcccggag cctcaggacc          537
Cys Ser tccaggagga tcttgcctcc catctgggtc atcccgccct ctccccgca cccaggcagc        597 actcaataaa gtgttctttg ttcaatcaga aaaaaaa                                 635

<210> SEQ ID NO 11
<211> LENGTH: 162
<212> TYPE: PRT
<213> ORGANISM: Canis familiaris

<400> SEQUENCE: 11

Arg Pro Ala Gly Val Pro Asp Arg Phe Ser Gly Ser Lys Ser Gly Gly
1               5                   10                  15

Ser Ala Ile Leu Thr Ile Ser Gly Leu Gln Pro Glu Asp Glu Cys Asp
            20                  25                  30

Tyr Tyr Cys Ser Ser Trp Asp Lys Gly Leu Ser Arg Ser Val Phe Gly
        35                  40                  45

Gly Gly Thr His Leu Thr Val Leu Gly Gln Pro Lys Ala Ser Pro Ser
    50                  55                  60

Val Thr Leu Phe Pro Pro Ser Ser Glu Glu Leu Gly Ala Asn Lys Ala
65              70                  75                  80

Thr Leu Val Cys Leu Ile Ser Asp Phe Tyr Pro Ser Gly Val Thr Val
                85                  90                  95

Ala Trp Lys Ala Asp Gly Ser Pro Val Thr Gln Gly Val Glu Thr Thr
            100                 105                 110

Lys Pro Ser Lys Gln Ser Asn Asn Lys Tyr Ala Ala Ser Ser Tyr Leu
        115                 120                 125
```

-continued

```
Ser Leu Thr Pro Asp Lys Trp Lys Ser His Ser Ser Phe Ser Cys Leu
    130                 135                 140

Val Thr His Glu Gly Ser Thr Val Glu Lys Lys Val Ala Pro Ala Glu
145                 150                 155                 160

Cys Ser

<210> SEQ ID NO 12
<211> LENGTH: 583
<212> TYPE: DNA
<213> ORGANISM: Canis familiaris
<220> FEATURE:
<221> NAME/KEY: CDS
<222> LOCATION: (2)..(442)

<400> SEQUENCE: 12 c aaa gcc gcc ctc acc atc aca gga gcc cag cct gag gac gag gct gac      49
  Lys Ala Ala Leu Thr Ile Thr Gly Ala Gln Pro Glu Asp Glu Ala Asp
  1               5                   10                  15 tac tac tgt gct ctg gga tta agt agt agt agt agc cat agt gtg ttc        97
Tyr Tyr Cys Ala Leu Gly Leu Ser Ser Ser Ser Ser His Ser Val Phe
            20                  25                  30 ggc gga ggc acc cat ctg acc gtc ctc ggt cag ccc aag gcc tcc ccc       145
Gly Gly Gly Thr His Leu Thr Val Leu Gly Gln Pro Lys Ala Ser Pro
        35                  40                  45 tcg gtc aca ctc ttc ccg ccc tcc tct gag gag ctc ggc gcc aac aag       193
Ser Val Thr Leu Phe Pro Pro Ser Ser Glu Glu Leu Gly Ala Asn Lys
    50                  55                  60 gcc acc ctg gtg tgc ctc atc agc gac ttc tac ccc agt ggc gtg acg       241
Ala Thr Leu Val Cys Leu Ile Ser Asp Phe Tyr Pro Ser Gly Val Thr
65                  70                  75                  80 gtg gcc tgg aag gca gac ggc agc ccc gtc acc cag ggc gtg gag acc       289
Val Ala Trp Lys Ala Asp Gly Ser Pro Val Thr Gln Gly Val Glu Thr
                85                  90                  95 acc aag ccc tcc aag cag agc aac aac aag tac gcg gcc agc agc tac       337
Thr Lys Pro Ser Lys Gln Ser Asn Asn Lys Tyr Ala Ala Ser Ser Tyr
            100                 105                 110 ctg agc ctg acg cct gac aag tgg aaa tct cac agc agc ttc agc tgc       385
Leu Ser Leu Thr Pro Asp Lys Trp Lys Ser His Ser Ser Phe Ser Cys
        115                 120                 125 ctg gtc aca cac gag ggg agc acc gtg gag aag aag gtg gcc ccc gca       433
Leu Val Thr His Glu Gly Ser Thr Val Glu Lys Lys Val Ala Pro Ala
    130                 135                 140 gag tgc tct taggttcccg acgccccgc ccacctaagg gggcccggag               482
Glu Cys Ser
145 cctcaggacc tccaggagga tcttgcctcc tatctgggtc atcccgccct tctccccaca    542 cccaggcagc actcaataaa gtgttctttg ttcaatcaga a                        583

<210> SEQ ID NO 13
<211> LENGTH: 147
<212> TYPE: PRT
<213> ORGANISM: Canis familiaris

<400> SEQUENCE: 13

Lys Ala Ala Leu Thr Ile Thr Gly Ala Gln Pro Glu Asp Glu Ala Asp
1               5                   10                  15

Tyr Tyr Cys Ala Leu Gly Leu Ser Ser Ser Ser Ser His Ser Val Phe
            20                  25                  30

Gly Gly Gly Thr His Leu Thr Val Leu Gly Gln Pro Lys Ala Ser Pro
        35                  40                  45
```

```
Ser Val Thr Leu Phe Pro Pro Ser Ser Glu Glu Leu Gly Ala Asn Lys
    50                  55                  60

Ala Thr Leu Val Cys Leu Ile Ser Asp Phe Tyr Pro Ser Gly Val Thr
 65                  70                  75                  80

Val Ala Trp Lys Ala Asp Gly Ser Pro Val Thr Gln Gly Val Glu Thr
                 85                  90                  95

Thr Lys Pro Ser Lys Gln Ser Asn Asn Lys Tyr Ala Ala Ser Ser Tyr
            100                 105                 110

Leu Ser Leu Thr Pro Asp Lys Trp Lys Ser His Ser Ser Phe Ser Cys
        115                 120                 125

Leu Val Thr His Glu Gly Ser Thr Val Glu Lys Lys Val Ala Pro Ala
        130                 135                 140

Glu Cys Ser
145

<210> SEQ ID NO 14
<211> LENGTH: 796
<212> TYPE: DNA
<213> ORGANISM: Canis familiaris
<220> FEATURE:
<221> NAME/KEY: CDS
<222> LOCATION: (2)..(640)

<400> SEQUENCE: 14 g ctg act cag ccg gcc tca gtg tct ggg tcc ctg ggc cag agg atc acc      49
  Leu Thr Gln Pro Ala Ser Val Ser Gly Ser Leu Gly Gln Arg Ile Thr
   1               5                  10                  15 atc tcc tgc act gga agc agc tcc aac att gga ggt aat aat gtg ggt       97
Ile Ser Cys Thr Gly Ser Ser Ser Asn Ile Gly Gly Asn Asn Val Gly
             20                  25                  30 tgg tac cag cag ctc cca gga aga ggc ccc aga act gtc atc ttt act      145
Trp Tyr Gln Gln Leu Pro Gly Arg Gly Pro Arg Thr Val Ile Phe Thr
         35                  40                  45 aca cat agt cga ccc tcg ggg gtg tcc gat cga ttc tct gcc tcc aag      193
Thr His Ser Arg Pro Ser Gly Val Ser Asp Arg Phe Ser Ala Ser Lys
     50                  55                  60 tct ggc agc aca gcc acc ctg acc atc tct ggg ctc cag gct gag gat      241
Ser Gly Ser Thr Ala Thr Leu Thr Ile Ser Gly Leu Gln Ala Glu Asp
 65                  70                  75                  80 gag gct gat tat tac tgc tca acg tgg gat gat agt ctc agt gct gct      289
Glu Ala Asp Tyr Tyr Cys Ser Thr Trp Asp Asp Ser Leu Ser Ala Ala
                 85                  90                  95 gtg ttc ggc gga ggc acc cac ctg acc gtc ctc ggt cag ccc aag gcc      337
Val Phe Gly Gly Gly Thr His Leu Thr Val Leu Gly Gln Pro Lys Ala
            100                 105                 110 tcc ccc tcg gtc aca ctc ttc ccg ccc tcc tct gag gag ctc ggc gcc      385
Ser Pro Ser Val Thr Leu Phe Pro Pro Ser Ser Glu Glu Leu Gly Ala
        115                 120                 125 aac aag gcc acc ctg gtg tgc ctc atc agc gac ttc tac ccc agc ggc      433
Asn Lys Ala Thr Leu Val Cys Leu Ile Ser Asp Phe Tyr Pro Ser Gly
    130                 135                 140 gtg acg gtg gcc tgg aag gca gac ggc agc ccc gtc acc cag ggc gtg      481
Val Thr Val Ala Trp Lys Ala Asp Gly Ser Pro Val Thr Gln Gly Val
145                 150                 155                 160 gag acc acc aag ccc tcc aag cag agc aac aac aag tac gcg gcc agc      529
Glu Thr Thr Lys Pro Ser Lys Gln Ser Asn Asn Lys Tyr Ala Ala Ser
                165                 170                 175 agc tac ctg agc ctg acg cct gac aag tgg aaa tct cac agc agc ttc      577
Ser Tyr Leu Ser Leu Thr Pro Asp Lys Trp Lys Ser His Ser Ser Phe
```

```
                    180              185              190
agc tgc ctg gtc acg cac gag ggg agc acc gtg gag aag aag gtg gcc     625
Ser Cys Leu Val Thr His Glu Gly Ser Thr Val Glu Lys Lys Val Ala
    195              200              205 ccc gca gag tgc tct taggttccg acggccgc ccaccgaagg gggcccggag        680
Pro Ala Glu Cys Ser
    210 cctcaggacc tccaggagga tcttgcctcc catctgggtc atcccgccct tctccccgca    740 cccaggcagc actcaataaa gtgttctttg ttcaatcaaa aaaaaaaaaa aaaaaa       796

<210> SEQ ID NO 15
<211> LENGTH: 213
<212> TYPE: PRT
<213> ORGANISM: Canis familiaris

<400> SEQUENCE: 15

Leu Thr Gln Pro Ala Ser Val Ser Gly Ser Leu Gly Gln Arg Ile Thr
1               5                   10                  15

Ile Ser Cys Thr Gly Ser Ser Ser Asn Ile Gly Gly Asn Asn Val Gly
            20                  25                  30

Trp Tyr Gln Gln Leu Pro Gly Arg Gly Pro Arg Thr Val Ile Phe Thr
        35                  40                  45

Thr His Ser Arg Pro Ser Gly Val Ser Asp Arg Phe Ser Ala Ser Lys
    50                  55                  60

Ser Gly Ser Thr Ala Thr Leu Thr Ile Ser Gly Leu Gln Ala Glu Asp
65                  70                  75                  80

Glu Ala Asp Tyr Tyr Cys Ser Thr Trp Asp Asp Ser Leu Ser Ala Ala
                85                  90                  95

Val Phe Gly Gly Gly Thr His Leu Thr Val Leu Gly Gln Pro Lys Ala
            100                 105                 110

Ser Pro Ser Val Thr Leu Phe Pro Pro Ser Glu Glu Leu Gly Ala
        115                 120                 125

Asn Lys Ala Thr Leu Val Cys Leu Ile Ser Asp Phe Tyr Pro Ser Gly
    130                 135                 140

Val Thr Val Ala Trp Lys Ala Asp Gly Ser Pro Val Thr Gln Gly Val
145                 150                 155                 160

Glu Thr Thr Lys Pro Ser Lys Gln Ser Asn Asn Lys Tyr Ala Ala Ser
                165                 170                 175

Ser Tyr Leu Ser Leu Thr Pro Asp Lys Trp Lys Ser His Ser Ser Phe
            180                 185                 190

Ser Cys Leu Val Thr His Glu Gly Ser Thr Val Glu Lys Lys Val Ala
        195                 200                 205

Pro Ala Glu Cys Ser
    210

<210> SEQ ID NO 16
<211> LENGTH: 1306
<212> TYPE: DNA
<213> ORGANISM: Canis familiaris
<220> FEATURE:
<221> NAME/KEY: CDS
<222> LOCATION: (2)..(643)

<400> SEQUENCE: 16 c tcc tat gtg ctg aca cag ctg cca tcc atg act gtg acc ctg aag cag     49
  Ser Tyr Val Leu Thr Gln Leu Pro Ser Met Thr Val Thr Leu Lys Gln
  1               5                   10                  15
```

| | | |
|---|---|---|
| acg gcc cgc atc acc tgt gag gga gac agc att gga agc aaa aga gtt<br>Thr Ala Arg Ile Thr Cys Glu Gly Asp Ser Ile Gly Ser Lys Arg Val<br>20 25 30 | | 97 |
| tac tgg tac caa cag aac ctg ggc cag gtc cct cta ctg att atc tat<br>Tyr Trp Tyr Gln Gln Asn Leu Gly Gln Val Pro Leu Leu Ile Ile Tyr<br>35 40 45 | | 145 |
| gat gat gcc acc agg ccg tca agg atc cct gac cga ttc tcc ggc gcc<br>Asp Asp Ala Thr Arg Pro Ser Arg Ile Pro Asp Arg Phe Ser Gly Ala<br>50 55 60 | | 193 |
| aac tcg ggg gac aca gcc acc ctg acc atc agc ggg gcc ctg gcc gag<br>Asn Ser Gly Asp Thr Ala Thr Leu Thr Ile Ser Gly Ala Leu Ala Glu<br>65 70 75 80 | | 241 |
| gac gag gct gac tat tac tgt cag gtg tgg gac agt gat agt aag act<br>Asp Glu Ala Asp Tyr Tyr Cys Gln Val Trp Asp Ser Asp Ser Lys Thr<br>85 90 95 | | 289 |
| ggt gta ttc ggc gga ggc acc cac ctg acc gtc ctc ggt cag ccc aag<br>Gly Val Phe Gly Gly Gly Thr His Leu Thr Val Leu Gly Gln Pro Lys<br>100 105 110 | | 337 |
| gcc tcc ccc tcg gtc aca ctc ttc ccg ccc tcc tct gag gag ctc ggc<br>Ala Ser Pro Ser Val Thr Leu Phe Pro Pro Ser Ser Glu Glu Leu Gly<br>115 120 125 | | 385 |
| gcc aac aag gcc acc ctg gtg tgc ctc atc agc gac ttc tac ccc agc<br>Ala Asn Lys Ala Thr Leu Val Cys Leu Ile Ser Asp Phe Tyr Pro Ser<br>130 135 140 | | 433 |
| ggt gtg acg gtg gcc tgg aag gca gac ggc agc ccc gtc acc cag ggc<br>Gly Val Thr Val Ala Trp Lys Ala Asp Gly Ser Pro Val Thr Gln Gly<br>145 150 155 160 | | 481 |
| gtg gag acc acc aag ccc tcc aag cag agc aac aac aag tac gcg gcc<br>Val Glu Thr Thr Lys Pro Ser Lys Gln Ser Asn Asn Lys Tyr Ala Ala<br>165 170 175 | | 529 |
| agc agc tac ctg agc ctg acg cct gac aag tgg aaa tct cac agc agc<br>Ser Ser Tyr Leu Ser Leu Thr Pro Asp Lys Trp Lys Ser His Ser Ser<br>180 185 190 | | 577 |
| ttc agc tgc ctg gtc acg cac gag ggg agc acc gtg gag aag aag gtg<br>Phe Ser Cys Leu Val Thr His Glu Gly Ser Thr Val Glu Lys Lys Val<br>195 200 205 | | 625 |
| gcc ccc gca gag tgc tct taggttcccg acggccccgc ccaccgaagg<br>Ala Pro Ala Glu Cys Ser<br>210 | | 673 |
| gggcccggag cctcaggacc tccaggagga tcttgcctcc catctgggtc atcccgctct | | 733 |
| tctccccgca cccaggcagc actcaataaa gtgttctttg ttcaatcaga aaaaaaaaaa | | 793 |
| aaaaaaaaac tcgagccggc tggagtctgg gatgcagaac atgagcatcc atacgaagac | | 853 |
| gaccagcggc tactccggtg gcctgaactt ggcctacggg ggcctcacga gccccggcct | | 913 |
| caactacggc cagagctcct tccagtccgg ctttggccct ggcggttcct tcagccgcag | | 973 |
| cagctcctcc aaggccgtgg ttgtgaagaa gatcgagact cgcgatggga agctggtgtc | | 1033 |
| tgagtcgtct gacgtcctgc ccaagtgaac ggccagcgcg ggcccccca gcctccttgc | | 1093 |
| tcttgtggcc ccatgaagcc ttcggggaa ggagctgtgc aggggagcct cgcgtacgag | | 1153 |
| agacccgcct aaggctcagc cccggtcccc agcctaccct taggggagt ctactgccct | | 1213 |
| gggtacccct tcttgtccgt gccccgacc gaaagccaat tcaagtgtct tttcccaaat | | 1273 |
| aaagccgctg ccagtcccaa aaaaaaaaaa aaa | | 1306 |

<210> SEQ ID NO 17
<211> LENGTH: 214
<212> TYPE: PRT
<213> ORGANISM: Canis familiaris

<400> SEQUENCE: 17

```
Ser Tyr Val Leu Thr Gln Leu Pro Ser Met Thr Val Thr Leu Lys Gln
1               5                   10                  15

Thr Ala Arg Ile Thr Cys Glu Gly Asp Ser Ile Gly Ser Lys Arg Val
            20                  25                  30

Tyr Trp Tyr Gln Gln Asn Leu Gly Gln Val Pro Leu Leu Ile Ile Tyr
        35                  40                  45

Asp Asp Ala Thr Arg Pro Ser Arg Ile Pro Asp Arg Phe Ser Gly Ala
    50                  55                  60

Asn Ser Gly Asp Thr Ala Thr Leu Thr Ile Ser Gly Ala Leu Ala Glu
65                  70                  75                  80

Asp Glu Ala Asp Tyr Tyr Cys Gln Val Trp Asp Ser Asp Ser Lys Thr
                85                  90                  95

Gly Val Phe Gly Gly Gly Thr His Leu Thr Val Leu Gly Gln Pro Lys
            100                 105                 110

Ala Ser Pro Ser Val Thr Leu Phe Pro Pro Ser Glu Glu Leu Gly
            115                 120                 125

Ala Asn Lys Ala Thr Leu Val Cys Leu Ile Ser Asp Phe Tyr Pro Ser
        130                 135                 140

Gly Val Thr Val Ala Trp Lys Ala Asp Gly Ser Pro Val Thr Gln Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Asp Lys Trp Lys Ser His Ser Ser
            180                 185                 190

Phe Ser Cys Leu Val Thr His Glu Gly Ser Thr Val Glu Lys Lys Val
        195                 200                 205

Ala Pro Ala Glu Cys Ser
        210
```

<210> SEQ ID NO 18
<211> LENGTH: 859
<212> TYPE: DNA
<213> ORGANISM: Canis familiaris
<220> FEATURE:
<221> NAME/KEY: CDS
<222> LOCATION: (2)..(715)

<400> SEQUENCE: 18

```
g acc tcc aac atg gcc tgg tcc cct ctc ctc ctc aca ctc ctt gct tcc    49
  Thr Ser Asn Met Ala Trp Ser Pro Leu Leu Leu Thr Leu Leu Ala Ser
  1               5                   10                  15 tgc aca gga tcc tgg gcc cag tct gtg cta act cag ccg acc tcg gtg    97
Cys Thr Gly Ser Trp Ala Gln Ser Val Leu Thr Gln Pro Thr Ser Val
            20                  25                  30 tcg ggg tcc ctt ggc cag agg gtc acc atc tcc tgc tct ggc agc tcg   145
Ser Gly Ser Leu Gly Gln Arg Val Thr Ile Ser Cys Ser Gly Ser Ser
        35                  40                  45 acc aac atc ggt tct gtt ggt gcg act tgg tac caa cac ctc cca gga   193
Thr Asn Ile Gly Ser Val Gly Ala Thr Trp Tyr Gln His Leu Pro Gly
    50                  55                  60 aag gcc cct aga ctc ctc ctc tac aca cat ggg gaa cgg ccg tca ggg   241
Lys Ala Pro Arg Leu Leu Leu Tyr Thr His Gly Glu Arg Pro Ser Gly
65                  70                  75                  80 atc cct gac cgg ttt tcc ggc tcc gag tct gcc aac tcg gac acc ctg   289
Ile Pro Asp Arg Phe Ser Gly Ser Glu Ser Ala Asn Ser Asp Thr Leu
                85                  90                  95
```

```
acc atc act gga ctt cag gct gag gac gag gct gat tac tac tgc cag    337
Thr Ile Thr Gly Leu Gln Ala Glu Asp Glu Ala Asp Tyr Tyr Cys Gln
            100                 105                 110 tcc ttt gat agc acg ctt gag act gct gtg ttc ggc ggc act cac        385
Ser Phe Asp Ser Thr Leu Glu Thr Ala Val Phe Gly Gly Gly Thr His
        115                 120                 125 ctg acc gtc ctt ggt cag ccc aag gcc tcc ccc tcg gtc aca ctc ttc    433
Leu Thr Val Leu Gly Gln Pro Lys Ala Ser Pro Ser Val Thr Leu Phe
130                 135                 140 ccg ccc tcc tct gag gag ctc ggc gcc aac aag gcc acc ctg gtg tgc    481
Pro Pro Ser Ser Glu Glu Leu Gly Ala Asn Lys Ala Thr Leu Val Cys
145                 150                 155                 160 ctc atc agc gac ttc tac ccc agc ggc gtg acg gtg gcc tgg aag gca    529
Leu Ile Ser Asp Phe Tyr Pro Ser Gly Val Thr Val Ala Trp Lys Ala
                165                 170                 175 gac ggc agc ccc gtc acc cag ggc gtg gag acc acc aag ccc tcc aag    577
Asp Gly Ser Pro Val Thr Gln Gly Val Glu Thr Thr Lys Pro Ser Lys
            180                 185                 190 cag agc aac aac aag tac gcg gcc agc agc tac ctg agc ctg acg cct    625
Gln Ser Asn Asn Lys Tyr Ala Ala Ser Ser Tyr Leu Ser Leu Thr Pro
        195                 200                 205 gac aag tgg aaa tct cac agc agc ttc agc tgc ctg gtc acg cac gag    673
Asp Lys Trp Lys Ser His Ser Ser Phe Ser Cys Leu Val Thr His Glu
210                 215                 220 ggg agc acc gtg gag aag aag gtg gcc ccc gca gag tgc tct            715
Gly Ser Thr Val Glu Lys Lys Val Ala Pro Ala Glu Cys Ser
225                 230                 235 taggttcccg acggccccgc ccaccgaagg gggcccggag cctcaggacc tccaggagga  775
tcttgcctcc catctgggtc atcccgctct tctccccgca cccaggcagc actcaataaa  835
gtgttctttg ttcaatcaga aaaa                                         859

<210> SEQ ID NO 19
<211> LENGTH: 238
<212> TYPE: PRT
<213> ORGANISM: Canis familiaris

<400> SEQUENCE: 19

Thr Ser Asn Met Ala Trp Ser Pro Leu Leu Thr Leu Leu Ala Ser
1               5                   10                  15

Cys Thr Gly Ser Trp Ala Gln Ser Val Leu Thr Gln Pro Thr Ser Val
            20                  25                  30

Ser Gly Ser Leu Gly Gln Arg Val Thr Ile Ser Cys Ser Gly Ser Ser
        35                  40                  45

Thr Asn Ile Gly Ser Val Gly Ala Thr Trp Tyr Gln His Leu Pro Gly
    50                  55                  60

Lys Ala Pro Arg Leu Leu Leu Tyr Thr His Gly Glu Arg Pro Ser Gly
65                  70                  75                  80

Ile Pro Asp Arg Phe Ser Gly Ser Glu Ser Ala Asn Ser Asp Thr Leu
                85                  90                  95

Thr Ile Thr Gly Leu Gln Ala Glu Asp Glu Ala Asp Tyr Tyr Cys Gln
            100                 105                 110

Ser Phe Asp Ser Thr Leu Glu Thr Ala Val Phe Gly Gly Gly Thr His
        115                 120                 125

Leu Thr Val Leu Gly Gln Pro Lys Ala Ser Pro Ser Val Thr Leu Phe
    130                 135                 140

Pro Pro Ser Ser Glu Glu Leu Gly Ala Asn Lys Ala Thr Leu Val Cys
```

```
145                 150                 155                 160
Leu Ile Ser Asp Phe Tyr Pro Ser Gly Val Thr Val Ala Trp Lys Ala
                165                 170                 175

Asp Gly Ser Pro Val Thr Gln Gly Val Glu Thr Thr Lys Pro Ser Lys
                180                 185                 190

Gln Ser Asn Asn Lys Tyr Ala Ala Ser Ser Tyr Leu Ser Leu Thr Pro
                195                 200                 205

Asp Lys Trp Lys Ser His Ser Ser Phe Ser Cys Leu Val Thr His Glu
        210                 215                 220

Gly Ser Thr Val Glu Lys Lys Val Ala Pro Ala Glu Cys Ser
225                 230                 235

<210> SEQ ID NO 20
<211> LENGTH: 875
<212> TYPE: DNA
<213> ORGANISM: Canis familiaris
<220> FEATURE:
<221> NAME/KEY: CDS
<222> LOCATION: (2)..(712)

<400> SEQUENCE: 20 c tcc aac atg gcc tgg tcc cct ctc ctc ctc aca ctc ctt gtt tac tgc     49
  Ser Asn Met Ala Trp Ser Pro Leu Leu Leu Thr Leu Leu Val Tyr Cys
    1               5                  10                  15 aca ggg tcc tgg gcc cag tct gta ctg act cat ccg acc tca gtg tcg     97
Thr Gly Ser Trp Ala Gln Ser Val Leu Thr His Pro Thr Ser Val Ser
                20                  25                  30 ggg tcc ctt ggc cag agg gtc acc att tcc tgc tcc gga agc acg aac    145
Gly Ser Leu Gly Gln Arg Val Thr Ile Ser Cys Ser Gly Ser Thr Asn
        35                  40                  45 aac atc ggt act gtt ggt gcg ggc tgg tac caa cag ttc cca gga aag    193
Asn Ile Gly Thr Val Gly Ala Gly Trp Tyr Gln Gln Phe Pro Gly Lys
    50                  55                  60 gcc cct aaa ctc ctc att tac agt gat ggg aat cga ccg tca ggg gtc    241
Ala Pro Lys Leu Leu Ile Tyr Ser Asp Gly Asn Arg Pro Ser Gly Val
65                  70                  75                  80 cct gac cgg ttt tcc ggc tcc aag tca ggc aac tca gcc acc ctg acc    289
Pro Asp Arg Phe Ser Gly Ser Lys Ser Gly Asn Ser Ala Thr Leu Thr
                85                  90                  95 atc att gga ctt cag gct gag gac gag gct gat tac tac tgt cag tct    337
Ile Ile Gly Leu Gln Ala Glu Asp Glu Ala Asp Tyr Tyr Cys Gln Ser
            100                 105                 110 gtt gat ccc acg ctt ggt ggt cat gtg ttc ggc gga ggc acc cat ctg    385
Val Asp Pro Thr Leu Gly Gly His Val Phe Gly Gly Gly Thr His Leu
        115                 120                 125 acc gtc ctc ggt cag ccc aag gcc tcc cct tcg gtc aca ctc ttc ccg    433
Thr Val Leu Gly Gln Pro Lys Ala Ser Pro Ser Val Thr Leu Phe Pro
    130                 135                 140 ccc tcc tct gag gag ctt ggc gcc aac aag gcc acc ctg gtg tgc ctc    481
Pro Ser Ser Glu Glu Leu Gly Ala Asn Lys Ala Thr Leu Val Cys Leu
145                 150                 155                 160 atc agc gac ttc tac ccc agc ggc gtg aca gtg gcc tgg aag gca gac    529
Ile Ser Asp Phe Tyr Pro Ser Gly Val Thr Val Ala Trp Lys Ala Asp
                165                 170                 175 ggc agc ccc atc acc cag ggt gtg gag acc acc aag ccc tcc aag cag    577
Gly Ser Pro Ile Thr Gln Gly Val Glu Thr Thr Lys Pro Ser Lys Gln
            180                 185                 190 agc aac aac aag tac gcg gcc agc agc tac ctg agc ctg acg cct gac    625
Ser Asn Asn Lys Tyr Ala Ala Ser Ser Tyr Leu Ser Leu Thr Pro Asp
        195                 200                 205
```

-continued

```
aag tgg aaa tct cac agc agc ttc agc tgc ctg gtc acg cac gag ggg      673
Lys Trp Lys Ser His Ser Ser Phe Ser Cys Leu Val Thr His Glu Gly
    210                 215                 220 agc acc gtg gag aag aag gtg gcc ccc gca gag tgc tct taggttcctg       722
Ser Thr Val Glu Lys Lys Val Ala Pro Ala Glu Cys Ser
225                 230                 235 atgtccccg cccaccaaag ggggctcaga gcctcaggac ctccaggagg atcttgcctc     782
ccatctgggt catcccagcc tttcccctta aacccaggca acattcaata aagtgttctt    842
tcttcaatca gaaaaaaaaa aaaaaaaaaa aaa                                 875
```

<210> SEQ ID NO 21
<211> LENGTH: 237
<212> TYPE: PRT
<213> ORGANISM: Canis familiaris

<400> SEQUENCE: 21

```
Ser Asn Met Ala Trp Ser Pro Leu Leu Leu Thr Leu Leu Val Tyr Cys
1               5                   10                  15

Thr Gly Ser Trp Ala Gln Ser Val Leu Thr His Pro Thr Ser Val Ser
                20                  25                  30

Gly Ser Leu Gly Gln Arg Val Thr Ile Ser Cys Ser Gly Ser Thr Asn
            35                  40                  45

Asn Ile Gly Thr Val Gly Ala Gly Trp Tyr Gln Gln Phe Pro Gly Lys
        50                  55                  60

Ala Pro Lys Leu Leu Ile Tyr Ser Asp Gly Asn Arg Pro Ser Gly Val
65                  70                  75                  80

Pro Asp Arg Phe Ser Gly Ser Lys Ser Gly Asn Ser Ala Thr Leu Thr
                85                  90                  95

Ile Ile Gly Leu Gln Ala Glu Asp Glu Ala Asp Tyr Tyr Cys Gln Ser
            100                 105                 110

Val Asp Pro Thr Leu Gly Gly His Val Phe Gly Gly Thr His Leu
        115                 120                 125

Thr Val Leu Gly Gln Pro Lys Ala Ser Pro Ser Val Thr Leu Phe Pro
130                 135                 140

Pro Ser Ser Glu Glu Leu Gly Ala Asn Lys Ala Thr Leu Val Cys Leu
145                 150                 155                 160

Ile Ser Asp Phe Tyr Pro Ser Gly Val Thr Val Ala Trp Lys Ala Asp
                165                 170                 175

Gly Ser Pro Ile Thr Gln Gly Val Glu Thr Thr Lys Pro Ser Lys Gln
            180                 185                 190

Ser Asn Asn Lys Tyr Ala Ala Ser Ser Tyr Leu Ser Leu Thr Pro Asp
        195                 200                 205

Lys Trp Lys Ser His Ser Ser Phe Ser Cys Leu Val Thr His Glu Gly
    210                 215                 220

Ser Thr Val Glu Lys Lys Val Ala Pro Ala Glu Cys Ser
225                 230                 235
```

<210> SEQ ID NO 22
<211> LENGTH: 862
<212> TYPE: DNA
<213> ORGANISM: Canis familiaris
<220> FEATURE:
<221> NAME/KEY: CDS
<222> LOCATION: (2)..(718)

<400> SEQUENCE: 22

```
           g atg atc ttc acc atg gcc tgg tcc cct ctc ctc ctc ggc ctc ctt gct        49
             Met Ile Phe Thr Met Ala Trp Ser Pro Leu Leu Leu Gly Leu Leu Ala
             1               5                   10                  15 cac tgc aca ggg tcc tgg gcc cag tct atg ctg act cag ccg gcc tca                    97
His Cys Thr Gly Ser Trp Ala Gln Ser Met Leu Thr Gln Pro Ala Ser
                20                  25                  30 gtg tct ggg tcc ctg ggc cag aag gtc acc atc tcc tgc act gga agc                    145
Val Ser Gly Ser Leu Gly Gln Lys Val Thr Ile Ser Cys Thr Gly Ser
            35                  40                  45 agc tcc aac atc ggt gct tat tat gtg agc tgg tac caa cag tcc cca                    193
Ser Ser Asn Ile Gly Ala Tyr Tyr Val Ser Trp Tyr Gln Gln Ser Pro
        50                  55                  60 gga aaa ggc cct aga acc gtc atc tat ggt gat aat tac cga cct tca                    241
Gly Lys Gly Pro Arg Thr Val Ile Tyr Gly Asp Asn Tyr Arg Pro Ser
65                  70                  75                  80 ggg gtc ccc gat cga ttc tct ggc tcc aag tca ggc agt tca gcc acc                    289
Gly Val Pro Asp Arg Phe Ser Gly Ser Lys Ser Gly Ser Ser Ala Thr
                85                  90                  95 ctg acc atc tct ggg ctc cag gct gag gac gag gct gaa tat tac tgc                    337
Leu Thr Ile Ser Gly Leu Gln Ala Glu Asp Glu Ala Glu Tyr Tyr Cys
                100                 105                 110 tta tca tgg gat aat agt ctc aga ggt ggt gtg ttc ggc gga ggc acc                    385
Leu Ser Trp Asp Asn Ser Leu Arg Gly Gly Val Phe Gly Gly Gly Thr
            115                 120                 125 cac ctg acc gtc ctc ggt cag ccc aag gcc tcc ccc tcg gtc aca ctc                    433
His Leu Thr Val Leu Gly Gln Pro Lys Ala Ser Pro Ser Val Thr Leu
        130                 135                 140 ttc ccg ccc tcc tct gag gag ctc ggc gcc aac aag gcc acc ctg gtg                    481
Phe Pro Pro Ser Ser Glu Glu Leu Gly Ala Asn Lys Ala Thr Leu Val
145                 150                 155                 160 tgc ctc atc agc gac ttc tac ccc agc ggt gtg acg gtg gcc tgg aag                    529
Cys Leu Ile Ser Asp Phe Tyr Pro Ser Gly Val Thr Val Ala Trp Lys
                165                 170                 175 gca gac ggc agc ccc gtc acc cag ggc gtg gag acc acc aag ccc tcc                    577
Ala Asp Gly Ser Pro Val Thr Gln Gly Val Glu Thr Thr Lys Pro Ser
            180                 185                 190 aag cag agc aac aac aag tac gcg gcc agc agc tac ctg agc ctg acg                    625
Lys Gln Ser Asn Asn Lys Tyr Ala Ala Ser Ser Tyr Leu Ser Leu Thr
        195                 200                 205 cct gac aag tgg aaa tct cac agc agc ttc agc tgc ctg gtc acg cac                    673
Pro Asp Lys Trp Lys Ser His Ser Ser Phe Ser Cys Leu Val Thr His
            210                 215                 220 gag ggg agc acc gtg gag aag aag gtg gcc ccc gca gag tgc tct                        718
Glu Gly Ser Thr Val Glu Lys Lys Val Ala Pro Ala Glu Cys Ser
225                 230                 235 taggttcccg acggccccgc ccaccgaagg gggcccggag cctcaggacc tccaggagga                  778
tcttgcctcc catctgggtc atcccgctct tctccccgca cccaggcagc actcaataaa                  838
gtgttctttg ttcaatcaga aaaa                                                         862

<210> SEQ ID NO 23
<211> LENGTH: 239
<212> TYPE: PRT
<213> ORGANISM: Canis familiaris

<400> SEQUENCE: 23

Met Ile Phe Thr Met Ala Trp Ser Pro Leu Leu Leu Gly Leu Leu Ala
1               5                   10                  15

His Cys Thr Gly Ser Trp Ala Gln Ser Met Leu Thr Gln Pro Ala Ser
            20                  25                  30
```

Val Ser Gly Ser Leu Gly Gln Lys Val Thr Ile Ser Cys Thr Gly Ser
    35                  40                  45

Ser Ser Asn Ile Gly Ala Tyr Tyr Val Ser Trp Tyr Gln Gln Ser Pro
50                  55                  60

Gly Lys Gly Pro Arg Thr Val Ile Tyr Gly Asp Asn Tyr Arg Pro Ser
65                  70                  75                  80

Gly Val Pro Asp Arg Phe Ser Gly Ser Lys Ser Gly Ser Ser Ala Thr
                85                  90                  95

Leu Thr Ile Ser Gly Leu Gln Ala Glu Asp Glu Ala Glu Tyr Tyr Cys
            100                 105                 110

Leu Ser Trp Asp Asn Ser Leu Arg Gly Gly Val Phe Gly Gly Gly Thr
        115                 120                 125

His Leu Thr Val Leu Gly Gln Pro Lys Ala Ser Pro Ser Val Thr Leu
    130                 135                 140

Phe Pro Pro Ser Ser Glu Glu Leu Gly Ala Asn Lys Ala Thr Leu Val
145                 150                 155                 160

Cys Leu Ile Ser Asp Phe Tyr Pro Ser Gly Val Thr Val Ala Trp Lys
                165                 170                 175

Ala Asp Gly Ser Pro Val Thr Gln Gly Val Glu Thr Thr Lys Pro Ser
            180                 185                 190

Lys Gln Ser Asn Asn Lys Tyr Ala Ala Ser Ser Tyr Leu Ser Leu Thr
        195                 200                 205

Pro Asp Lys Trp Lys Ser His Ser Ser Phe Ser Cys Leu Val Thr His
    210                 215                 220

Glu Gly Ser Thr Val Glu Lys Lys Val Ala Pro Ala Glu Cys Ser
225                 230                 235

<210> SEQ ID NO 24
<211> LENGTH: 884
<212> TYPE: DNA
<213> ORGANISM: Canis familiaris
<220> FEATURE:
<221> NAME/KEY: CDS
<222> LOCATION: (2)..(733)

<400> SEQUENCE: 24

```
g aag aca gga tcc gtg atg acc tcc acc atg gga tgg ttc cct ctg ctc      49
  Lys Thr Gly Ser Val Met Thr Ser Thr Met Gly Trp Phe Pro Leu Leu
  1               5                   10                  15 ctc acc ctc ctg gct cac tgc aca ggt tcc tgg gcc cag tct gtg ctg       97
Leu Thr Leu Leu Ala His Cys Thr Gly Ser Trp Ala Gln Ser Val Leu
            20                  25                  30 act cag ccg gcc tca gtg tct ggg tcc ctg ggc cag agg gtc acc atc      145
Thr Gln Pro Ala Ser Val Ser Gly Ser Leu Gly Gln Arg Val Thr Ile
        35                  40                  45 tcc tgc act gga acc agc tcc aat atc ggt aca gat tat gtg ggc tgg      193
Ser Cys Thr Gly Thr Ser Ser Asn Ile Gly Thr Asp Tyr Val Gly Trp
    50                  55                  60 tac caa cag ctc cca gga aga ggc ccc aga acc ctc atc tct gat act      241
Tyr Gln Gln Leu Pro Gly Arg Gly Pro Arg Thr Leu Ile Ser Asp Thr
65                  70                  75                  80 agt cgc cga ccc tcg ggg gtc cct gat cga ttc tct ggc tcc agg tca      289
Ser Arg Arg Pro Ser Gly Val Pro Asp Arg Phe Ser Gly Ser Arg Ser
                85                  90                  95 ggc acc aca gca atc ctg act atc tct ggg ctc cag gct gag gac gag      337
Gly Thr Thr Ala Ile Leu Thr Ile Ser Gly Leu Gln Ala Glu Asp Glu
            100                 105                 110
```

|  |  |
|---|---|
| gct gat tat tac tgc tca gca tat gac agc agt ctc ggt gga act atc<br>Ala Asp Tyr Tyr Cys Ser Ala Tyr Asp Ser Ser Leu Gly Gly Thr Ile<br>115                 120                 125 | 385 |
| ttc ggc gga ggc act ttc ctg acc gtc ctc ggt cag ccc aag gcc tcc<br>Phe Gly Gly Gly Thr Phe Leu Thr Val Leu Gly Gln Pro Lys Ala Ser<br>130                 135                 140 | 433 |
| ccc tcg gtc aca ctc ttc ccg ccc tcc tct gag gag ctc ggc gcc aac<br>Pro Ser Val Thr Leu Phe Pro Pro Ser Ser Glu Glu Leu Gly Ala Asn<br>145                 150                 155                 160 | 481 |
| aag gcc acc ctg gtg tgc ctc atc agc gac ttc tac ccc agc ggc gtg<br>Lys Ala Thr Leu Val Cys Leu Ile Ser Asp Phe Tyr Pro Ser Gly Val<br>                165                 170                 175 | 529 |
| acg gtg gcc tgg aag gca gac ggc agc ccc gtc acc cag ggc gtg gag<br>Thr Val Ala Trp Lys Ala Asp Gly Ser Pro Val Thr Gln Gly Val Glu<br>                180                 185                 190 | 577 |
| acc acc aag ccc tcc aag cag agc aac aac aag tac gcg gcc agc agc<br>Thr Thr Lys Pro Ser Lys Gln Ser Asn Asn Lys Tyr Ala Ala Ser Ser<br>    195                 200                 205 | 625 |
| tac ctg agc ctg acg cct gac aag tgg aaa tct cac agc agc ttc agc<br>Tyr Leu Ser Leu Thr Pro Asp Lys Trp Lys Ser His Ser Ser Phe Ser<br>210                 215                 220 | 673 |
| tgc ctg gtc acg cac gag ggg agc acc gtg gag aag aag gtg gcc ccc<br>Cys Leu Val Thr His Glu Gly Ser Thr Val Glu Lys Lys Val Ala Pro<br>225                 230                 235                 240 | 721 |
| gca gag tgc tct taggttcccg acggccccgc ccaccgaagg gggcccggag<br>Ala Glu Cys Ser | 773 |
| cctcaggacc tccaggagga tcttgcctcc catctgggtc atcccgccct tctccccgca | 833 |
| cccaggcagc actcaataaa gtgttctttg ttcaatcaaa aaaaaaaaa a | 884 |

<210> SEQ ID NO 25
<211> LENGTH: 244
<212> TYPE: PRT
<213> ORGANISM: Canis familiaris

<400> SEQUENCE: 25

Lys Thr Gly Ser Val Met Thr Ser Thr Met Gly Trp Phe Pro Leu Leu
1               5                   10                  15

Leu Thr Leu Leu Ala His Cys Thr Gly Ser Trp Ala Gln Ser Val Leu
                20                  25                  30

Thr Gln Pro Ala Ser Val Ser Gly Ser Leu Gly Gln Arg Val Thr Ile
            35                  40                  45

Ser Cys Thr Gly Thr Ser Ser Asn Ile Gly Thr Asp Tyr Val Gly Trp
        50                  55                  60

Tyr Gln Gln Leu Pro Gly Arg Gly Pro Arg Thr Leu Ile Ser Asp Thr
65                  70                  75                  80

Ser Arg Arg Pro Ser Gly Val Pro Asp Arg Phe Ser Gly Ser Arg Ser
                85                  90                  95

Gly Thr Thr Ala Ile Leu Thr Ile Ser Gly Leu Gln Ala Glu Asp Glu
            100                 105                 110

Ala Asp Tyr Tyr Cys Ser Ala Tyr Asp Ser Ser Leu Gly Gly Thr Ile
        115                 120                 125

Phe Gly Gly Gly Thr Phe Leu Thr Val Leu Gly Gln Pro Lys Ala Ser
    130                 135                 140

Pro Ser Val Thr Leu Phe Pro Pro Ser Ser Glu Glu Leu Gly Ala Asn
145                 150                 155                 160

Lys Ala Thr Leu Val Cys Leu Ile Ser Asp Phe Tyr Pro Ser Gly Val
                165                 170                 175

```
Thr Val Ala Trp Lys Ala Asp Gly Ser Pro Val Thr Gln Gly Val Glu
                180                 185                 190

Thr Thr Lys Pro Ser Lys Gln Ser Asn Asn Lys Tyr Ala Ala Ser Ser
            195                 200                 205

Tyr Leu Ser Leu Thr Pro Asp Lys Trp Lys Ser His Ser Ser Phe Ser
        210                 215                 220

Cys Leu Val Thr His Glu Gly Ser Thr Val Glu Lys Lys Val Ala Pro
225                 230                 235                 240

Ala Glu Cys Ser

<210> SEQ ID NO 26
<211> LENGTH: 729
<212> TYPE: DNA
<213> ORGANISM: Canis familiaris
<220> FEATURE:
<221> NAME/KEY: CDS
<222> LOCATION: (2)..(571)

<400> SEQUENCE: 26
```

| | | | | | | | | | | | | | | | | |
|---|---|---|---|---|---|---|---|---|---|---|---|---|---|---|---|---|
| c | tcc | aac | att | gga | ggt | aat | cat | gta | ggt | tgg | tac | caa | caa | ttt | cca | gga | 49 |
|   | Ser | Asn | Ile | Gly | Gly | Asn | His | Val | Gly | Trp | Tyr | Gln | Gln | Phe | Pro | Gly |
|   | 1   |     |     | 5   |     |     |     |     | 10  |     |     |     |     | 15  |     |     |

```
aga ggc ccc aga act gtc atc tat agc aca aat gtt cga ccc tcg ggg          97
Arg Gly Pro Arg Thr Val Ile Tyr Ser Thr Asn Val Arg Pro Ser Gly
            20                  25                  30 gtg ccc gat cga ttc tct ggc tcc aag tct gac aac aca ggc acc ctg         145
Val Pro Asp Arg Phe Ser Gly Ser Lys Ser Asp Asn Thr Gly Thr Leu
 35                  40                  45 acc atc tct gga ctc cag gct gag gat gag gct gat tat tat tgc gca         193
Thr Ile Ser Gly Leu Gln Ala Glu Asp Glu Ala Asp Tyr Tyr Cys Ala
 50                  55                  60 acg tgg gat gat agt ctc agt gtt tct ctg ttc ggc gga ggc acc cac         241
Thr Trp Asp Asp Ser Leu Ser Val Ser Leu Phe Gly Gly Gly Thr His
65                  70                  75                  80 ctg acc gtc ctc ggt cag ccc aag gcc tcc ccc tcg gtc aca ctc ttc         289
Leu Thr Val Leu Gly Gln Pro Lys Ala Ser Pro Ser Val Thr Leu Phe
                85                  90                  95 ccg ccc tcc tct gag gag ctc ggc gcc aac aag gcc acc ctg gtg tgc         337
Pro Pro Ser Ser Glu Glu Leu Gly Ala Asn Lys Ala Thr Leu Val Cys
            100                 105                 110 ctc atc agc gac ttc tac ccc agc ggc gtg acg gtg gcc tgg aag gca         385
Leu Ile Ser Asp Phe Tyr Pro Ser Gly Val Thr Val Ala Trp Lys Ala
        115                 120                 125 gac ggc agc ccc gtc acc cag ggc gtg gag acc acc aag ccc tcc aag         433
Asp Gly Ser Pro Val Thr Gln Gly Val Glu Thr Thr Lys Pro Ser Lys
130                 135                 140 cag acc aac aac aag tac gcg gcc agc agc tac ctg agc ctg acg cct         481
Gln Thr Asn Asn Lys Tyr Ala Ala Ser Ser Tyr Leu Ser Leu Thr Pro
145                 150                 155                 160 gac aag tgg aaa tct cac agc agc ttc agc tgc ctg gtc acg cac gag         529
Asp Lys Trp Lys Ser His Ser Ser Phe Ser Cys Leu Val Thr His Glu
                165                 170                 175 ggg agc acc gtg gag aag aag gtg gcc ccc gca gag tgc tct                 571
Gly Ser Thr Val Glu Lys Lys Val Ala Pro Ala Glu Cys Ser
            180                 185                 190 taggttccog acggccccgc ccaccgaagg gggcccggag cctcaggacc tccaggagga       631
tcttgcctcc catctgggtc atcccgccct tctccccgca cccaggcagc actcaataaa       691
gtgttctttg ttcaatcaga aaaaaaaaaa aaaaaaa                                729
```

<210> SEQ ID NO 27
<211> LENGTH: 190
<212> TYPE: PRT
<213> ORGANISM: Canis familiaris

<400> SEQUENCE: 27

```
Ser Asn Ile Gly Gly Asn His Val Gly Trp Tyr Gln Gln Phe Pro Gly
1               5                   10                  15

Arg Gly Pro Arg Thr Val Ile Tyr Ser Thr Asn Val Arg Pro Ser Gly
            20                  25                  30

Val Pro Asp Arg Phe Ser Gly Ser Lys Ser Asp Asn Thr Gly Thr Leu
        35                  40                  45

Thr Ile Ser Gly Leu Gln Ala Glu Asp Glu Ala Asp Tyr Tyr Cys Ala
    50                  55                  60

Thr Trp Asp Asp Ser Leu Ser Val Ser Leu Phe Gly Gly Thr His
65                  70                  75                  80

Leu Thr Val Leu Gly Gln Pro Lys Ala Ser Pro Ser Val Thr Leu Phe
                85                  90                  95

Pro Pro Ser Ser Glu Glu Leu Gly Ala Asn Lys Ala Thr Leu Val Cys
            100                 105                 110

Leu Ile Ser Asp Phe Tyr Pro Ser Gly Val Thr Val Ala Trp Lys Ala
        115                 120                 125

Asp Gly Ser Pro Val Thr Gln Gly Val Glu Thr Thr Lys Pro Ser Lys
    130                 135                 140

Gln Thr Asn Asn Lys Tyr Ala Ala Ser Ser Tyr Leu Ser Leu Thr Pro
145                 150                 155                 160

Asp Lys Trp Lys Ser His Ser Ser Phe Ser Cys Leu Val Thr His Glu
                165                 170                 175

Gly Ser Thr Val Glu Lys Lys Val Ala Pro Ala Glu Cys Ser
            180                 185                 190
```

<210> SEQ ID NO 28
<211> LENGTH: 1176
<212> TYPE: DNA
<213> ORGANISM: Canis familiaris
<220> FEATURE:
<221> NAME/KEY: CDS
<222> LOCATION: (2)..(727)

<400> SEQUENCE: 28

```
a gga tcc gtg atg acc tcc acc atg ggc tgg tcc cct ctc atc ctc acc      49
  Gly Ser Val Met Thr Ser Thr Met Gly Trp Ser Pro Leu Ile Leu Thr
  1               5                   10                  15 ctc ttc gct cac tgc gca ggg tcc tgg gcc cag tct gtc ctg act cag        97
Leu Phe Ala His Cys Ala Gly Ser Trp Ala Gln Ser Val Leu Thr Gln
            20                  25                  30 ccg gcc tca gtg tct ggg tcc ctg ggc cag agg gtc acc atc tcc tgc        145
Pro Ala Ser Val Ser Gly Ser Leu Gly Gln Arg Val Thr Ile Ser Cys
        35                  40                  45 act gga agc agc tcc aat gtt ggt ttt ggc gat tat gtg ggc tgg tac        193
Thr Gly Ser Ser Ser Asn Val Gly Phe Gly Asp Tyr Val Gly Trp Tyr
    50                  55                  60 cag cag ctc cca gga aga ggc ccc aga acc ctc ttc tac cgt gct act        241
Gln Gln Leu Pro Gly Arg Gly Pro Arg Thr Leu Phe Tyr Arg Ala Thr
65                  70                  75                  80 ggc cga ccc tcg ggg gtc cct gat cga ttc tct gcc tcc agg tca ggc        289
Gly Arg Pro Ser Gly Val Pro Asp Arg Phe Ser Ala Ser Arg Ser Gly
                85                  90                  95
```

| | | | | | | | | | | | | | | | |
|---|---|---|---|---|---|---|---|---|---|---|---|---|---|---|---|
| acc | aca | gcg | acc | ctg | acc | atc | tct | gga | ctc | cag | cct | gag | gat | gaa | gcc | 337
| Thr | Thr | Ala | Thr | Leu | Thr | Ile | Ser | Gly | Leu | Gln | Pro | Glu | Asp | Glu | Ala |
| | | | 100 | | | | | 105 | | | | | 110 | | |

```
acc aca gcg acc ctg acc atc tct gga ctc cag cct gag gat gaa gcc      337
Thr Thr Ala Thr Leu Thr Ile Ser Gly Leu Gln Pro Glu Asp Glu Ala
            100                 105                 110 gat tat tac tgc tca tcc tat gac tct act ctc ttt tct gtg ttc ggc      385
Asp Tyr Tyr Cys Ser Ser Tyr Asp Ser Thr Leu Phe Ser Val Phe Gly
        115                 120                 125 gga ggc acc tac ctg acc gtc ctc ggt cag ccc aag gcc tcc ccc tcg      433
Gly Gly Thr Tyr Leu Thr Val Leu Gly Gln Pro Lys Ala Ser Pro Ser
130                 135                 140 gtc aca ctc ttc ccg ccc tcc tct gag gag ctc ggc gcc aac aag gcc      481
Val Thr Leu Phe Pro Pro Ser Ser Glu Glu Leu Gly Ala Asn Lys Ala
145                 150                 155                 160 acc ctg gtg tgc ctc atc agc gac ttc tac ccc agc ggc gtg acg gtg      529
Thr Leu Val Cys Leu Ile Ser Asp Phe Tyr Pro Ser Gly Val Thr Val
                165                 170                 175 gcc tgg aag gca gac ggc agc ccc gtc acc cag ggc gtg gag acc acc      577
Ala Trp Lys Ala Asp Gly Ser Pro Val Thr Gln Gly Val Glu Thr Thr
                180                 185                 190 aag ccc tcc aag cag agc aac aac aag tac gcg gcc agc agc tac ctg      625
Lys Pro Ser Lys Gln Ser Asn Asn Lys Tyr Ala Ala Ser Ser Tyr Leu
        195                 200                 205 agc ctg acg cct gac aag tgg aaa tct cac agc agc ttc agc tgc ctg      673
Ser Leu Thr Pro Asp Lys Trp Lys Ser His Ser Ser Phe Ser Cys Leu
210                 215                 220 gtc acg cac gag ggg agc acc gtg gag aag aag gtg gcc ccc gca gag      721
Val Thr His Glu Gly Ser Thr Val Glu Lys Lys Val Ala Pro Ala Glu
225                 230                 235                 240 tgc tct taggttccog acggccccgc ccaccgaagg gggcccggag cctcaggacc      777
Cys Ser tccaggagga tcttgcctcc catctgggtc atcccgccct tctccccgca cccaggcagc      837
actcaataaa gtgttccaat ttcaagcgac ttaaatgcat atggttttt ttttttgatg      897 tgatacagct gtgtttactt caacctccag ggaatcctaa gggcccagag actccccttg      957
tgctgtaaga ttgtgtccct gaaacaagtc acctccagcc ttccagaggg gtgggctgcc     1017
tggaggcagt ggcacgggcc tgggctctct agaatgtgta ctgagcaggg gcaggaggcc     1077
caaagggcca cccatgcctc caggagcctc cgcaggaggg agcagagtct gtagaggctc     1137
acggagaggc tggaagatca ctggaacagc agcaagcca                            1176
```

<210> SEQ ID NO 29
<211> LENGTH: 242
<212> TYPE: PRT
<213> ORGANISM: Canis familiaris

<400> SEQUENCE: 29

```
Gly Ser Val Met Thr Ser Thr Met Gly Trp Ser Pro Leu Ile Leu Thr
1               5                   10                  15

Leu Phe Ala His Cys Ala Gly Ser Trp Ala Gln Ser Val Leu Thr Gln
                20                  25                  30

Pro Ala Ser Val Ser Gly Ser Leu Gly Gln Arg Val Thr Ile Ser Cys
            35                  40                  45

Thr Gly Ser Ser Ser Asn Val Gly Phe Gly Asp Tyr Val Gly Trp Tyr
        50                  55                  60

Gln Gln Leu Pro Gly Arg Gly Pro Arg Thr Leu Phe Tyr Arg Ala Thr
65                  70                  75                  80

Gly Arg Pro Ser Gly Val Pro Asp Arg Phe Ser Ala Ser Arg Ser Gly
                85                  90                  95
```

```
Thr Thr Ala Thr Leu Thr Ile Ser Gly Leu Gln Pro Glu Asp Glu Ala
            100                 105                 110

Asp Tyr Tyr Cys Ser Ser Tyr Asp Ser Thr Leu Phe Ser Val Phe Gly
        115                 120                 125

Gly Gly Thr Tyr Leu Thr Val Leu Gly Gln Pro Lys Ala Ser Pro Ser
    130                 135                 140

Val Thr Leu Phe Pro Pro Ser Ser Glu Glu Leu Gly Ala Asn Lys Ala
145                 150                 155                 160

Thr Leu Val Cys Leu Ile Ser Asp Phe Tyr Pro Ser Gly Val Thr Val
                165                 170                 175

Ala Trp Lys Ala Asp Gly Ser Pro Val Thr Gln Gly Val Glu Thr Thr
            180                 185                 190

Lys Pro Ser Lys Gln Ser Asn Asn Lys Tyr Ala Ala Ser Ser Tyr Leu
        195                 200                 205

Ser Leu Thr Pro Asp Lys Trp Lys Ser His Ser Ser Phe Ser Cys Leu
    210                 215                 220

Val Thr His Glu Gly Ser Thr Val Glu Lys Val Ala Pro Ala Glu
225                 230                 235                 240

Cys Ser

<210> SEQ ID NO 30
<211> LENGTH: 762
<212> TYPE: DNA
<213> ORGANISM: Canis familiaris
<220> FEATURE:
<221> NAME/KEY: CDS
<222> LOCATION: (1)..(606)

<400> SEQUENCE: 30 ggc cag agg gtc acc atc tcc tgc act gga agc ccc aat gtt ggt tat     48
Gly Gln Arg Val Thr Ile Ser Cys Thr Gly Ser Pro Asn Val Gly Tyr
1               5                   10                  15 ggc aat tac gtg ggc tgg tac cag cag ctc cca gga aca ggc ccc aga    96
Gly Asn Tyr Val Gly Trp Tyr Gln Gln Leu Pro Gly Thr Gly Pro Arg
            20                  25                  30 acc ctc att tat ggt aag aat cac cga ccc gcg ggg gtc cct gat cga   144
Thr Leu Ile Tyr Gly Lys Asn His Arg Pro Ala Gly Val Pro Asp Arg
        35                  40                  45 ttc tct ggc tcc act tca ggc agt tca gcc aca ctg acc atc tct ggg   192
Phe Ser Gly Ser Thr Ser Gly Ser Ser Ala Thr Leu Thr Ile Ser Gly
    50                  55                  60 ctc cag gct gag gat gaa gca gat tat tac tgc tca tcc tat gac atc   240
Leu Gln Ala Glu Asp Glu Ala Asp Tyr Tyr Cys Ser Ser Tyr Asp Ile
65                  70                  75                  80 agt ctc ggt ggt gtt gtg ttc ggc gga ggc acc cat ctg acc gtc ctc   288
Ser Leu Gly Gly Val Val Phe Gly Gly Gly Thr His Leu Thr Val Leu
                85                  90                  95 ggt cag ccc aag gcc tcc ccc tcg gtc aca ctc ttc ccg ccc tcc tct   336
Gly Gln Pro Lys Ala Ser Pro Ser Val Thr Leu Phe Pro Pro Ser Ser
            100                 105                 110 gag gag ctc ggc gcc aac aag gcc acc ctg gtg tgc ctc atc agc gac   384
Glu Glu Leu Gly Ala Asn Lys Ala Thr Leu Val Cys Leu Ile Ser Asp
        115                 120                 125 ttc tac ccc agt ggc gtg acg gtg gcc tgg aag gca gac ggc agc ccc   432
Phe Tyr Pro Ser Gly Val Thr Val Ala Trp Lys Ala Asp Gly Ser Pro
    130                 135                 140 gtc acc cag ggc gtg gag acc acc aag ccc tcc aag cag agc aac aac   480
Val Thr Gln Gly Val Glu Thr Thr Lys Pro Ser Lys Gln Ser Asn Asn
```

| aag tac gcg gcc agc agc tac ctg agc ctg acg cct gac aag tgg aaa | 528 |
|---|---|
| Lys Tyr Ala Ala Ser Ser Tyr Leu Ser Leu Thr Pro Asp Lys Trp Lys | |
| 165 170 175 | |

| tct cac agc agc ttc agc tgc ctg gtc aca cac gag ggg agc acc gtg | 576 |
|---|---|
| Ser His Ser Ser Phe Ser Cys Leu Val Thr His Glu Gly Ser Thr Val | |
| 180 185 190 | |

| gag aag aag gtg gcc ccc gca gag tgc tct taggttccccg acgcccccgc | 626 |
|---|---|
| Glu Lys Lys Val Ala Pro Ala Glu Cys Ser | |
| 195 200 | | ccacctaagg gggcccggag cctcaggacc tccaggagga tcttgcctcc tatctgggtc    686 atcccgccct tctccccaca cccaggcagc actcaataaa gtgttctttg ttcaatcaga    746 aaaaaaaaaa aaaaaa    762

```
<210> SEQ ID NO 31
<211> LENGTH: 202
<212> TYPE: PRT
<213> ORGANISM: Canis familiaris

<400> SEQUENCE: 31
```

Gly Gln Arg Val Thr Ile Ser Cys Thr Gly Ser Pro Asn Val Gly Tyr
1               5                   10                  15

Gly Asn Tyr Val Gly Trp Tyr Gln Gln Leu Pro Gly Thr Gly Pro Arg
            20                  25                  30

Thr Leu Ile Tyr Gly Lys Asn His Arg Pro Ala Gly Val Pro Asp Arg
        35                  40                  45

Phe Ser Gly Ser Thr Ser Gly Ser Ser Ala Thr Leu Thr Ile Ser Gly
    50                  55                  60

Leu Gln Ala Glu Asp Glu Ala Asp Tyr Tyr Cys Ser Ser Tyr Asp Ile
65                  70                  75                  80

Ser Leu Gly Gly Val Val Phe Gly Gly Gly Thr His Leu Thr Val Leu
                85                  90                  95

Gly Gln Pro Lys Ala Ser Pro Ser Val Thr Leu Phe Pro Pro Ser Ser
            100                 105                 110

Glu Glu Leu Gly Ala Asn Lys Ala Thr Leu Val Cys Leu Ile Ser Asp
        115                 120                 125

Phe Tyr Pro Ser Gly Val Thr Val Ala Trp Lys Ala Asp Gly Ser Pro
    130                 135                 140

Val Thr Gln Gly Val Glu Thr Thr Lys Pro Ser Lys Gln Ser Asn Asn
145                 150                 155                 160

Lys Tyr Ala Ala Ser Ser Tyr Leu Ser Leu Thr Pro Asp Lys Trp Lys
                165                 170                 175

Ser His Ser Ser Phe Ser Cys Leu Val Thr His Glu Gly Ser Thr Val
            180                 185                 190

Glu Lys Lys Val Ala Pro Ala Glu Cys Ser
        195                 200

```
<210> SEQ ID NO 32
<211> LENGTH: 826
<212> TYPE: DNA
<213> ORGANISM: Canis familiaris
<220> FEATURE:
<221> NAME/KEY: CDS
<222> LOCATION: (1)..(675)

<400> SEQUENCE: 32
```

| ctt gtc agc ctc ctg gct ctc tgc aca ggt tct gtg gcc tcc tat gtg | 48 |
|---|---|

```
Leu Val Ser Leu Leu Ala Leu Cys Thr Gly Ser Val Ala Ser Tyr Val
1               5                   10                  15 ctg aca cag ccg ccg tcc atg agt gtg acc ctg agg cag acg gcc cgc      96
Leu Thr Gln Pro Pro Ser Met Ser Val Thr Leu Arg Gln Thr Ala Arg
            20                  25                  30 atc acc tgt gag gga gac agc att gga gat aaa aga gtt tac tgg tac     144
Ile Thr Cys Glu Gly Asp Ser Ile Gly Asp Lys Arg Val Tyr Trp Tyr
                35                  40                  45 cag cag aaa ctg ggc cgg ggc ccg atg ttg att att tat gat ggt acc     192
Gln Gln Lys Leu Gly Arg Gly Pro Met Leu Ile Ile Tyr Asp Gly Thr
        50                  55                  60 tac agg ccg tca ggg atc cct gac cga ttc ttc ggc gcc aat tcg ggg     240
Tyr Arg Pro Ser Gly Ile Pro Asp Arg Phe Phe Gly Ala Asn Ser Gly
65                  70                  75                  80 agc aca gcc acc ctg acc atc agc ggg gcc ctg gcc gag gac gag gct     288
Ser Thr Ala Thr Leu Thr Ile Ser Gly Ala Leu Ala Glu Asp Glu Ala
                85                  90                  95 gac tat tac tgc cag gtg tgg gac aat ggt gaa att att ttc ggc gga     336
Asp Tyr Tyr Cys Gln Val Trp Asp Asn Gly Glu Ile Ile Phe Gly Gly
            100                 105                 110 ggc acc cgt ctg acc gtc ctc ggt cag ccc aag gcc tcc cct tcg gtc     384
Gly Thr Arg Leu Thr Val Leu Gly Gln Pro Lys Ala Ser Pro Ser Val
        115                 120                 125 aca ctc ttc ccg ccc tcc tct gag gag ctt ggc gcc aac aag gcc acc     432
Thr Leu Phe Pro Pro Ser Ser Glu Glu Leu Gly Ala Asn Lys Ala Thr
130                 135                 140 ctg gtg tgc ctc atc agc gac ttc tac ccc agc ggc gtg aca gtg gcc     480
Leu Val Cys Leu Ile Ser Asp Phe Tyr Pro Ser Gly Val Thr Val Ala
                145                 150                 155                 160 tgg aag gca gac ggc agc ccc atc acc cag ggt gtg gag acc acc aag     528
Trp Lys Ala Asp Gly Ser Pro Ile Thr Gln Gly Val Glu Thr Thr Lys
                165                 170                 175 ccc tcc aag cag agc aac aac aag tac gcg gcc agc agc tac ctg agc     576
Pro Ser Lys Gln Ser Asn Asn Lys Tyr Ala Ala Ser Ser Tyr Leu Ser
        180                 185                 190 ctg acg cct gac aag tgg aaa tct cac agc agc ttc agc tgc ctg gtc     624
Leu Thr Pro Asp Lys Trp Lys Ser His Ser Ser Phe Ser Cys Leu Val
    195                 200                 205 acg cac gag ggg agc acc gtg gag aag aag gtg gcc ccc gca gag tgc     672
Thr His Glu Gly Ser Thr Val Glu Lys Lys Val Ala Pro Ala Glu Cys
    210                 215                 220 tct taggttcctg atgtccccg cccaccaaag ggggctcaga gcctcaggac            725
Ser
225 ctccaggagg atcttgcctc ccatctgggt catcccagcc tttcccctta aacccaggca    785 acattcaata aagtgttctt tcttcaatca gaagggccc g                         826

<210> SEQ ID NO 33
<211> LENGTH: 225
<212> TYPE: PRT
<213> ORGANISM: Canis familiaris

<400> SEQUENCE: 33

Leu Val Ser Leu Leu Ala Leu Cys Thr Gly Ser Val Ala Ser Tyr Val
1               5                   10                  15

Leu Thr Gln Pro Pro Ser Met Ser Val Thr Leu Arg Gln Thr Ala Arg
            20                  25                  30

Ile Thr Cys Glu Gly Asp Ser Ile Gly Asp Lys Arg Val Tyr Trp Tyr
                35                  40                  45
```

```
Gln Gln Lys Leu Gly Arg Gly Pro Met Leu Ile Ile Tyr Asp Gly Thr
    50                  55                  60

Tyr Arg Pro Ser Gly Ile Pro Asp Arg Phe Phe Gly Ala Asn Ser Gly
65                  70                  75                  80

Ser Thr Ala Thr Leu Thr Ile Ser Gly Ala Leu Ala Glu Asp Glu Ala
                85                  90                  95

Asp Tyr Tyr Cys Gln Val Trp Asp Asn Gly Glu Ile Ile Phe Gly Gly
            100                 105                 110

Gly Thr Arg Leu Thr Val Leu Gly Gln Pro Lys Ala Ser Pro Ser Val
        115                 120                 125

Thr Leu Phe Pro Pro Ser Ser Glu Glu Leu Gly Ala Asn Lys Ala Thr
    130                 135                 140

Leu Val Cys Leu Ile Ser Asp Phe Tyr Pro Ser Gly Val Thr Val Ala
145                 150                 155                 160

Trp Lys Ala Asp Gly Ser Pro Ile Thr Gln Gly Val Glu Thr Lys
                165                 170                 175

Pro Ser Lys Gln Ser Asn Asn Lys Tyr Ala Ala Ser Ser Tyr Leu Ser
            180                 185                 190

Leu Thr Pro Asp Lys Trp Lys Ser His Ser Ser Phe Ser Cys Leu Val
        195                 200                 205

Thr His Glu Gly Ser Thr Val Glu Lys Lys Val Ala Pro Ala Glu Cys
    210                 215                 220

Ser
225

<210> SEQ ID NO 34
<211> LENGTH: 796
<212> TYPE: DNA
<213> ORGANISM: Canis familiaris
<220> FEATURE:
<221> NAME/KEY: CDS
<222> LOCATION: (2)..(640)

<400> SEQUENCE: 34 g ctg act cag ccg gcc tca gtg tct ggg tcc ctg ggc cag agg gtc acc     49
  Leu Thr Gln Pro Ala Ser Val Ser Gly Ser Leu Gly Gln Arg Val Thr
  1               5                  10                  15 atc tcc tgc act gga agc agt tcc aac att gga agt aat gat gtg ggt     97
Ile Ser Cys Thr Gly Ser Ser Ser Asn Ile Gly Ser Asn Asp Val Gly
            20                  25                  30 tgg tac cag cag ctc cca gga aga ggc ccc aaa act gtc gtc tct aat    145
Trp Tyr Gln Gln Leu Pro Gly Arg Gly Pro Lys Thr Val Val Ser Asn
        35                  40                  45 aca aat att cgg ccc tcg ggg gtg ccc gat cga ttc tct gcc tcc aag    193
Thr Asn Ile Arg Pro Ser Gly Val Pro Asp Arg Phe Ser Ala Ser Lys
    50                  55                  60 tct ggc agc aca gcc acc ctg acc atc tct ggc ctc cag gct gag gat    241
Ser Gly Ser Thr Ala Thr Leu Thr Ile Ser Gly Leu Gln Ala Glu Asp
65                  70                  75                  80 gag gct gat tat tac tgc tca acg tgg gat aat agt ctc agt act tac    289
Glu Ala Asp Tyr Tyr Cys Ser Thr Trp Asp Asn Ser Leu Ser Thr Tyr
                85                  90                  95 atg ttc ggc tct gga acc caa ctg acc gtc ctt ggt cag ccc aag gcc    337
Met Phe Gly Ser Gly Thr Gln Leu Thr Val Leu Gly Gln Pro Lys Ala
            100                 105                 110 tcc ccc tcg gtc aca ctc ttc ccg ccc tcc tct gag gag ctc ggc gcc    385
Ser Pro Ser Val Thr Leu Phe Pro Pro Ser Ser Glu Glu Leu Gly Ala
        115                 120                 125
```

```
aac aag gcc acc ctg gtg tgc ctc atc agc gac ttc tac ccc agc ggc    433
Asn Lys Ala Thr Leu Val Cys Leu Ile Ser Asp Phe Tyr Pro Ser Gly
    130                 135                 140 gtg acg gtg gcc tgg aag gca gac ggc agc ccc atc acc cag ggc gtg    481
Val Thr Val Ala Trp Lys Ala Asp Gly Ser Pro Ile Thr Gln Gly Val
145                 150                 155                 160 gag acc acc aag ccc tcc aag cag agc aac aac aag tac gcg gcc agc    529
Glu Thr Thr Lys Pro Ser Lys Gln Ser Asn Asn Lys Tyr Ala Ala Ser
                165                 170                 175 agc tac ctg agc ctg acg cct gac aag tgg aaa tct cac agc agc ttc    577
Ser Tyr Leu Ser Leu Thr Pro Asp Lys Trp Lys Ser His Ser Ser Phe
            180                 185                 190 agc tgc ctg gtc acg cac gag ggg agc act gtg gag aag aag gtg gcc    625
Ser Cys Leu Val Thr His Glu Gly Ser Thr Val Glu Lys Lys Val Ala
        195                 200                 205 ccc gca gag tgc tct taggttccg atgccccccg cccaccgaag ggggctcgga    680
Pro Ala Glu Cys Ser
    210 gcctcaggac ctccaggagg atcttgcctc ccatctgggt cttcccagcc cttttcccca    740 cactcaggca acactcaata aagtgtcctt tattcaatca gaaaaaaaaa aaaaaa    796

<210> SEQ ID NO 35
<211> LENGTH: 213
<212> TYPE: PRT
<213> ORGANISM: Canis familiaris

<400> SEQUENCE: 35

Leu Thr Gln Pro Ala Ser Val Ser Gly Ser Leu Gly Gln Arg Val Thr
1               5                   10                  15

Ile Ser Cys Thr Gly Ser Ser Asn Ile Gly Ser Asn Asp Val Gly
            20                  25                  30

Trp Tyr Gln Gln Leu Pro Gly Arg Gly Pro Lys Thr Val Val Ser Asn
                35                  40                  45

Thr Asn Ile Arg Pro Ser Gly Val Pro Asp Arg Phe Ser Ala Ser Lys
        50                  55                  60

Ser Gly Ser Thr Ala Thr Leu Thr Ile Ser Gly Leu Gln Ala Glu Asp
65                  70                  75                  80

Glu Ala Asp Tyr Tyr Cys Ser Thr Trp Asp Asn Ser Leu Ser Thr Tyr
                85                  90                  95

Met Phe Gly Ser Gly Thr Gln Leu Thr Val Leu Gly Gln Pro Lys Ala
            100                 105                 110

Ser Pro Ser Val Thr Leu Phe Pro Pro Ser Ser Glu Glu Leu Gly Ala
        115                 120                 125

Asn Lys Ala Thr Leu Val Cys Leu Ile Ser Asp Phe Tyr Pro Ser Gly
    130                 135                 140

Val Thr Val Ala Trp Lys Ala Asp Gly Ser Pro Ile Thr Gln Gly Val
145                 150                 155                 160

Glu Thr Thr Lys Pro Ser Lys Gln Ser Asn Asn Lys Tyr Ala Ala Ser
                165                 170                 175

Ser Tyr Leu Ser Leu Thr Pro Asp Lys Trp Lys Ser His Ser Ser Phe
            180                 185                 190

Ser Cys Leu Val Thr His Glu Gly Ser Thr Val Glu Lys Lys Val Ala
        195                 200                 205

Pro Ala Glu Cys Ser
    210
```

<210> SEQ ID NO 36
<211> LENGTH: 930
<212> TYPE: DNA
<213> ORGANISM: Canis familiaris
<220> FEATURE:
<221> NAME/KEY: CDS
<222> LOCATION: (1)..(771)

<400> SEQUENCE: 36

```
atg aag agg gtg aga aat att gaa aag att ata ata aat cag gtg gat      48
Met Lys Arg Val Arg Asn Ile Glu Lys Ile Ile Ile Asn Gln Val Asp
1               5                   10                  15 gtg atg acc tcc acc atg ggc tgg ttc cct ctc atc ctc acc ctc ctc      96
Val Met Thr Ser Thr Met Gly Trp Phe Pro Leu Ile Leu Thr Leu Leu
            20                  25                  30 gct cac tgc gca ggg tcc tgg gcc cag tct gtg ctg act cag ccg gcc     144
Ala His Cys Ala Gly Ser Trp Ala Gln Ser Val Leu Thr Gln Pro Ala
        35                  40                  45 tca gtg tct ggg tcc ctg ggc cag agg gtc acc atc tcc tgc act gga     192
Ser Val Ser Gly Ser Leu Gly Gln Arg Val Thr Ile Ser Cys Thr Gly
    50                  55                  60 agc agc tcc aat gtt ggt tat ggc aat tat gtg ggc tgg tac cag cag     240
Ser Ser Ser Asn Val Gly Tyr Gly Asn Tyr Val Gly Trp Tyr Gln Gln
65                  70                  75                  80 ctc cca gga aca agc ccc aga aac ctc atc tat gat act agt agc cga     288
Leu Pro Gly Thr Ser Pro Arg Asn Leu Ile Tyr Asp Thr Ser Ser Arg
                85                  90                  95 ccc tcg ggg gtc cct gat cga ttc tct ggc tcc agg tca ggc agc aca     336
Pro Ser Gly Val Pro Asp Arg Phe Ser Gly Ser Arg Ser Gly Ser Thr
            100                 105                 110 gca acc ctg acc atc tct ggg ctc cag gct gag gat gaa gcc gat tat     384
Ala Thr Leu Thr Ile Ser Gly Leu Gln Ala Glu Asp Glu Ala Asp Tyr
        115                 120                 125 tac tgc tca tcc tat gac aga agt ctc agt ggt gct gtg ttc ggc gga     432
Tyr Cys Ser Ser Tyr Asp Arg Ser Leu Ser Gly Ala Val Phe Gly Gly
    130                 135                 140 ggc acc cac ctg acc gtc ctc ggt cag ccc aag gcc tcc ccc tcg gtc     480
Gly Thr His Leu Thr Val Leu Gly Gln Pro Lys Ala Ser Pro Ser Val
145                 150                 155                 160 aca ctc ttc ccg ccc tcc tct gag gag ctc ggc gcc aac aag gcc acc     528
Thr Leu Phe Pro Pro Ser Ser Glu Glu Leu Gly Ala Asn Lys Ala Thr
                165                 170                 175 ctg gtg tgc ctc atc agc gac ttc tac ccc agc ggc gtg acg gtg gcc     576
Leu Val Cys Leu Ile Ser Asp Phe Tyr Pro Ser Gly Val Thr Val Ala
            180                 185                 190 tgg aag gca gac ggc agc ccc gtc acc cag ggc gtg gag acc acc aag     624
Trp Lys Ala Asp Gly Ser Pro Val Thr Gln Gly Val Glu Thr Thr Lys
        195                 200                 205 ccc tcc aag cag agc aac aac aag tac gcg gcc agc agc tac ctg agc     672
Pro Ser Lys Gln Ser Asn Asn Lys Tyr Ala Ala Ser Ser Tyr Leu Ser
    210                 215                 220 ctg acg cct gac aag tgg aaa tct cac agc agc ttc agc tgc ctg gtc     720
Leu Thr Pro Asp Lys Trp Lys Ser His Ser Ser Phe Ser Cys Leu Val
225                 230                 235                 240 acg cac gag ggg agc acc gtg gag aag aag gtg gcc ccc gca gag tgc     768
Thr His Glu Gly Ser Thr Val Glu Lys Lys Val Ala Pro Ala Glu Cys
                245                 250                 255 tct taggttcccg acggcccgc ccaccgaagg gggcccggag cctcaggacc           821
Ser tccaggagga tcttgcctcc catctgggtc atcccgccct tctccccgca cccaggcagc   881
```

```
actcaataaa gtgttctttg ttcaatcaga aaaaaaaaaa aaaaaaaa          930
```

<210> SEQ ID NO 37
<211> LENGTH: 257
<212> TYPE: PRT
<213> ORGANISM: Canis familiaris

<400> SEQUENCE: 37

Met Lys Arg Val Arg Asn Ile Glu Lys Ile Ile Ile Asn Gln Val Asp
1               5                   10                  15

Val Met Thr Ser Thr Met Gly Trp Phe Pro Leu Ile Leu Thr Leu Leu
            20                  25                  30

Ala His Cys Ala Gly Ser Trp Ala Gln Ser Val Leu Thr Gln Pro Ala
        35                  40                  45

Ser Val Ser Gly Ser Leu Gly Gln Arg Val Thr Ile Ser Cys Thr Gly
    50                  55                  60

Ser Ser Ser Asn Val Gly Tyr Gly Asn Tyr Val Gly Trp Tyr Gln Gln
65                  70                  75                  80

Leu Pro Gly Thr Ser Pro Arg Asn Leu Ile Tyr Asp Thr Ser Ser Arg
                85                  90                  95

Pro Ser Gly Val Pro Asp Arg Phe Ser Gly Ser Arg Ser Gly Ser Thr
            100                 105                 110

Ala Thr Leu Thr Ile Ser Gly Leu Gln Ala Glu Asp Glu Ala Asp Tyr
        115                 120                 125

Tyr Cys Ser Ser Tyr Asp Arg Ser Leu Ser Gly Ala Val Phe Gly Gly
    130                 135                 140

Gly Thr His Leu Thr Val Leu Gly Gln Pro Lys Ala Ser Pro Ser Val
145                 150                 155                 160

Thr Leu Phe Pro Pro Ser Ser Glu Glu Leu Gly Ala Asn Lys Ala Thr
                165                 170                 175

Leu Val Cys Leu Ile Ser Asp Phe Tyr Pro Ser Gly Val Thr Val Ala
            180                 185                 190

Trp Lys Ala Asp Gly Ser Pro Val Thr Gln Gly Val Glu Thr Thr Lys
        195                 200                 205

Pro Ser Lys Gln Ser Asn Asn Lys Tyr Ala Ala Ser Ser Tyr Leu Ser
    210                 215                 220

Leu Thr Pro Asp Lys Trp Lys Ser His Ser Ser Phe Ser Cys Leu Val
225                 230                 235                 240

Thr His Glu Gly Ser Thr Val Glu Lys Lys Val Ala Pro Ala Glu Cys
                245                 250                 255

Ser

<210> SEQ ID NO 38
<211> LENGTH: 843
<212> TYPE: DNA
<213> ORGANISM: Canis familiaris
<220> FEATURE:
<221> NAME/KEY: CDS
<222> LOCATION: (9)..(689)

<400> SEQUENCE: 38

```
gcaaacat atg tac aaa att cta gag tct acg tac att gtg aaa aga tca      50
         Met Tyr Lys Ile Leu Glu Ser Thr Tyr Ile Val Lys Arg Ser
         1               5                   10 atc act gtc cct cag cca cca ttt gtg agt gtg acc ctg agg gac acg      98
Ile Thr Val Pro Gln Pro Pro Phe Val Ser Val Thr Leu Arg Asp Thr
15                  20                  25                  30
```

| | | | | | | | | | | | | | | | |
|---|---|---|---|---|---|---|---|---|---|---|---|---|---|---|---|
|gcc|cac|atc|acc|tgt|ggg|gga|gac|aac|att|gga|agt|aaa|tat|gtt|caa|146
|Ala|His|Ile|Thr|Cys|Gly|Gly|Asp|Asn|Ile|Gly|Ser|Lys|Tyr|Val|Gln|
| | | |35| | | |40| | | |45| | | | |

```
gcc cac atc acc tgt ggg gga gac aac att gga agt aaa tat gtt caa      146
Ala His Ile Thr Cys Gly Gly Asp Asn Ile Gly Ser Lys Tyr Val Gln
             35                  40                  45 tgg atc caa cag aat cca ggt cag gcc ccc gtg gtg att atc tat aga      194
Trp Ile Gln Gln Asn Pro Gly Gln Ala Pro Val Val Ile Ile Tyr Arg
         50                  55                  60 gat acc aag agg ccg aca tgg atc cct gag cga ttc tct ggc gcc aac      242
Asp Thr Lys Arg Pro Thr Trp Ile Pro Glu Arg Phe Ser Gly Ala Asn
         65                  70                  75 tca ggg aac acg gct acc ctg acc atc agt ggg gtc ctg gcc gag gac      290
Ser Gly Asn Thr Ala Thr Leu Thr Ile Ser Gly Val Leu Ala Glu Asp
     80                  85                  90 gag gct gac tat tac tgc cag gtg aca gac agt ggt cct cag act aat      338
Glu Ala Asp Tyr Tyr Cys Gln Val Thr Asp Ser Gly Pro Gln Thr Asn
95                 100                 105                 110 gtt ttc ggc gga ggc acc cat ctg acc gtc ctc agt cag ccc aag gcc      386
Val Phe Gly Gly Gly Thr His Leu Thr Val Leu Ser Gln Pro Lys Ala
                 115                 120                 125 tcc ccc tcg gtc aca ctc ttc ccg ccc tcc tct gag gag ctc ggc gcc      434
Ser Pro Ser Val Thr Leu Phe Pro Pro Ser Ser Glu Glu Leu Gly Ala
             130                 135                 140 aac aag gcc acc ctg gtg tgc ctc atc agc gac ttc tac ccc agt ggc      482
Asn Lys Ala Thr Leu Val Cys Leu Ile Ser Asp Phe Tyr Pro Ser Gly
         145                 150                 155 gtg acg gtg gcc tgg aag gca gac ggc agc ccc gtc acc cag ggc gtg      530
Val Thr Val Ala Trp Lys Ala Asp Gly Ser Pro Val Thr Gln Gly Val
         160                 165                 170 gag acc acc aag ccc tcc aag cag agc aac aac aag tac gcg gcc agc      578
Glu Thr Thr Lys Pro Ser Lys Gln Ser Asn Asn Lys Tyr Ala Ala Ser
175                 180                 185                 190 agc tac ctg agc ctg acg cct gac aag tgg aaa tct cac agc agc ttc      626
Ser Tyr Leu Ser Leu Thr Pro Asp Lys Trp Lys Ser His Ser Ser Phe
                 195                 200                 205 agc tgc ctg gtc aca cac gag ggg agc acc gtg gag aag aag gtg gcc      674
Ser Cys Leu Val Thr His Glu Gly Ser Thr Val Glu Lys Lys Val Ala
             210                 215                 220 ccc gca gag tgc tct taggttcccg acgcccccgc ccacctaagg gggcccggag      729
Pro Ala Glu Cys Ser
225 cctcaggacc tccaggagga tcttgcctcc tatctgggtc atcccgccct tctccccaca   789 cccaggcagc actcaataaa ttgttctttg ttcaatcaga aaaaggggg gccc           843

<210> SEQ ID NO 39
<211> LENGTH: 227
<212> TYPE: PRT
<213> ORGANISM: Canis familiaris

<400> SEQUENCE: 39

Met Tyr Lys Ile Leu Glu Ser Thr Tyr Ile Val Lys Arg Ser Ile Thr
1               5                  10                  15

Val Pro Gln Pro Pro Phe Val Ser Val Thr Leu Arg Asp Thr Ala His
             20                  25                  30

Ile Thr Cys Gly Gly Asp Asn Ile Gly Ser Lys Tyr Val Gln Trp Ile
         35                  40                  45

Gln Gln Asn Pro Gly Gln Ala Pro Val Val Ile Ile Tyr Arg Asp Thr
     50                  55                  60

Lys Arg Pro Thr Trp Ile Pro Glu Arg Phe Ser Gly Ala Asn Ser Gly
65                  70                  75                  80
```

```
Asn Thr Ala Thr Leu Thr Ile Ser Gly Val Leu Ala Glu Asp Glu Ala
                85                  90                  95

Asp Tyr Tyr Cys Gln Val Thr Asp Ser Gly Pro Gln Thr Asn Val Phe
            100                 105                 110

Gly Gly Gly Thr His Leu Thr Val Leu Ser Gln Pro Lys Ala Ser Pro
        115                 120                 125

Ser Val Thr Leu Phe Pro Pro Ser Ser Glu Glu Leu Gly Ala Asn Lys
    130                 135                 140

Ala Thr Leu Val Cys Leu Ile Ser Asp Phe Tyr Pro Ser Gly Val Thr
145                 150                 155                 160

Val Ala Trp Lys Ala Asp Gly Ser Pro Val Thr Gln Gly Val Glu Thr
                165                 170                 175

Thr Lys Pro Ser Lys Gln Ser Asn Asn Lys Tyr Ala Ala Ser Ser Tyr
            180                 185                 190

Leu Ser Leu Thr Pro Asp Lys Trp Lys Ser His Ser Ser Phe Ser Cys
        195                 200                 205

Leu Val Thr His Glu Gly Ser Thr Val Glu Lys Lys Val Ala Pro Ala
    210                 215                 220

Glu Cys Ser
225

<210> SEQ ID NO 40
<211> LENGTH: 858
<212> TYPE: DNA
<213> ORGANISM: Canis familiaris
<220> FEATURE:
<221> NAME/KEY: CDS
<222> LOCATION: (2)..(709)

<400> SEQUENCE: 40 c tcc aac atg gcc tgg tcc cct ctc ctc ctc aca ctc ctt gct tac tgc       49
  Ser Asn Met Ala Trp Ser Pro Leu Leu Leu Thr Leu Leu Ala Tyr Cys
  1               5                   10                  15 aca ggg tcc tgg gcc cag tct gtg ctg act cag ccg acc tca gtg tcg       97
Thr Gly Ser Trp Ala Gln Ser Val Leu Thr Gln Pro Thr Ser Val Ser
             20                  25                  30 ggg tcc ctt ggc cag agg gtc acc atc tcc tgc tct gga agc acg aac      145
Gly Ser Leu Gly Gln Arg Val Thr Ile Ser Cys Ser Gly Ser Thr Asn
         35                  40                  45 aac atc ggt att gtt ggt gcg agc tgg tac caa cag ctc cca gga aag      193
Asn Ile Gly Ile Val Gly Ala Ser Trp Tyr Gln Gln Leu Pro Gly Lys
 50                  55                  60 gcc cct aaa ctc ctc gtg tac agt gtt ggg gat cga ccg tca ggg gtc      241
Ala Pro Lys Leu Leu Val Tyr Ser Val Gly Asp Arg Pro Ser Gly Val
65                  70                  75                  80 cct gac cgg ttt tcc ggc tcc aac tct ggc aac tca gcc acc ctg acc      289
Pro Asp Arg Phe Ser Gly Ser Asn Ser Gly Asn Ser Ala Thr Leu Thr
                 85                  90                  95 atc act ggg ctt cag gct gag gac gag gct gat tat tac tgc cag tcc      337
Ile Thr Gly Leu Gln Ala Glu Asp Glu Ala Asp Tyr Tyr Cys Gln Ser
            100                 105                 110 ttt gat acc acg ctt ggt gct gtg ttc ggc gga ggc acc cac ctg acc      385
Phe Asp Thr Thr Leu Gly Ala Val Phe Gly Gly Gly Thr His Leu Thr
        115                 120                 125 gtc ctc ggt cag ccc aag gcc tcc ccc tcg gtc aca ctc ttc ccg ccc      433
Val Leu Gly Gln Pro Lys Ala Ser Pro Ser Val Thr Leu Phe Pro Pro
    130                 135                 140 tcc tct gag gag ctc ggc gcc aac aag gcc acc ctg gtg tgc ctc atc      481
```

```
Ser Ser Glu Glu Leu Gly Ala Asn Lys Ala Thr Leu Val Cys Leu Ile
145                 150                 155                 160 agc gac ttc tac ccc agc ggc gtg acg gtg gcc tgg aag gca gac ggc      529
Ser Asp Phe Tyr Pro Ser Gly Val Thr Val Ala Trp Lys Ala Asp Gly
                165                 170                 175 agc ccc gtc acc cag ggc gtg gag acc acc aag ccc tcc aag cag agc      577
Ser Pro Val Thr Gln Gly Val Glu Thr Thr Lys Pro Ser Lys Gln Ser
            180                 185                 190 aac aac aag tac gcg gcc agc agc tac ctg agc ctg acg cct gac aag      625
Asn Asn Lys Tyr Ala Ala Ser Ser Tyr Leu Ser Leu Thr Pro Asp Lys
        195                 200                 205 tgg aaa tct cac agc agc ttc agc tgc ctg gtc acg cac gag ggg agc      673
Trp Lys Ser His Ser Ser Phe Ser Cys Leu Val Thr His Glu Gly Ser
    210                 215                 220 acc gtg gag aag aag gtg gcc ccc gca gag tgc tct taggttccg            719
Thr Val Glu Lys Lys Val Ala Pro Ala Glu Cys Ser
225                 230                 235 acggccccgc ccaccgaagg gggcccggag cctcaggacc tccaggagga tcttgcctcc    779
catctgggtc atcccgccct tctccccgca cccaggcagc actcaataaa gtgttctttg    839
ttcaatcaga aaaaaaaaa                                                 858

<210> SEQ ID NO 41
<211> LENGTH: 236
<212> TYPE: PRT
<213> ORGANISM: Canis familiaris

<400> SEQUENCE: 41

Ser Asn Met Ala Trp Ser Pro Leu Leu Leu Thr Leu Leu Ala Tyr Cys
1               5                   10                  15

Thr Gly Ser Trp Ala Gln Ser Val Leu Thr Gln Pro Thr Ser Val Ser
            20                  25                  30

Gly Ser Leu Gly Gln Arg Val Thr Ile Ser Cys Ser Gly Ser Thr Asn
        35                  40                  45

Asn Ile Gly Ile Val Gly Ala Ser Trp Tyr Gln Gln Leu Pro Gly Lys
    50                  55                  60

Ala Pro Lys Leu Leu Val Tyr Ser Val Gly Asp Arg Pro Ser Gly Val
65                  70                  75                  80

Pro Asp Arg Phe Ser Gly Ser Asn Ser Gly Asn Ser Ala Thr Leu Thr
                85                  90                  95

Ile Thr Gly Leu Gln Ala Glu Asp Glu Ala Asp Tyr Tyr Cys Gln Ser
            100                 105                 110

Phe Asp Thr Thr Leu Gly Ala Val Phe Gly Gly Gly Thr His Leu Thr
        115                 120                 125

Val Leu Gly Gln Pro Lys Ala Ser Pro Ser Val Thr Leu Phe Pro Pro
    130                 135                 140

Ser Ser Glu Glu Leu Gly Ala Asn Lys Ala Thr Leu Val Cys Leu Ile
145                 150                 155                 160

Ser Asp Phe Tyr Pro Ser Gly Val Thr Val Ala Trp Lys Ala Asp Gly
                165                 170                 175

Ser Pro Val Thr Gln Gly Val Glu Thr Thr Lys Pro Ser Lys Gln Ser
            180                 185                 190

Asn Asn Lys Tyr Ala Ala Ser Ser Tyr Leu Ser Leu Thr Pro Asp Lys
        195                 200                 205

Trp Lys Ser His Ser Ser Phe Ser Cys Leu Val Thr His Glu Gly Ser
    210                 215                 220
```

Thr Val Glu Lys Lys Val Ala Pro Ala Glu Cys Ser
225                 230                 235

<210> SEQ ID NO 42
<211> LENGTH: 514
<212> TYPE: DNA
<213> ORGANISM: Canis familiaris
<220> FEATURE:
<221> NAME/KEY: CDS
<222> LOCATION: (1)..(378)

<400> SEQUENCE: 42

```
atg ttc gag gct gtg tca cag tgt gct gtg ttc ggc gga ggc acc cac      48
Met Phe Glu Ala Val Ser Gln Cys Ala Val Phe Gly Gly Gly Thr His
1               5                   10                  15 ctg acc gtc ctc ggt cag ccc aag gcc tcc ccc tcg gtc aca ctc ttc      96
Leu Thr Val Leu Gly Gln Pro Lys Ala Ser Pro Ser Val Thr Leu Phe
            20                  25                  30 ccg ccc tcc tct gag gag ctc ggc gcc aac aag gcc acc ctg gtg tgc     144
Pro Pro Ser Ser Glu Glu Leu Gly Ala Asn Lys Ala Thr Leu Val Cys
        35                  40                  45 ctc atc agc gac ttc tac ccc agc ggc gtg acg gtg gcc tgg aag gca     192
Leu Ile Ser Asp Phe Tyr Pro Ser Gly Val Thr Val Ala Trp Lys Ala
    50                  55                  60 gac ggc agc ccc gtc acc cag ggc gtg gag acc acc aag ccc tcc aag     240
Asp Gly Ser Pro Val Thr Gln Gly Val Glu Thr Thr Lys Pro Ser Lys
65                  70                  75                  80 cag agc aac aac aag tac gcg gcc agc agc tac ctg agc ctg acg cct     288
Gln Ser Asn Asn Lys Tyr Ala Ala Ser Ser Tyr Leu Ser Leu Thr Pro
                85                  90                  95 gac aag tgg aaa tct cac agc agc ttc agc tgc ctg gtc acg cac gag     336
Asp Lys Trp Lys Ser His Ser Ser Phe Ser Cys Leu Val Thr His Glu
            100                 105                 110 ggg agc acc gtg gag aag aag gtg gcc ccc gca gag tgc tct                 378
Gly Ser Thr Val Glu Lys Lys Val Ala Pro Ala Glu Cys Ser
        115                 120                 125 taggttcccg acggccccgc ccaccgaagg gggcccggag cctcaggacc tccaggagga    438
tcttgcctcc catctgggtc atcccgccct ctccccgca cccaggcagc actcaataaa     498
gtgttctttg ttcaat                                                    514
```

<210> SEQ ID NO 43
<211> LENGTH: 126
<212> TYPE: PRT
<213> ORGANISM: Canis familiaris

<400> SEQUENCE: 43

Met Phe Glu Ala Val Ser Gln Cys Ala Val Phe Gly Gly Gly Thr His
1               5                   10                  15

Leu Thr Val Leu Gly Gln Pro Lys Ala Ser Pro Ser Val Thr Leu Phe
            20                  25                  30

Pro Pro Ser Ser Glu Glu Leu Gly Ala Asn Lys Ala Thr Leu Val Cys
        35                  40                  45

Leu Ile Ser Asp Phe Tyr Pro Ser Gly Val Thr Val Ala Trp Lys Ala
    50                  55                  60

Asp Gly Ser Pro Val Thr Gln Gly Val Glu Thr Thr Lys Pro Ser Lys
65                  70                  75                  80

Gln Ser Asn Asn Lys Tyr Ala Ala Ser Ser Tyr Leu Ser Leu Thr Pro
                85                  90                  95

Asp Lys Trp Lys Ser His Ser Ser Phe Ser Cys Leu Val Thr His Glu

```
                    100                 105                 110
Gly Ser Thr Val Glu Lys Lys Val Ala Pro Ala Glu Cys Ser
        115                 120                 125

<210> SEQ ID NO 44
<211> LENGTH: 514
<212> TYPE: DNA
<213> ORGANISM: Canis familiaris
<220> FEATURE:
<221> NAME/KEY: CDS
<222> LOCATION: (1)..(378)

<400> SEQUENCE: 44 atg ttc gag gct gtg tca cag tgt gct gtg ttc ggc gga ggc acc cac       48
Met Phe Glu Ala Val Ser Gln Cys Ala Val Phe Gly Gly Gly Thr His
1               5                   10                  15 ctg acc gtc ctc ggt cag ccc aag gcc tcc ccc tcg gtc aca ctc ttc       96
Leu Thr Val Leu Gly Gln Pro Lys Ala Ser Pro Ser Val Thr Leu Phe
            20                  25                  30 ccg ccc tcc tct gag gag ctc ggc gcc aac aag gcc acc ctg gtg tgc      144
Pro Pro Ser Ser Glu Glu Leu Gly Ala Asn Lys Ala Thr Leu Val Cys
        35                  40                  45 ctc atc agc gac ttc tac ccc agc ggc gtg acg gtg gcc tgg aag gca      192
Leu Ile Ser Asp Phe Tyr Pro Ser Gly Val Thr Val Ala Trp Lys Ala
    50                  55                  60 gac ggc agc ccc gtc acc cag ggc gtg gag acc acc aag ccc tcc aag      240
Asp Gly Ser Pro Val Thr Gln Gly Val Glu Thr Thr Lys Pro Ser Lys
65                  70                  75                  80 cag agc aac aac aag tac gcg gcc agc agc tac ctg agc ctg acg cct      288
Gln Ser Asn Asn Lys Tyr Ala Ala Ser Ser Tyr Leu Ser Leu Thr Pro
                85                  90                  95 gac aag tgg aaa tct cac agc agc ttc agc tgc ctg gtc acg cac gag      336
Asp Lys Trp Lys Ser His Ser Ser Phe Ser Cys Leu Val Thr His Glu
            100                 105                 110 ggg agc acc gtg gag aag aag gtg gcc ccc gca gag tgc tct              378
Gly Ser Thr Val Glu Lys Lys Val Ala Pro Ala Glu Cys Ser
        115                 120                 125 taggttcccg acggccccgc ccaccgaagg gggcccggag cctcaggacc tccaggagga    438
tcttgcctcc catctgggtc atcccgctct tctccccgca cccaggcagc actcaataaa    498
gtgttctttg ttcaat                                                    514

<210> SEQ ID NO 45
<211> LENGTH: 126
<212> TYPE: PRT
<213> ORGANISM: Canis familiaris

<400> SEQUENCE: 45

Met Phe Glu Ala Val Ser Gln Cys Ala Val Phe Gly Gly Gly Thr His
1               5                   10                  15

Leu Thr Val Leu Gly Gln Pro Lys Ala Ser Pro Ser Val Thr Leu Phe
            20                  25                  30

Pro Pro Ser Ser Glu Glu Leu Gly Ala Asn Lys Ala Thr Leu Val Cys
        35                  40                  45

Leu Ile Ser Asp Phe Tyr Pro Ser Gly Val Thr Val Ala Trp Lys Ala
    50                  55                  60

Asp Gly Ser Pro Val Thr Gln Gly Val Glu Thr Thr Lys Pro Ser Lys
65                  70                  75                  80

Gln Ser Asn Asn Lys Tyr Ala Ala Ser Ser Tyr Leu Ser Leu Thr Pro
                85                  90                  95
```

```
Asp Lys Trp Lys Ser His Ser Ser Phe Ser Cys Leu Val Thr His Glu
            100                 105                 110

Gly Ser Thr Val Glu Lys Lys Val Ala Pro Ala Glu Cys Ser
            115                 120                 125

<210> SEQ ID NO 46
<211> LENGTH: 561
<212> TYPE: DNA
<213> ORGANISM: Canis familiaris
<220> FEATURE:
<221> NAME/KEY: CDS
<222> LOCATION: (1)..(423)

<400> SEQUENCE: 46 atg ggc ctg ggg cag ggg agg ggc tgc agg ggt gac aga ggg ttt gtg      48
Met Gly Leu Gly Gln Gly Arg Gly Cys Arg Gly Asp Arg Gly Phe Val
1               5                   10                  15 ttc aag gct gta tca ctg tgt tac gtg ttc ggc tca gga acc caa ctg      96
Phe Lys Ala Val Ser Leu Cys Tyr Val Phe Gly Ser Gly Thr Gln Leu
                20                  25                  30 acc gtc ctt ggt cag ccc aag gcc tcc ccc tcg gtc aca ctc ttc ccg     144
Thr Val Leu Gly Gln Pro Lys Ala Ser Pro Ser Val Thr Leu Phe Pro
            35                  40                  45 ccc tcc tct gag gag ctc ggc gcc aac aag gcc acc ctg gtg tgc ctc     192
Pro Ser Ser Glu Glu Leu Gly Ala Asn Lys Ala Thr Leu Val Cys Leu
        50                  55                  60 atc agc gac ttc tac ccc agc ggc gtg acg gtg gcc tgg aag gca gac     240
Ile Ser Asp Phe Tyr Pro Ser Gly Val Thr Val Ala Trp Lys Ala Asp
65                  70                  75                  80 ggc agc ccc atc acc cag ggc gtg gag acc acc aag ccc tcc aag cag     288
Gly Ser Pro Ile Thr Gln Gly Val Glu Thr Thr Lys Pro Ser Lys Gln
                85                  90                  95 agc aac aac aag tac gcg gcc agc agc tac ctg agc ctg acg cct gac     336
Ser Asn Asn Lys Tyr Ala Ala Ser Ser Tyr Leu Ser Leu Thr Pro Asp
            100                 105                 110 aag tgg aaa tct cac agc agc ttc agc tgc ctg gtc acg cac gag ggg     384
Lys Trp Lys Ser His Ser Ser Phe Ser Cys Leu Val Thr His Glu Gly
        115                 120                 125 agc act gtg gag aag aag gtg gcc ccc gca gag tgc tct taggttccg       433
Ser Thr Val Glu Lys Lys Val Ala Pro Ala Glu Cys Ser
    130                 135                 140 atgccccccg cccaccgaag ggggctcgga gcctcaggac ctccaggagg atcttgcctc    493
ccatctgggt cttcccagcc cttttcccca cactcaggca acactcaata aagtgtcctt    553
tattcaat                                                             561

<210> SEQ ID NO 47
<211> LENGTH: 141
<212> TYPE: PRT
<213> ORGANISM: Canis familiaris

<400> SEQUENCE: 47

Met Gly Leu Gly Gln Gly Arg Gly Cys Arg Gly Asp Arg Gly Phe Val
1               5                   10                  15

Phe Lys Ala Val Ser Leu Cys Tyr Val Phe Gly Ser Gly Thr Gln Leu
                20                  25                  30

Thr Val Leu Gly Gln Pro Lys Ala Ser Pro Ser Val Thr Leu Phe Pro
            35                  40                  45

Pro Ser Ser Glu Glu Leu Gly Ala Asn Lys Ala Thr Leu Val Cys Leu
        50                  55                  60
```

```
Ile Ser Asp Phe Tyr Pro Ser Gly Val Thr Val Ala Trp Lys Ala Asp
 65                  70                  75                  80

Gly Ser Pro Ile Thr Gln Gly Val Glu Thr Thr Lys Pro Ser Lys Gln
                 85                  90                  95

Ser Asn Asn Lys Tyr Ala Ala Ser Ser Tyr Leu Ser Leu Thr Pro Asp
            100                 105                 110

Lys Trp Lys Ser His Ser Ser Phe Ser Cys Leu Val Thr His Glu Gly
        115                 120                 125

Ser Thr Val Glu Lys Lys Val Ala Pro Ala Glu Cys Ser
    130                 135                 140

<210> SEQ ID NO 48
<211> LENGTH: 514
<212> TYPE: DNA
<213> ORGANISM: Canis familiaris
<220> FEATURE:
<221> NAME/KEY: CDS
<222> LOCATION: (1)..(378)

<400> SEQUENCE: 48 atg ttc gag gct gtg tca cag tgt gct gtg ttc ggc gga ggc acc cac    48
Met Phe Glu Ala Val Ser Gln Cys Ala Val Phe Gly Gly Gly Thr His
 1               5                  10                  15 ctg acc gtc ctc ggt cag ccc aag gcc tcc ccc tcg gtc aca ctc ttc    96
Leu Thr Val Leu Gly Gln Pro Lys Ala Ser Pro Ser Val Thr Leu Phe
             20                  25                  30 ccg ccc tcc tct gag gag ctc ggc gcc aac aag gcc acc ctg gtg tgc   144
Pro Pro Ser Ser Glu Glu Leu Gly Ala Asn Lys Ala Thr Leu Val Cys
         35                  40                  45 ctc atc agc gac ttc tac ccc agc ggc gtg acg gtg gcc tgg aag gca   192
Leu Ile Ser Asp Phe Tyr Pro Ser Gly Val Thr Val Ala Trp Lys Ala
     50                  55                  60 gac ggc agc ccc gtc acc cag ggc gtg gag acc acc aag ccc tcc aag   240
Asp Gly Ser Pro Val Thr Gln Gly Val Glu Thr Thr Lys Pro Ser Lys
 65                  70                  75                  80 cag agc aac aac aag tac gcg gcc agc agc tac ctg agc ctg acg cct   288
Gln Ser Asn Asn Lys Tyr Ala Ala Ser Ser Tyr Leu Ser Leu Thr Pro
                 85                  90                  95 gac aag tgg aaa tct cac agc agc ttc agc tgc ctg gtc acg cac gag   336
Asp Lys Trp Lys Ser His Ser Ser Phe Ser Cys Leu Val Thr His Glu
            100                 105                 110 ggg agc acc gtg gag aag aag gtg gcc ccc gca gag tgc tct           378
Gly Ser Thr Val Glu Lys Lys Val Ala Pro Ala Glu Cys Ser
        115                 120                 125 taggttcccg acggccccgc ccacctaagg gggcccggag cctcaggacc tccaggagga   438
tcttgcctcc catctgggtc atcccgctct tctccccgca cccaggcagc actcaataaa   498
gtgttctttg ttcaat                                                    514

<210> SEQ ID NO 49
<211> LENGTH: 126
<212> TYPE: PRT
<213> ORGANISM: Canis familiaris

<400> SEQUENCE: 49

Met Phe Glu Ala Val Ser Gln Cys Ala Val Phe Gly Gly Gly Thr His
 1               5                  10                  15

Leu Thr Val Leu Gly Gln Pro Lys Ala Ser Pro Ser Val Thr Leu Phe
             20                  25                  30
```

```
Pro Pro Ser Ser Glu Glu Leu Gly Ala Asn Lys Ala Thr Leu Val Cys
            35                  40                  45

Leu Ile Ser Asp Phe Tyr Pro Ser Gly Val Thr Val Ala Trp Lys Ala
 50                  55                  60

Asp Gly Ser Pro Val Thr Gln Gly Val Glu Thr Thr Lys Pro Ser Lys
 65                  70                  75                  80

Gln Ser Asn Asn Lys Tyr Ala Ala Ser Ser Tyr Leu Ser Leu Thr Pro
                 85                  90                  95

Asp Lys Trp Lys Ser His Ser Ser Phe Ser Cys Leu Val Thr His Glu
            100                 105                 110

Gly Ser Thr Val Glu Lys Lys Val Ala Pro Ala Glu Cys Ser
            115                 120                 125

<210> SEQ ID NO 50
<211> LENGTH: 514
<212> TYPE: DNA
<213> ORGANISM: Canis familiaris
<220> FEATURE:
<221> NAME/KEY: CDS
<222> LOCATION: (1)..(378)

<400> SEQUENCE: 50 atg ttc gag gct gtg tca cag tgt gct gtg ttc ggc gga ggc acc cac      48
Met Phe Glu Ala Val Ser Gln Cys Ala Val Phe Gly Gly Gly Thr His
 1               5                  10                  15 ctg acc gtc ctc ggt cag ccc aag gcc tcc ccc tcg gtc aca ctc ttc      96
Leu Thr Val Leu Gly Gln Pro Lys Ala Ser Pro Ser Val Thr Leu Phe
                 20                  25                  30 ccg ccc tcc tct gag gag ctc ggc gcc aac aag gcc acc ctg gtg tgc     144
Pro Pro Ser Ser Glu Glu Leu Gly Ala Asn Lys Ala Thr Leu Val Cys
            35                  40                  45 ctc atc agc gac ttc tac ccc agc ggc gtg acg gtg gcc tgg aag gca     192
Leu Ile Ser Asp Phe Tyr Pro Ser Gly Val Thr Val Ala Trp Lys Ala
 50                  55                  60 gac ggc agc ccc gtc acc cag ggc gtg gag acc acc aag ccc tcc aag     240
Asp Gly Ser Pro Val Thr Gln Gly Val Glu Thr Thr Lys Pro Ser Lys
 65                  70                  75                  80 cag agc aac aac aag tac gcg gcc agc agc tac ctg agc ctg acg cct     288
Gln Ser Asn Asn Lys Tyr Ala Ala Ser Ser Tyr Leu Ser Leu Thr Pro
                 85                  90                  95 gac aag tgg aaa tct cac agc agc ttc agc tgc ctg gtc acg cac gag     336
Asp Lys Trp Lys Ser His Ser Ser Phe Ser Cys Leu Val Thr His Glu
            100                 105                 110 ggg agc acc gtg gag aag aag gtg gcc ccc gca gag tgc tct               378
Gly Ser Thr Val Glu Lys Lys Val Ala Pro Ala Glu Cys Ser
            115                 120                 125 taggttcccg acggccccgc ccaccgaagg gggcccggag cctcaggacc tccaggagga    438
tcttgcctcc catctgggtc atcccgctct tctccccgca cccaggcagc actcaataaa    498
gtgttctttg ttcaat                                                    514

<210> SEQ ID NO 51
<211> LENGTH: 126
<212> TYPE: PRT
<213> ORGANISM: Canis familiaris

<400> SEQUENCE: 51

Met Phe Glu Ala Val Ser Gln Cys Ala Val Phe Gly Gly Gly Thr His
 1               5                  10                  15

Leu Thr Val Leu Gly Gln Pro Lys Ala Ser Pro Ser Val Thr Leu Phe
```

```
                20                  25                  30
Pro Pro Ser Ser Glu Glu Leu Gly Ala Asn Lys Ala Thr Leu Val Cys
            35                  40                  45

Leu Ile Ser Asp Phe Tyr Pro Ser Gly Val Thr Val Ala Trp Lys Ala
        50                  55                  60

Asp Gly Ser Pro Val Thr Gln Gly Val Glu Thr Thr Lys Pro Ser Lys
65                  70                  75                  80

Gln Ser Asn Asn Lys Tyr Ala Ala Ser Ser Tyr Leu Ser Leu Thr Pro
                85                  90                  95

Asp Lys Trp Lys Ser His Ser Ser Phe Ser Cys Leu Val Thr His Glu
            100                 105                 110

Gly Ser Thr Val Glu Lys Lys Val Ala Pro Ala Glu Cys Ser
        115                 120                 125

<210> SEQ ID NO 52
<211> LENGTH: 697
<212> TYPE: DNA
<213> ORGANISM: Canis familiaris
<220> FEATURE:
<221> NAME/KEY: CDS
<222> LOCATION: (1)..(561)

<400> SEQUENCE: 52 atg ggc aca cat ggt gac tac caa tca cgg tta gaa ttt caa cca cct    48
Met Gly Thr His Gly Asp Tyr Gln Ser Arg Leu Glu Phe Gln Pro Pro
1               5                   10                  15 gaa tgg tgg gct act ctc aga aat gat cgg gaa aag ctg gag gat ggg    96
Glu Trp Trp Ala Thr Leu Arg Asn Asp Arg Glu Lys Leu Glu Asp Gly
            20                  25                  30 act ctc aga atc cca cgg tgg cac atg aac aaa tac cta gtc acg aca   144
Thr Leu Arg Ile Pro Arg Trp His Met Asn Lys Tyr Leu Val Thr Thr
        35                  40                  45 gtc ccc gta gag cca gcc agt ctc aaa gag gtg gcc agg aag att ccg   192
Val Pro Val Glu Pro Ala Ser Leu Lys Glu Val Ala Arg Lys Ile Pro
    50                  55                  60 atc cat gat gaa tgt ggt gtg ttc ggc gga ggc acc cac ctg acc gtc   240
Ile His Asp Glu Cys Gly Val Phe Gly Gly Gly Thr His Leu Thr Val
65                  70                  75                  80 ctc ggt cag ccc aag gcc tcc ccg tcg gtc aca ctc ttc ccg ccc tcc   288
Leu Gly Gln Pro Lys Ala Ser Pro Ser Val Thr Leu Phe Pro Pro Ser
                85                  90                  95 tct gag gag ctc ggc gcc aac aag gcc acc ctg gtg tgc ctc atc agc   336
Ser Glu Glu Leu Gly Ala Asn Lys Ala Thr Leu Val Cys Leu Ile Ser
            100                 105                 110 gac ttc tac ccc agc ggt gtg acg gtg gcc tgg aag gca gac ggc agc   384
Asp Phe Tyr Pro Ser Gly Val Thr Val Ala Trp Lys Ala Asp Gly Ser
        115                 120                 125 ccc gtc acc cag ggc gtg gag acc acc aag ccc tcc aag cag agc aac   432
Pro Val Thr Gln Gly Val Glu Thr Thr Lys Pro Ser Lys Gln Ser Asn
    130                 135                 140 aac aag tac gcg gcc agc agc tac ctg agc ctg acg cct gac aag tgg   480
Asn Lys Tyr Ala Ala Ser Ser Tyr Leu Ser Leu Thr Pro Asp Lys Trp
145                 150                 155                 160 aaa tct cac agc agc ttc agc tgc ctg gtc acg cac gag ggg agc acc   528
Lys Ser His Ser Ser Phe Ser Cys Leu Val Thr His Glu Gly Ser Thr
                165                 170                 175 gtg gag aag aag gtg gcc ccc gca gag tgc tct taggttccg acggccccgc   581
Val Glu Lys Lys Val Ala Pro Ala Glu Cys Ser
            180                 185
```

```
ccaccgaagg gggcccggag cctcaggacc tccaggagga tcttgcctcc catctgggtc      641
atcccgccct tctccccgca cccaggcagc actcaataaa gtgttctttg ttcaat          697
```

<210> SEQ ID NO 53
<211> LENGTH: 187
<212> TYPE: PRT
<213> ORGANISM: Canis familiaris

<400> SEQUENCE: 53

```
Met Gly Thr His Gly Asp Tyr Gln Ser Arg Leu Glu Phe Gln Pro Pro
1               5                   10                  15

Glu Trp Trp Ala Thr Leu Arg Asn Asp Arg Glu Lys Leu Glu Asp Gly
            20                  25                  30

Thr Leu Arg Ile Pro Arg Trp His Met Asn Lys Tyr Leu Val Thr Thr
        35                  40                  45

Val Pro Val Glu Pro Ala Ser Leu Lys Glu Val Ala Arg Lys Ile Pro
    50                  55                  60

Ile His Asp Glu Cys Gly Val Phe Gly Gly Thr His Leu Thr Val
65                  70                  75                  80

Leu Gly Gln Pro Lys Ala Ser Pro Ser Val Thr Leu Phe Pro Pro Ser
            85                  90                  95

Ser Glu Glu Leu Gly Ala Asn Lys Ala Thr Leu Val Cys Leu Ile Ser
            100                 105                 110

Asp Phe Tyr Pro Ser Gly Val Thr Val Ala Trp Lys Ala Asp Gly Ser
        115                 120                 125

Pro Val Thr Gln Gly Val Glu Thr Thr Lys Pro Ser Lys Gln Ser Asn
    130                 135                 140

Asn Lys Tyr Ala Ala Ser Ser Tyr Leu Ser Leu Thr Pro Asp Lys Trp
145                 150                 155                 160

Lys Ser His Ser Ser Phe Ser Cys Leu Val Thr His Glu Gly Ser Thr
                165                 170                 175

Val Glu Lys Lys Val Ala Pro Ala Glu Cys Ser
            180                 185
```

<210> SEQ ID NO 54
<211> LENGTH: 634
<212> TYPE: DNA
<213> ORGANISM: Canis familiaris
<220> FEATURE:
<221> NAME/KEY: CDS
<222> LOCATION: (1)..(498)

<400> SEQUENCE: 54

```
atg gaa atg aaa ttc ctg gac ccc agt ggc tat gcc ctc atc acc caa      48
Met Glu Met Lys Phe Leu Asp Pro Ser Gly Tyr Ala Leu Ile Thr Gln
1               5                   10                  15 ccc ccc ttc aac ccg acc agt acc cgt gac aag ggg gct gcc ctt tgg      96
Pro Pro Phe Asn Pro Thr Ser Thr Arg Asp Lys Gly Ala Ala Leu Trp
            20                  25                  30 gcc tcc cga gca gct gca ggg ttt gtg ctc gag gct gtg tca cag tgt     144
Ala Ser Arg Ala Ala Ala Gly Phe Val Leu Glu Ala Val Ser Gln Cys
        35                  40                  45 att gtg ttc ggc gga ggc acc cat ctg acc gtc ctc ggt cag ccc aag     192
Ile Val Phe Gly Gly Gly Thr His Leu Thr Val Leu Gly Gln Pro Lys
    50                  55                  60 gcc tcc cct tcg gtc aca ctc ttc ccg ccc tcc tct gag gag ctt ggc     240
Ala Ser Pro Ser Val Thr Leu Phe Pro Pro Ser Ser Glu Glu Leu Gly
65                  70                  75                  80
```

```
gcc aac aag gcc acc ctg gtg tgc ctc atc agc gac ttc tac ccc agc    288
Ala Asn Lys Ala Thr Leu Val Cys Leu Ile Ser Asp Phe Tyr Pro Ser
             85                  90                  95 ggc gtg aca gtg gcc tgg aag gca gac ggc agc ccc atc acc cag ggt    336
Gly Val Thr Val Ala Trp Lys Ala Asp Gly Ser Pro Ile Thr Gln Gly
            100                 105                 110 gtg gag acc acc aag ccc tcc aag cag agc aac aac aag tac gcg gcc    384
Val Glu Thr Thr Lys Pro Ser Lys Gln Ser Asn Asn Lys Tyr Ala Ala
        115                 120                 125 agc agc tac ctg agc ctg acg cct gac aag tgg aaa tct cac agc agc    432
Ser Ser Tyr Leu Ser Leu Thr Pro Asp Lys Trp Lys Ser His Ser Ser
    130                 135                 140 ttc agc tgc ctg gtc acg cac gag ggg agc acc gtg gag aag aag gtg    480
Phe Ser Cys Leu Val Thr His Glu Gly Ser Thr Val Glu Lys Lys Val
145                 150                 155                 160 gcc ccc gca gag tgc tct taggttcctg atgtccccg cccaccaaag             528
Ala Pro Ala Glu Cys Ser
                165 ggggctcaga gcctcaggac ctccaggagg atcttgcctc ccatctgggt catcccagcc   588 tttcccctta aacccaggca acattcaata aagtgttctt tcttca                  634

<210> SEQ ID NO 55
<211> LENGTH: 166
<212> TYPE: PRT
<213> ORGANISM: Canis familiaris

<400> SEQUENCE: 55

Met Glu Met Lys Phe Leu Asp Pro Ser Gly Tyr Ala Leu Ile Thr Gln
1               5                   10                  15

Pro Pro Phe Asn Pro Thr Ser Thr Arg Asp Lys Gly Ala Ala Leu Trp
            20                  25                  30

Ala Ser Arg Ala Ala Gly Phe Val Leu Glu Ala Val Ser Gln Cys
        35                  40                  45

Ile Val Phe Gly Gly Thr His Leu Thr Val Leu Gly Gln Pro Lys
    50                  55                  60

Ala Ser Pro Ser Val Thr Leu Phe Pro Pro Ser Ser Glu Glu Leu Gly
65                  70                  75                  80

Ala Asn Lys Ala Thr Leu Val Cys Leu Ile Ser Asp Phe Tyr Pro Ser
                85                  90                  95

Gly Val Thr Val Ala Trp Lys Ala Asp Gly Ser Pro Ile Thr Gln Gly
            100                 105                 110

Val Glu Thr Thr Lys Pro Ser Lys Gln Ser Asn Asn Lys Tyr Ala Ala
        115                 120                 125

Ser Ser Tyr Leu Ser Leu Thr Pro Asp Lys Trp Lys Ser His Ser Ser
    130                 135                 140

Phe Ser Cys Leu Val Thr His Glu Gly Ser Thr Val Glu Lys Lys Val
145                 150                 155                 160

Ala Pro Ala Glu Cys Ser
                165

<210> SEQ ID NO 56
<211> LENGTH: 551
<212> TYPE: DNA
<213> ORGANISM: Canis familiaris
<220> FEATURE:
<221> NAME/KEY: CDS
<222> LOCATION: (39)..(416)

<400> SEQUENCE: 56
```

```
ggtcatggat atgacacagc tgtaccccca caccaaga atg agg cag ttg ctg aca      56
                                             Met Arg Gln Leu Leu Thr
                                             1               5 caa caa aca tct gcc ttg acc cgc tgt cct tcc atc ccc aca ggt cag        104
Gln Gln Thr Ser Ala Leu Thr Arg Cys Pro Ser Ile Pro Thr Gly Gln
            10                  15                  20 ccc aag gcc tcc ccc tcg gtc aca ctc ttc ccg ccc tcc tct gag gag        152
Pro Lys Ala Ser Pro Ser Val Thr Leu Phe Pro Pro Ser Ser Glu Glu
            25                  30                  35 ctc ggc gcc aac aag gcc acc ctg gtg tgc ctc atc agc gac ttc tac        200
Leu Gly Ala Asn Lys Ala Thr Leu Val Cys Leu Ile Ser Asp Phe Tyr
        40                  45                  50 ccc agt ggc gtg acg gtg gcc tgg aag gca gac ggc agc ccc gtc acc        248
Pro Ser Gly Val Thr Val Ala Trp Lys Ala Asp Gly Ser Pro Val Thr
55                  60                  65                  70 cag ggc gtg gag acc acc aag ccc tcc aag cag agc aac aac aag tac        296
Gln Gly Val Glu Thr Thr Lys Pro Ser Lys Gln Ser Asn Asn Lys Tyr
                75                  80                  85 gcg gcc agc agc tac ctg agc ctg acg cct gac aag tgg aaa tct cac        344
Ala Ala Ser Ser Tyr Leu Ser Leu Thr Pro Asp Lys Trp Lys Ser His
            90                  95                  100 agc agc ttc agc tgc ctg gtc aca cac gag ggg agc acc gtg gag aag        392
Ser Ser Phe Ser Cys Leu Val Thr His Glu Gly Ser Thr Val Glu Lys
            105                 110                 115 aag gtg gcc ccc gca gag tgc tct taggttccg acgccccgc ccacctaagg         446
Lys Val Ala Pro Ala Glu Cys Ser
            120                 125 gggcccggag cctcaggacc tccaggagga tcttgcctcc tatctgggtc atcccgccct      506
tctccccaca cccaggcagc actcaataaa gtgttctttg ttcaa                      551

<210> SEQ ID NO 57
<211> LENGTH: 126
<212> TYPE: PRT
<213> ORGANISM: Canis familiaris

<400> SEQUENCE: 57

Met Arg Gln Leu Leu Thr Gln Gln Thr Ser Ala Leu Thr Arg Cys Pro
1               5                   10                  15

Ser Ile Pro Thr Gly Gln Pro Lys Ala Ser Pro Ser Val Thr Leu Phe
            20                  25                  30

Pro Pro Ser Ser Glu Glu Leu Gly Ala Asn Lys Ala Thr Leu Val Cys
        35                  40                  45

Leu Ile Ser Asp Phe Tyr Pro Ser Gly Val Thr Val Ala Trp Lys Ala
    50                  55                  60

Asp Gly Ser Pro Val Thr Gln Gly Val Glu Thr Thr Lys Pro Ser Lys
65                  70                  75                  80

Gln Ser Asn Asn Lys Tyr Ala Ala Ser Ser Tyr Leu Ser Leu Thr Pro
                85                  90                  95

Asp Lys Trp Lys Ser His Ser Ser Phe Ser Cys Leu Val Thr His Glu
            100                 105                 110

Gly Ser Thr Val Glu Lys Lys Val Ala Pro Ala Glu Cys Ser
        115                 120                 125

<210> SEQ ID NO 58
<211> LENGTH: 864
<212> TYPE: DNA
<213> ORGANISM: Canis familiaris
<220> FEATURE:
```

```
<221> NAME/KEY: CDS
<222> LOCATION: (1)..(699)

<400> SEQUENCE: 58 atg gcc tgg acc ctt ctt ctc ctt gga ttc ctg gct cac tgc aca ggt     48
Met Ala Trp Thr Leu Leu Leu Leu Gly Phe Leu Ala His Cys Thr Gly
1               5                   10                  15 tcc gtg gcc tcc tat gtg ctg act cag tca ccc tca gtg tca gtg acc     96
Ser Val Ala Ser Tyr Val Leu Thr Gln Ser Pro Ser Val Ser Val Thr
            20                  25                  30 ctg gga cag acg gcc agc atc acc tgt agg gga aac agc att gga agg    144
Leu Gly Gln Thr Ala Ser Ile Thr Cys Arg Gly Asn Ser Ile Gly Arg
        35                  40                  45 aaa gat gtt cat tgg tac cag cag aag ccg ggc caa gcc ccc ctg ctg    192
Lys Asp Val His Trp Tyr Gln Gln Lys Pro Gly Gln Ala Pro Leu Leu
    50                  55                  60 att atc tat aat gat aac agc cag ccc tca ggg atc cct gag cga ttc    240
Ile Ile Tyr Asn Asp Asn Ser Gln Pro Ser Gly Ile Pro Glu Arg Phe
65                  70                  75                  80 tct ggg acc aac tca ggg agc acg gcc acc ctg acc atc agt gag gcc    288
Ser Gly Thr Asn Ser Gly Ser Thr Ala Thr Leu Thr Ile Ser Glu Ala
                85                  90                  95 caa acc aac gat gag gct gac tat tac tgc cag gtg tgg gaa agt agc    336
Gln Thr Asn Asp Glu Ala Asp Tyr Tyr Cys Gln Val Trp Glu Ser Ser
            100                 105                 110 gct gat tgt tgg gta ttc ggt gaa ggg acc cag ctg acc gtc ctc ggt    384
Ala Asp Cys Trp Val Phe Gly Glu Gly Thr Gln Leu Thr Val Leu Gly
        115                 120                 125 cag ccc aag tcc tcc ccc ttg gtc aca ctc ttc ccg ccc tcc tct gag    432
Gln Pro Lys Ser Ser Pro Leu Val Thr Leu Phe Pro Pro Ser Ser Glu
    130                 135                 140 gag ctc ggc gcc aac aag gct acc ctg gtg tgc ctc atc agc gac ttc    480
Glu Leu Gly Ala Asn Lys Ala Thr Leu Val Cys Leu Ile Ser Asp Phe
145                 150                 155                 160 tac ccc agt ggc ctg aaa gtg gct tgg aag gca gat ggc agc acc atc    528
Tyr Pro Ser Gly Leu Lys Val Ala Trp Lys Ala Asp Gly Ser Thr Ile
                165                 170                 175 atc cag ggc gtg gaa acc acc aag ccc tcc aag cag agc aac aac aag    576
Ile Gln Gly Val Glu Thr Thr Lys Pro Ser Lys Gln Ser Asn Asn Lys
            180                 185                 190 tac acg gcc agc agc tac ctg agc ctg acg cct gac aag tgg aaa tct    624
Tyr Thr Ala Ser Ser Tyr Leu Ser Leu Thr Pro Asp Lys Trp Lys Ser
        195                 200                 205 cac agc agc ttc agc tgc ctg gtc acg cac cag ggg agc acc gtg gag    672
His Ser Ser Phe Ser Cys Leu Val Thr His Gln Gly Ser Thr Val Glu
    210                 215                 220 aag aag gtg gcc cct gca gag tgc tct taggtccctg agaattcctg          719
Lys Lys Val Ala Pro Ala Glu Cys Ser
225                 230 agatggagcc ttcctcaccc agacacccct tccccagttc accttgtgcc cctgaaaacc    779
caccctggac cagctcagac caggcaggtc actcatcctc cctgtttcta cttgtgctca    839
ataaagactt tatcatttat cactg                                          864

<210> SEQ ID NO 59
<211> LENGTH: 233
<212> TYPE: PRT
<213> ORGANISM: Canis familiaris

<400> SEQUENCE: 59
```

```
Met Ala Trp Thr Leu Leu Leu Gly Phe Leu Ala His Cys Thr Gly
1               5                   10                  15

Ser Val Ala Ser Tyr Val Leu Thr Gln Ser Pro Ser Val Ser Val Thr
            20                  25                  30

Leu Gly Gln Thr Ala Ser Ile Thr Cys Arg Gly Asn Ser Ile Gly Arg
        35                  40                  45

Lys Asp Val His Trp Tyr Gln Gln Lys Pro Gly Gln Ala Pro Leu Leu
    50                  55                  60

Ile Ile Tyr Asn Asp Asn Ser Gln Pro Ser Gly Ile Pro Glu Arg Phe
65                  70                  75                  80

Ser Gly Thr Asn Ser Gly Ser Thr Ala Thr Leu Thr Ile Ser Glu Ala
            85                  90                  95

Gln Thr Asn Asp Glu Ala Asp Tyr Tyr Cys Gln Val Trp Glu Ser Ser
            100                 105                 110

Ala Asp Cys Trp Val Phe Gly Glu Gly Thr Gln Leu Thr Val Leu Gly
            115                 120                 125

Gln Pro Lys Ser Ser Pro Leu Val Thr Leu Phe Pro Pro Ser Ser Glu
    130                 135                 140

Glu Leu Gly Ala Asn Lys Ala Thr Leu Val Cys Leu Ile Ser Asp Phe
145                 150                 155                 160

Tyr Pro Ser Gly Leu Lys Val Ala Trp Lys Ala Asp Gly Ser Thr Ile
                165                 170                 175

Ile Gln Gly Val Glu Thr Thr Lys Pro Ser Lys Gln Ser Asn Asn Lys
            180                 185                 190

Tyr Thr Ala Ser Ser Tyr Leu Ser Leu Thr Pro Asp Lys Trp Lys Ser
            195                 200                 205

His Ser Ser Phe Ser Cys Leu Val Thr His Gln Gly Ser Thr Val Glu
    210                 215                 220

Lys Lys Val Ala Pro Ala Glu Cys Ser
225                 230

<210> SEQ ID NO 60
<211> LENGTH: 864
<212> TYPE: DNA
<213> ORGANISM: Canis familiaris
<220> FEATURE:
<221> NAME/KEY: CDS
<222> LOCATION: (1)..(699)

<400> SEQUENCE: 60 atg gcc tgg acc ctt ctt ctc ctt gga ttc ctg gct cac tgc aca ggt      48
Met Ala Trp Thr Leu Leu Leu Leu Gly Phe Leu Ala His Cys Thr Gly
1               5                   10                  15 tcc gtg gcc tcc tat gtg ctg act cag tca ccc tca gtg tca gtg acc      96
Ser Val Ala Ser Tyr Val Leu Thr Gln Ser Pro Ser Val Ser Val Thr
            20                  25                  30 ctg gga cag acg gcc agc atc acc tgt agg gga aac agc att gga agg     144
Leu Gly Gln Thr Ala Ser Ile Thr Cys Arg Gly Asn Ser Ile Gly Arg
        35                  40                  45 aaa gat gtt cat tgg tac cag cag aag ccg ggc caa gcc ccc ctg ctg     192
Lys Asp Val His Trp Tyr Gln Gln Lys Pro Gly Gln Ala Pro Leu Leu
    50                  55                  60 att atc tat aat gat aac agc cag ccc tca ggg atc cct gag cga ttc     240
Ile Ile Tyr Asn Asp Asn Ser Gln Pro Ser Gly Ile Pro Glu Arg Phe
65                  70                  75                  80 tct ggg acc aac tca ggg agc acg gcc acc ctg acc atc agt gag gcc     288
Ser Gly Thr Asn Ser Gly Ser Thr Ala Thr Leu Thr Ile Ser Glu Ala
            85                  90                  95
```

```
caa acc aac gat gag gct gac tat tac tgc cag gtg tgg gaa agt agc    336
Gln Thr Asn Asp Glu Ala Asp Tyr Tyr Cys Gln Val Trp Glu Ser Ser
            100                 105                 110 gct gat gct cac aac aac tct gga aga aaa att gga gca cct ggc agt    384
Ala Asp Ala His Asn Asn Ser Gly Arg Lys Ile Gly Ala Pro Gly Ser
        115                 120                 125 cag ccc aag tcc tcc ccc ttg gtc aca ctc ttc ccg ccc tcc tct gag    432
Gln Pro Lys Ser Ser Pro Leu Val Thr Leu Phe Pro Pro Ser Ser Glu
    130                 135                 140 gag ctc ggc gcc aac aag gct acc ctg gtg tgc ctc atc agc gac ttc    480
Glu Leu Gly Ala Asn Lys Ala Thr Leu Val Cys Leu Ile Ser Asp Phe
145                 150                 155                 160 tac ccc agt ggc ctg aaa gtg gct tgg aag gca gat ggc agc acc atc    528
Tyr Pro Ser Gly Leu Lys Val Ala Trp Lys Ala Asp Gly Ser Thr Ile
                165                 170                 175 atc cag ggc gtg gaa acc acc aag ccc tcc aag cag agc aac aac aag    576
Ile Gln Gly Val Glu Thr Thr Lys Pro Ser Lys Gln Ser Asn Asn Lys
            180                 185                 190 tac acg gcc agc agc tac ctg agc ctg acg cct gac aag tgg aaa tct    624
Tyr Thr Ala Ser Ser Tyr Leu Ser Leu Thr Pro Asp Lys Trp Lys Ser
        195                 200                 205 cac agc agc ttc agc tgc ctg gtc acg cac cag ggg agc acc gtg gag    672
His Ser Ser Phe Ser Cys Leu Val Thr His Gln Gly Ser Thr Val Glu
    210                 215                 220 aag aag gtg gcc cct gca gag tgc tct taggtccctg agaattcctg          719
Lys Lys Val Ala Pro Ala Glu Cys Ser
225                 230 agatggagcc ttcctcaccc agacacccct tccccagttc accttgtgcc cctgaaaacc    779
caccctggac cagctcagac caggcaggtc actcatcctc cctgtttcta cttgtgctca    839
ataaagactt tatcatttat cactg                                         864

<210> SEQ ID NO 61
<211> LENGTH: 233
<212> TYPE: PRT
<213> ORGANISM: Canis familiaris

<400> SEQUENCE: 61

Met Ala Trp Thr Leu Leu Leu Gly Phe Leu Ala His Cys Thr Gly
1               5                   10                  15

Ser Val Ala Ser Tyr Val Leu Thr Gln Ser Pro Ser Val Ser Val Thr
            20                  25                  30

Leu Gly Gln Thr Ala Ser Ile Thr Cys Arg Gly Asn Ser Ile Gly Arg
        35                  40                  45

Lys Asp Val His Trp Tyr Gln Gln Lys Pro Gly Gln Ala Pro Leu Leu
    50                  55                  60

Ile Ile Tyr Asn Asp Asn Ser Gln Pro Ser Gly Ile Pro Glu Arg Phe
65                  70                  75                  80

Ser Gly Thr Asn Ser Gly Ser Thr Ala Thr Leu Thr Ile Ser Glu Ala
                85                  90                  95

Gln Thr Asn Asp Glu Ala Asp Tyr Tyr Cys Gln Val Trp Glu Ser Ser
            100                 105                 110

Ala Asp Ala His Asn Asn Ser Gly Arg Lys Ile Gly Ala Pro Gly Ser
        115                 120                 125

Gln Pro Lys Ser Ser Pro Leu Val Thr Leu Phe Pro Pro Ser Ser Glu
    130                 135                 140

Glu Leu Gly Ala Asn Lys Ala Thr Leu Val Cys Leu Ile Ser Asp Phe
```

```
                    145                 150                 155                 160
Tyr Pro Ser Gly Leu Lys Val Ala Trp Lys Ala Asp Gly Ser Thr Ile
                165                 170                 175

Ile Gln Gly Val Glu Thr Thr Lys Pro Ser Lys Gln Ser Asn Asn Lys
            180                 185                 190

Tyr Thr Ala Ser Ser Tyr Leu Ser Leu Thr Pro Asp Lys Trp Lys Ser
        195                 200                 205

His Ser Ser Phe Ser Cys Leu Val Thr His Gln Gly Ser Thr Val Glu
    210                 215                 220

Lys Lys Val Ala Pro Ala Glu Cys Ser
225                 230

<210> SEQ ID NO 62
<211> LENGTH: 867
<212> TYPE: DNA
<213> ORGANISM: Canis familiaris
<220> FEATURE:
<221> NAME/KEY: CDS
<222> LOCATION: (1)..(702)

<400> SEQUENCE: 62 atg gcc tgg acc ctt ctt ctc ctt gga ttc ctg gct cac tgc aca ggt        48
Met Ala Trp Thr Leu Leu Leu Leu Gly Phe Leu Ala His Cys Thr Gly
1               5                   10                  15 tcc gtg gcc tcc tat gtg ctg act cag tca ccc tca gtg tca gtg acc        96
Ser Val Ala Ser Tyr Val Leu Thr Gln Ser Pro Ser Val Ser Val Thr
                20                  25                  30 ctg gga cag acg gcc agc atc acc tgt agg gga aac agc att gga agg       144
Leu Gly Gln Thr Ala Ser Ile Thr Cys Arg Gly Asn Ser Ile Gly Arg
            35                  40                  45 aaa gat gtt cat tgg tac cag cag aag ccg ggc caa gcc ccc ctg ctg       192
Lys Asp Val His Trp Tyr Gln Gln Lys Pro Gly Gln Ala Pro Leu Leu
        50                  55                  60 att atc tat aat gat aac agc cag ccc tca ggg atc cct gag cga ttc       240
Ile Ile Tyr Asn Asp Asn Ser Gln Pro Ser Gly Ile Pro Glu Arg Phe
65                  70                  75                  80 tct ggg acc aac tca ggg agc acg gcc acc ctg acc atc agt gag gcc       288
Ser Gly Thr Asn Ser Gly Ser Thr Ala Thr Leu Thr Ile Ser Glu Ala
                85                  90                  95 caa acc aac gat gag gct gac tat tac tgc cag gtg tgg gaa agt agc       336
Gln Thr Asn Asp Glu Ala Asp Tyr Tyr Cys Gln Val Trp Glu Ser Ser
            100                 105                 110 agt aaa aat tgt tgg gta ttc ggt gaa ggg acc cag ctg acc gtc ctc       384
Ser Lys Asn Cys Trp Val Phe Gly Glu Gly Thr Gln Leu Thr Val Leu
        115                 120                 125 ggt cag ccc aag tcc tcc ccc ttg gtc aca ctc ttc ccg ccc tcc tct       432
Gly Gln Pro Lys Ser Ser Pro Leu Val Thr Leu Phe Pro Pro Ser Ser
130                 135                 140 gag gag ctc ggc gcc aac aag gct acc ctg gtg tgc ctc atc agc gac       480
Glu Glu Leu Gly Ala Asn Lys Ala Thr Leu Val Cys Leu Ile Ser Asp
145                 150                 155                 160 ttc tac ccc agt ggc ctg aaa gtg gct tgg aag gca gat ggc agc acc       528
Phe Tyr Pro Ser Gly Leu Lys Val Ala Trp Lys Ala Asp Gly Ser Thr
                165                 170                 175 atc atc cag ggc gtg gaa acc acc aag ccc tcc aag cag agc aac aac       576
Ile Ile Gln Gly Val Glu Thr Thr Lys Pro Ser Lys Gln Ser Asn Asn
            180                 185                 190 aag tac acg gcc agc agc tac ctg agc ctg acg cct gac aag tgg aaa       624
Lys Tyr Thr Ala Ser Ser Tyr Leu Ser Leu Thr Pro Asp Lys Trp Lys
        195                 200                 205
```

```
tct cac agc agc ttc agc tgc ctg gtc acg cac cag ggg agc acc gtg      672
Ser His Ser Ser Phe Ser Cys Leu Val Thr His Gln Gly Ser Thr Val
    210                 215                 220 gag aag aag gtg gcc cct gca gag tgc tct taggtccctg agaattcctg        722
Glu Lys Lys Val Ala Pro Ala Glu Cys Ser
225                 230 agatggagcc ttcctcaccc agacacccct tccccagttc accttgtgcc cctgaaaacc    782
caccctggac cagctcagac caggcaggtc actcatcctc cctgtttcta cttgtgctca    842
ataaagactt tatcatttat cactg                                          867
```

<210> SEQ ID NO 63
<211> LENGTH: 234
<212> TYPE: PRT
<213> ORGANISM: Canis familiaris

<400> SEQUENCE: 63

```
Met Ala Trp Thr Leu Leu Leu Gly Phe Leu Ala His Cys Thr Gly
1               5                   10                  15

Ser Val Ala Ser Tyr Val Leu Thr Gln Ser Pro Ser Val Ser Val Thr
            20                  25                  30

Leu Gly Gln Thr Ala Ser Ile Thr Cys Arg Gly Asn Ser Ile Gly Arg
        35                  40                  45

Lys Asp Val His Trp Tyr Gln Gln Lys Pro Gly Gln Ala Pro Leu Leu
    50                  55                  60

Ile Ile Tyr Asn Asp Asn Ser Gln Pro Ser Gly Ile Pro Glu Arg Phe
65                  70                  75                  80

Ser Gly Thr Asn Ser Gly Ser Thr Ala Thr Leu Thr Ile Ser Glu Ala
                85                  90                  95

Gln Thr Asn Asp Glu Ala Asp Tyr Tyr Cys Gln Val Trp Glu Ser Ser
            100                 105                 110

Ser Lys Asn Cys Trp Val Phe Gly Glu Gly Thr Gln Leu Thr Val Leu
        115                 120                 125

Gly Gln Pro Lys Ser Ser Pro Leu Val Thr Leu Phe Pro Pro Ser Ser
    130                 135                 140

Glu Glu Leu Gly Ala Asn Lys Ala Thr Leu Val Cys Leu Ile Ser Asp
145                 150                 155                 160

Phe Tyr Pro Ser Gly Leu Lys Val Ala Trp Lys Ala Asp Gly Ser Thr
                165                 170                 175

Ile Ile Gln Gly Val Glu Thr Thr Lys Pro Ser Lys Gln Ser Asn Asn
            180                 185                 190

Lys Tyr Thr Ala Ser Ser Tyr Leu Ser Leu Thr Pro Asp Lys Trp Lys
        195                 200                 205

Ser His Ser Ser Phe Ser Cys Leu Val Thr His Gln Gly Ser Thr Val
    210                 215                 220

Glu Lys Lys Val Ala Pro Ala Glu Cys Ser
225                 230
```

<210> SEQ ID NO 64
<211> LENGTH: 861
<212> TYPE: DNA
<213> ORGANISM: Canis familiaris
<220> FEATURE:
<221> NAME/KEY: CDS
<222> LOCATION: (1)..(696)

<400> SEQUENCE: 64

-continued

| | | |
|---|---|---|
| atg gcc tgg acc ctt ctt ctc ctt gga ttc ctg gct cac tgc aca ggt<br>Met Ala Trp Thr Leu Leu Leu Leu Gly Phe Leu Ala His Cys Thr Gly<br>1               5                   10                  15 | | 48 |
| tcc gtg gcc tcc tat gtg ctg act cag tca ccc tca gtg tca gtg acc<br>Ser Val Ala Ser Tyr Val Leu Thr Gln Ser Pro Ser Val Ser Val Thr<br>            20                  25                  30 | | 96 |
| ctg gga cag acg gcc agc atc acc tgt agg gga aac agc att gga agg<br>Leu Gly Gln Thr Ala Ser Ile Thr Cys Arg Gly Asn Ser Ile Gly Arg<br>        35                  40                  45 | | 144 |
| aaa gat gtt cat tgg tac cag cag aag ccg ggc caa gcc ccc ctg ctg<br>Lys Asp Val His Trp Tyr Gln Gln Lys Pro Gly Gln Ala Pro Leu Leu<br>50                  55                  60 | | 192 |
| att atc tat aat gat aac agc cag ccc tca ggg atc cct gag cga ttc<br>Ile Ile Tyr Asn Asp Asn Ser Gln Pro Ser Gly Ile Pro Glu Arg Phe<br>65                  70                  75                  80 | | 240 |
| tct ggg acc aac tca ggg agc acg gcc acc ctg acc atc agt gag gcc<br>Ser Gly Thr Asn Ser Gly Ser Thr Ala Thr Leu Thr Ile Ser Glu Ala<br>                85                  90                  95 | | 288 |
| caa acc aac gat gag gct gac tat tac tgc cag gtg tgg gaa aat aaa<br>Gln Thr Asn Asp Glu Ala Asp Tyr Tyr Cys Gln Val Trp Glu Asn Lys<br>            100                 105                 110 | | 336 |
| tat tgt tgg gta ttc ggt gaa ggg acc cag ctg acc gtc ctc ggt cag<br>Tyr Cys Trp Val Phe Gly Glu Gly Thr Gln Leu Thr Val Leu Gly Gln<br>        115                 120                 125 | | 384 |
| ccc aag tcc tcc ccc ttg gtc aca ctc ttc ccg ccc tcc tct gag gag<br>Pro Lys Ser Ser Pro Leu Val Thr Leu Phe Pro Pro Ser Ser Glu Glu<br>130                 135                 140 | | 432 |
| ctc ggc gcc aac aag gct acc ctg gtg tgc ctc atc agc gac ttc tac<br>Leu Gly Ala Asn Lys Ala Thr Leu Val Cys Leu Ile Ser Asp Phe Tyr<br>145                 150                 155                 160 | | 480 |
| ccc agt ggc ctg aaa gtg gct tgg aag gca gat ggc agc acc atc atc<br>Pro Ser Gly Leu Lys Val Ala Trp Lys Ala Asp Gly Ser Thr Ile Ile<br>                165                 170                 175 | | 528 |
| cag ggc gtg gaa acc acc aag ccc tcc aag cag agc aac aac aag tac<br>Gln Gly Val Glu Thr Thr Lys Pro Ser Lys Gln Ser Asn Asn Lys Tyr<br>            180                 185                 190 | | 576 |
| acg gcc agc agc tac ctg agc ctg acg cct gac aag tgg aaa tct cac<br>Thr Ala Ser Ser Tyr Leu Ser Leu Thr Pro Asp Lys Trp Lys Ser His<br>        195                 200                 205 | | 624 |
| agc agc ttc agc tgc ctg gtc acg cac cag ggg agc acc gtg gag aag<br>Ser Ser Phe Ser Cys Leu Val Thr His Gln Gly Ser Thr Val Glu Lys<br>    210                 215                 220 | | 672 |
| aag gtg gcc cct gca gag tgc tct taggtccctg agaattcctg agatggagcc<br>Lys Val Ala Pro Ala Glu Cys Ser<br>225                 230 | | 726 |
| ttcctcaccc agacacccct tccccagttc accttgtgcc cctgaaaacc caccctggac | | 786 |
| cagctcagac caggcaggtc actcatcctc cctgtttcta cttgtgctca ataaagactt | | 846 |
| tatcatttat cactg | | 861 |

<210> SEQ ID NO 65
<211> LENGTH: 232
<212> TYPE: PRT
<213> ORGANISM: Canis familiaris

<400> SEQUENCE: 65

Met Ala Trp Thr Leu Leu Leu Leu Gly Phe Leu Ala His Cys Thr Gly
1               5                   10                  15

Ser Val Ala Ser Tyr Val Leu Thr Gln Ser Pro Ser Val Ser Val Thr
            20                  25                  30

```
Leu Gly Gln Thr Ala Ser Ile Thr Cys Arg Gly Asn Ser Ile Gly Arg
         35                  40                  45

Lys Asp Val His Trp Tyr Gln Gln Lys Pro Gly Gln Ala Pro Leu Leu
 50                  55                  60

Ile Ile Tyr Asn Asp Asn Ser Gln Pro Ser Gly Ile Pro Glu Arg Phe
 65                  70                  75                  80

Ser Gly Thr Asn Ser Gly Ser Thr Ala Thr Leu Thr Ile Ser Glu Ala
                 85                  90                  95

Gln Thr Asn Asp Glu Ala Asp Tyr Tyr Cys Gln Val Trp Glu Asn Lys
                100                 105                 110

Tyr Cys Trp Val Phe Gly Glu Gly Thr Gln Leu Thr Val Leu Gly Gln
            115                 120                 125

Pro Lys Ser Ser Pro Leu Val Thr Leu Phe Pro Pro Ser Ser Glu Glu
        130                 135                 140

Leu Gly Ala Asn Lys Ala Thr Leu Val Cys Leu Ile Ser Asp Phe Tyr
145                 150                 155                 160

Pro Ser Gly Leu Lys Val Ala Trp Lys Ala Asp Gly Ser Thr Ile Ile
                165                 170                 175

Gln Gly Val Glu Thr Thr Lys Pro Ser Lys Gln Ser Asn Asn Lys Tyr
            180                 185                 190

Thr Ala Ser Ser Tyr Leu Ser Leu Thr Pro Asp Lys Trp Lys Ser His
        195                 200                 205

Ser Ser Phe Ser Cys Leu Val Thr His Gln Gly Ser Thr Val Glu Lys
210                 215                 220

Lys Val Ala Pro Ala Glu Cys Ser
225                 230

<210> SEQ ID NO 66
<211> LENGTH: 861
<212> TYPE: DNA
<213> ORGANISM: Canis familiaris
<220> FEATURE:
<221> NAME/KEY: CDS
<222> LOCATION: (1)..(696)

<400> SEQUENCE: 66 atg gcc tgg acc ctt ctt ctc ctt gga ttc ctg gct cac tgc aca ggt    48
Met Ala Trp Thr Leu Leu Leu Leu Gly Phe Leu Ala His Cys Thr Gly
 1               5                  10                  15 tcc gtg gcc tcc tat gtg ctg act cag tca ccc tca gtg tca gtg acc    96
Ser Val Ala Ser Tyr Val Leu Thr Gln Ser Pro Ser Val Ser Val Thr
                20                  25                  30 ctg gga cag acg gcc agc atc acc tgt agg gga aac agc att gga agg   144
Leu Gly Gln Thr Ala Ser Ile Thr Cys Arg Gly Asn Ser Ile Gly Arg
            35                  40                  45 aaa gat gtt cat tgg tac cag cag aag ccg ggc caa gcc ccc ctg ctg   192
Lys Asp Val His Trp Tyr Gln Gln Lys Pro Gly Gln Ala Pro Leu Leu
 50                  55                  60 att atc tat aat gat aac agc cag ccc tca ggg atc cct gag cga ttc   240
Ile Ile Tyr Asn Asp Asn Ser Gln Pro Ser Gly Ile Pro Glu Arg Phe
 65                  70                  75                  80 tct ggg acc aac tca ggg agc acg gcc acc ctg acc atc agt gag gcc   288
Ser Gly Thr Asn Ser Gly Ser Thr Ala Thr Leu Thr Ile Ser Glu Ala
                 85                  90                  95 caa acc aac gat gag gct gac tat tac tgc cag gtg tgg gaa atc tct   336
Gln Thr Asn Asp Glu Ala Asp Tyr Tyr Cys Gln Val Trp Glu Ile Ser
                100                 105                 110
```

-continued

| | | |
|---|---|---|
| gtg tgt tgg gta ttc ggt gaa ggg acc cag ctg acc gtc ctc ggt cag<br>Val Cys Trp Val Phe Gly Glu Gly Thr Gln Leu Thr Val Leu Gly Gln<br>115 120 125 | | 384 |
| ccc aag tcc tcc ccc ttg gtc aca ctc ttc ccg ccc tcc tct gag gag<br>Pro Lys Ser Ser Pro Leu Val Thr Leu Phe Pro Pro Ser Ser Glu Glu<br>130 135 140 | | 432 |
| ctc ggc gcc aac aag gct acc ctg gtg tgc ctc atc agc gac ttc tac<br>Leu Gly Ala Asn Lys Ala Thr Leu Val Cys Leu Ile Ser Asp Phe Tyr<br>145 150 155 160 | | 480 |
| ccc agt ggc ctg aaa gtg gct tgg aag gca gat ggc agc acc atc atc<br>Pro Ser Gly Leu Lys Val Ala Trp Lys Ala Asp Gly Ser Thr Ile Ile<br>165 170 175 | | 528 |
| cag ggc gtg gaa acc acc aag ccc tcc aag cag agc aac aac aag tac<br>Gln Gly Val Glu Thr Thr Lys Pro Ser Lys Gln Ser Asn Asn Lys Tyr<br>180 185 190 | | 576 |
| acg gcc agc agc tac ctg agc ctg acg cct gac aag tgg aaa tct cac<br>Thr Ala Ser Ser Tyr Leu Ser Leu Thr Pro Asp Lys Trp Lys Ser His<br>195 200 205 | | 624 |
| agc agc ttc agc tgc ctg gtc acg cac cag ggg agc acc gtg gag aag<br>Ser Ser Phe Ser Cys Leu Val Thr His Gln Gly Ser Thr Val Glu Lys<br>210 215 220 | | 672 |
| aag gtg gcc cct gca gag tgc tct taggtccctg agaattcctg agatggagcc<br>Lys Val Ala Pro Ala Glu Cys Ser<br>225 230 | | 726 |
| ttcctcaccc agacacccct tccccagttc accttgtgcc cctgaaaacc caccctggac | | 786 |
| cagctcagac caggcaggtc actcatcctc cctgtttcta cttgtgctca ataaagactt | | 846 |
| tatcatttat cactg | | 861 |

<210> SEQ ID NO 67
<211> LENGTH: 232
<212> TYPE: PRT
<213> ORGANISM: Canis familiaris

<400> SEQUENCE: 67

Met Ala Trp Thr Leu Leu Leu Gly Phe Leu Ala His Cys Thr Gly
1               5                   10                  15

Ser Val Ala Ser Tyr Val Leu Thr Gln Ser Pro Ser Val Ser Val Thr
            20                  25                  30

Leu Gly Gln Thr Ala Ser Ile Thr Cys Arg Gly Asn Ser Ile Gly Arg
        35                  40                  45

Lys Asp Val His Trp Tyr Gln Gln Lys Pro Gly Gln Ala Pro Leu Leu
    50                  55                  60

Ile Ile Tyr Asn Asp Asn Ser Gln Pro Ser Gly Ile Pro Glu Arg Phe
65                  70                  75                  80

Ser Gly Thr Asn Ser Gly Ser Thr Ala Thr Leu Thr Ile Ser Glu Ala
                85                  90                  95

Gln Thr Asn Asp Glu Ala Asp Tyr Tyr Cys Gln Val Trp Glu Ile Ser
            100                 105                 110

Val Cys Trp Val Phe Gly Glu Gly Thr Gln Leu Thr Val Leu Gly Gln
        115                 120                 125

Pro Lys Ser Ser Pro Leu Val Thr Leu Phe Pro Pro Ser Ser Glu Glu
    130                 135                 140

Leu Gly Ala Asn Lys Ala Thr Leu Val Cys Leu Ile Ser Asp Phe Tyr
145                 150                 155                 160

Pro Ser Gly Leu Lys Val Ala Trp Lys Ala Asp Gly Ser Thr Ile Ile
                165                 170                 175

-continued

```
Gln Gly Val Glu Thr Thr Lys Pro Ser Lys Gln Ser Asn Asn Lys Tyr
            180                 185                 190

Thr Ala Ser Ser Tyr Leu Ser Leu Thr Pro Asp Lys Trp Lys Ser His
        195                 200                 205

Ser Ser Phe Ser Cys Leu Val Thr His Gln Gly Ser Thr Val Glu Lys
    210                 215                 220

Lys Val Ala Pro Ala Glu Cys Ser
225                 230
```

<210> SEQ ID NO 68
<211> LENGTH: 867
<212> TYPE: DNA
<213> ORGANISM: Canis familiaris
<220> FEATURE:
<221> NAME/KEY: CDS
<222> LOCATION: (1)..(702)

<400> SEQUENCE: 68

| | |
|---|---|
| atg gcc tgg acc ctt ctt ctc ctt gga ttc ctg gct cac tgc aca ggt<br>Met Ala Trp Thr Leu Leu Leu Leu Gly Phe Leu Ala His Cys Thr Gly<br>1               5                   10                  15 | 48 |
| tcc gtg gcc tcc tat gtg ctg act cag tca ccc tca gtg tca gtg acc<br>Ser Val Ala Ser Tyr Val Leu Thr Gln Ser Pro Ser Val Ser Val Thr<br>            20                  25                  30 | 96 |
| ctg gga cag acg gcc agc atc acc tgt agg gga aac agc att gga agg<br>Leu Gly Gln Thr Ala Ser Ile Thr Cys Arg Gly Asn Ser Ile Gly Arg<br>        35                  40                  45 | 144 |
| aaa gat gtt cat tgg tac cag cag aag ccg ggc caa gcc ccc ctg ctg<br>Lys Asp Val His Trp Tyr Gln Gln Lys Pro Gly Gln Ala Pro Leu Leu<br>    50                  55                  60 | 192 |
| att atc tat aat gat aac agc cag ccc tca ggg atc cct gag cga ttc<br>Ile Ile Tyr Asn Asp Asn Ser Gln Pro Ser Gly Ile Pro Glu Arg Phe<br>65                  70                  75                  80 | 240 |
| tct ggg acc aac tca ggg agc acg gcc acc ctg acc atc agt gag gcc<br>Ser Gly Thr Asn Ser Gly Ser Thr Ala Thr Leu Thr Ile Ser Glu Ala<br>                85                  90                  95 | 288 |
| caa acc aac gat gag gct gac tat tac tgc cag gag atg cac aca cct<br>Gln Thr Asn Asp Glu Ala Asp Tyr Tyr Cys Gln Glu Met His Thr Pro<br>            100                 105                 110 | 336 |
| gaa tca cag tgt tgg gta ttc ggt gaa ggg acc cag ctg acc gtc ctc<br>Glu Ser Gln Cys Trp Val Phe Gly Glu Gly Thr Gln Leu Thr Val Leu<br>        115                 120                 125 | 384 |
| ggt cag ccc aag tcc tcc ccc ttg gtc aca ctc ttc ccg ccc tcc tct<br>Gly Gln Pro Lys Ser Ser Pro Leu Val Thr Leu Phe Pro Pro Ser Ser<br>    130                 135                 140 | 432 |
| gag gag ctc ggc gcc aac aag gct acc ctg gtg tgc ctc atc agc gac<br>Glu Glu Leu Gly Ala Asn Lys Ala Thr Leu Val Cys Leu Ile Ser Asp<br>145                 150                 155                 160 | 480 |
| ttc tac ccc agt ggc ctg aaa gtg gct tgg aag gca gat ggc agc acc<br>Phe Tyr Pro Ser Gly Leu Lys Val Ala Trp Lys Ala Asp Gly Ser Thr<br>                165                 170                 175 | 528 |
| atc atc cag ggc gtg gaa acc acc aag ccc tcc aag cag agc aac aac<br>Ile Ile Gln Gly Val Glu Thr Thr Lys Pro Ser Lys Gln Ser Asn Asn<br>            180                 185                 190 | 576 |
| aag tac acg gcc agc agc tac ctg agc ctg acg cct gac aag tgg aaa<br>Lys Tyr Thr Ala Ser Ser Tyr Leu Ser Leu Thr Pro Asp Lys Trp Lys<br>        195                 200                 205 | 624 |
| tct cac agc agc ttc agc tgc ctg gtc acg cac cag ggg agc acc gtg<br>Ser His Ser Ser Phe Ser Cys Leu Val Thr His Gln Gly Ser Thr Val<br>    210                 215                 220 | 672 |

```
gag aag aag gtg gcc cct gca gag tgc tct taggtccctg agaattcctg    722
Glu Lys Lys Val Ala Pro Ala Glu Cys Ser
225                 230 agatggagcc ttcctcaccc agacacccct tccccagttc accttgtgcc ctgaaaacc    782 caccctggac cagctcagac caggcaggtc actcatcctc cctgtttcta cttgtgctca    842
ataaagactt tatcatttat cactg    867
```

<210> SEQ ID NO 69
<211> LENGTH: 234
<212> TYPE: PRT
<213> ORGANISM: Canis familiaris

<400> SEQUENCE: 69

```
Met Ala Trp Thr Leu Leu Leu Leu Gly Phe Leu Ala His Cys Thr Gly
1               5                   10                  15

Ser Val Ala Ser Tyr Val Leu Thr Gln Ser Pro Ser Val Ser Val Thr
            20                  25                  30

Leu Gly Gln Thr Ala Ser Ile Thr Cys Arg Gly Asn Ser Ile Gly Arg
        35                  40                  45

Lys Asp Val His Trp Tyr Gln Gln Lys Pro Gly Gln Ala Pro Leu Leu
    50                  55                  60

Ile Ile Tyr Asn Asp Asn Ser Gln Pro Ser Gly Ile Pro Glu Arg Phe
65                  70                  75                  80

Ser Gly Thr Asn Ser Gly Ser Thr Ala Thr Leu Thr Ile Ser Glu Ala
                85                  90                  95

Gln Thr Asn Asp Glu Ala Asp Tyr Tyr Cys Gln Glu Met His Thr Pro
            100                 105                 110

Glu Ser Gln Cys Trp Val Phe Gly Glu Gly Thr Gln Leu Thr Val Leu
        115                 120                 125

Gly Gln Pro Lys Ser Ser Pro Leu Val Thr Leu Phe Pro Pro Ser Ser
130                 135                 140

Glu Glu Leu Gly Ala Asn Lys Ala Thr Leu Val Cys Leu Ile Ser Asp
145                 150                 155                 160

Phe Tyr Pro Ser Gly Leu Lys Val Ala Trp Lys Ala Asp Gly Ser Thr
                165                 170                 175

Ile Ile Gln Gly Val Glu Thr Thr Lys Pro Ser Lys Gln Ser Asn Asn
            180                 185                 190

Lys Tyr Thr Ala Ser Ser Tyr Leu Ser Leu Thr Pro Asp Lys Trp Lys
        195                 200                 205

Ser His Ser Ser Phe Ser Cys Leu Val Thr His Gln Gly Ser Thr Val
    210                 215                 220

Glu Lys Lys Val Ala Pro Ala Glu Cys Ser
225                 230
```

<210> SEQ ID NO 70
<211> LENGTH: 861
<212> TYPE: DNA
<213> ORGANISM: Canis familiaris
<220> FEATURE:
<221> NAME/KEY: CDS
<222> LOCATION: (1)..(696)

<400> SEQUENCE: 70

```
atg gcc tgg acc ctt ctt ctc ctt gga ttc ctg gct cac tgc aca ggt    48
Met Ala Trp Thr Leu Leu Leu Leu Gly Phe Leu Ala His Cys Thr Gly
1               5                   10                  15 tcc gtg gcc tcc tat gtg ctg act cag tca ccc tca gtg tca gtg acc    96
```

```
ctg gga cag acg gcc agc atc acc tgt agg gga aac agc att gga agg    144
Leu Gly Gln Thr Ala Ser Ile Thr Cys Arg Gly Asn Ser Ile Gly Arg
        35                  40                  45 aaa gat gtt cat tgg tac cag cag aag ccg ggc caa gcc ccc ctg ctg    192
Lys Asp Val His Trp Tyr Gln Gln Lys Pro Gly Gln Ala Pro Leu Leu
 50                  55                  60 att atc tat aat gat aac agc cag ccc tca ggg atc cct gag cga ttc    240
Ile Ile Tyr Asn Asp Asn Ser Gln Pro Ser Gly Ile Pro Glu Arg Phe
65                  70                  75                  80 tct ggg acc aac tca ggg agc acg gcc acc ctg acc atc agt gag gcc    288
Ser Gly Thr Asn Ser Gly Ser Thr Ala Thr Leu Thr Ile Ser Glu Ala
                85                  90                  95 caa acc aac gat gag gct gac tat tac tgc cag cat tac cac cat gac    336
Gln Thr Asn Asp Glu Ala Asp Tyr Tyr Cys Gln His Tyr His His Asp
            100                 105                 110 tat tgt tgg gta ttc ggt gaa ggg acc cag ctg acc gtc ctc ggt cag    384
Tyr Cys Trp Val Phe Gly Glu Gly Thr Gln Leu Thr Val Leu Gly Gln
        115                 120                 125 ccc aag tcc tcc ccc ttg gtc aca ctc ttc ccg ccc tcc tct gag gag    432
Pro Lys Ser Ser Pro Leu Val Thr Leu Phe Pro Pro Ser Ser Glu Glu
130                 135                 140 ctc ggc gcc aac aag gct acc ctg gtg tgc ctc atc agc gac ttc tac    480
Leu Gly Ala Asn Lys Ala Thr Leu Val Cys Leu Ile Ser Asp Phe Tyr
145                 150                 155                 160 ccc agt ggc ctg aaa gtg gct tgg aag gca gat ggc agc acc atc atc    528
Pro Ser Gly Leu Lys Val Ala Trp Lys Ala Asp Gly Ser Thr Ile Ile
                165                 170                 175 cag ggc gtg gaa acc acc aag ccc tcc aag cag agc aac aac aag tac    576
Gln Gly Val Glu Thr Thr Lys Pro Ser Lys Gln Ser Asn Asn Lys Tyr
            180                 185                 190 acg gcc agc agc tac ctg agc ctg acg cct gac aag tgg aaa tct cac    624
Thr Ala Ser Ser Tyr Leu Ser Leu Thr Pro Asp Lys Trp Lys Ser His
        195                 200                 205 agc agc ttc agc tgc ctg gtc acg cac cag ggg agc acc gtg gag aag    672
Ser Ser Phe Ser Cys Leu Val Thr His Gln Gly Ser Thr Val Glu Lys
210                 215                 220 aag gtg gcc cct gca gag tgc tct taggtccctg agaattcctg agatggagcc   726
Lys Val Ala Pro Ala Glu Cys Ser
225                 230 ttcctcaccc agacacccct tccccagttc accttgtgcc cctgaaaacc cacccctggac   786 cagctcagac caggcaggtc actcatcctc cctgtttcta cttgtgctca ataaagactt   846
tatcatttat cactg                                                   861
```

<210> SEQ ID NO 71
<211> LENGTH: 232
<212> TYPE: PRT
<213> ORGANISM: Canis familiaris

<400> SEQUENCE: 71

```
Met Ala Trp Thr Leu Leu Leu Leu Gly Phe Leu Ala His Cys Thr Gly
1               5                   10                  15

Ser Val Ala Ser Tyr Val Leu Thr Gln Ser Pro Ser Val Ser Val Thr
            20                  25                  30

Leu Gly Gln Thr Ala Ser Ile Thr Cys Arg Gly Asn Ser Ile Gly Arg
        35                  40                  45

Lys Asp Val His Trp Tyr Gln Gln Lys Pro Gly Gln Ala Pro Leu Leu
```

```
            50                  55                  60
Ile Ile Tyr Asn Asp Asn Ser Gln Pro Ser Gly Ile Pro Glu Arg Phe
 65                  70                  75                  80

Ser Gly Thr Asn Ser Gly Ser Thr Ala Thr Leu Thr Ile Ser Glu Ala
                 85                  90                  95

Gln Thr Asn Asp Glu Ala Asp Tyr Tyr Cys Gln His Tyr His His Asp
            100                 105                 110

Tyr Cys Trp Val Phe Gly Glu Gly Thr Gln Leu Thr Val Leu Gly Gln
        115                 120                 125

Pro Lys Ser Ser Pro Leu Val Thr Leu Phe Pro Pro Ser Ser Glu Glu
    130                 135                 140

Leu Gly Ala Asn Lys Ala Thr Leu Val Cys Leu Ile Ser Asp Phe Tyr
145                 150                 155                 160

Pro Ser Gly Leu Lys Val Ala Trp Lys Ala Asp Gly Ser Thr Ile Ile
                165                 170                 175

Gln Gly Val Glu Thr Thr Lys Pro Ser Lys Gln Ser Asn Asn Lys Tyr
            180                 185                 190

Thr Ala Ser Ser Tyr Leu Ser Leu Thr Pro Asp Lys Trp Lys Ser His
        195                 200                 205

Ser Ser Phe Ser Cys Leu Val Thr His Gln Gly Ser Thr Val Glu Lys
    210                 215                 220

Lys Val Ala Pro Ala Glu Cys Ser
225                 230

<210> SEQ ID NO 72
<211> LENGTH: 861
<212> TYPE: DNA
<213> ORGANISM: Canis familiaris
<220> FEATURE:
<221> NAME/KEY: CDS
<222> LOCATION: (1)..(696)

<400> SEQUENCE: 72 atg gcc tgg acc ctt ctt ctc ctt gga ttc ctg gct cac tgc aca ggt       48
Met Ala Trp Thr Leu Leu Leu Leu Gly Phe Leu Ala His Cys Thr Gly
 1               5                  10                  15 tcc gtg gcc tcc tat gtg ctg act cag tca ccc tca gtg tca gtg acc       96
Ser Val Ala Ser Tyr Val Leu Thr Gln Ser Pro Ser Val Ser Val Thr
             20                  25                  30 ctg gga cag acg gcc agc atc acc tgt agg gga aac agc att gga agg      144
Leu Gly Gln Thr Ala Ser Ile Thr Cys Arg Gly Asn Ser Ile Gly Arg
         35                  40                  45 aaa gat gtt cat tgg tac cag cag aag ccg ggc caa gcc ccc ctg ctg      192
Lys Asp Val His Trp Tyr Gln Gln Lys Pro Gly Gln Ala Pro Leu Leu
     50                  55                  60 att atc tat aat gat aac agc cag ccc tca ggg atc cct gag cga ttc      240
Ile Ile Tyr Asn Asp Asn Ser Gln Pro Ser Gly Ile Pro Glu Arg Phe
 65                  70                  75                  80 tct ggg acc aac tca ggg agc acg gcc acc ctg acc atc agt gag gcc      288
Ser Gly Thr Asn Ser Gly Ser Thr Ala Thr Leu Thr Ile Ser Glu Ala
                 85                  90                  95 caa acc aac gat gag gct gac tat tac tgc cag gtc cat ggg ggg gga      336
Gln Thr Asn Asp Glu Ala Asp Tyr Tyr Cys Gln Val His Gly Gly Gly
            100                 105                 110 ggg tgt tgg gta ttc ggt gaa ggg acc cag ctg acc gtc ctc ggt cag      384
Gly Cys Trp Val Phe Gly Glu Gly Thr Gln Leu Thr Val Leu Gly Gln
        115                 120                 125 ccc aag tcc tcc ccc ttg gtc aca ctc ttc ccg ccc tcc tct gag gag      432
```

```
Pro Lys Ser Ser Pro Leu Val Thr Leu Phe Pro Pro Ser Ser Glu Glu
    130                 135                 140 ctc ggc gcc aac aag gct acc ctg gtg tgc ctc atc agc gac ttc tac       480
Leu Gly Ala Asn Lys Ala Thr Leu Val Cys Leu Ile Ser Asp Phe Tyr
145                 150                 155                 160 ccc agt ggc ctg aaa gtg gct tgg aag gca gat ggc agc acc atc atc       528
Pro Ser Gly Leu Lys Val Ala Trp Lys Ala Asp Gly Ser Thr Ile Ile
                165                 170                 175 cag ggc gtg gaa acc acc aag ccc tcc aag cag agc aac aac aag tac       576
Gln Gly Val Glu Thr Thr Lys Pro Ser Lys Gln Ser Asn Asn Lys Tyr
            180                 185                 190 acg gcc agc agc tac ctg agc ctg acg cct gac aag tgg aaa tct cac       624
Thr Ala Ser Ser Tyr Leu Ser Leu Thr Pro Asp Lys Trp Lys Ser His
        195                 200                 205 agc agc ttc agc tgc ctg gtc acg cac cag ggg agc acc gtg gag aag       672
Ser Ser Phe Ser Cys Leu Val Thr His Gln Gly Ser Thr Val Glu Lys
    210                 215                 220 aag gtg gcc cct gca gag tgc tct taggtccctg agaattcctg agatggagcc      726
Lys Val Ala Pro Ala Glu Cys Ser
225                 230 ttcctcaccc agacacccct tccccagttc accttgtgcc cctgaaaacc caccctggac     786
cagctcagac caggcaggtc actcatcctc cctgtttcta cttgtgctca ataaagactt     846
tatcatttat cactg                                                     861
```

\<210\> SEQ ID NO 73
\<211\> LENGTH: 232
\<212\> TYPE: PRT
\<213\> ORGANISM: Canis familiaris

\<400\> SEQUENCE: 73

```
Met Ala Trp Thr Leu Leu Leu Gly Phe Leu Ala His Cys Thr Gly
1               5                   10                  15

Ser Val Ala Ser Tyr Val Leu Thr Gln Ser Pro Ser Val Ser Val Thr
            20                  25                  30

Leu Gly Gln Thr Ala Ser Ile Thr Cys Arg Gly Asn Ser Ile Gly Arg
        35                  40                  45

Lys Asp Val His Trp Tyr Gln Gln Lys Pro Gly Gln Ala Pro Leu Leu
    50                  55                  60

Ile Ile Tyr Asn Asp Asn Ser Gln Pro Ser Gly Ile Pro Glu Arg Phe
65                  70                  75                  80

Ser Gly Thr Asn Ser Gly Ser Thr Ala Thr Leu Thr Ile Ser Glu Ala
                85                  90                  95

Gln Thr Asn Asp Glu Ala Asp Tyr Tyr Cys Gln Val His Gly Gly Gly
            100                 105                 110

Gly Cys Trp Val Phe Gly Glu Gly Thr Gln Leu Thr Val Leu Gly Gln
        115                 120                 125

Pro Lys Ser Ser Pro Leu Val Thr Leu Phe Pro Pro Ser Ser Glu Glu
    130                 135                 140

Leu Gly Ala Asn Lys Ala Thr Leu Val Cys Leu Ile Ser Asp Phe Tyr
145                 150                 155                 160

Pro Ser Gly Leu Lys Val Ala Trp Lys Ala Asp Gly Ser Thr Ile Ile
                165                 170                 175

Gln Gly Val Glu Thr Thr Lys Pro Ser Lys Gln Ser Asn Asn Lys Tyr
            180                 185                 190

Thr Ala Ser Ser Tyr Leu Ser Leu Thr Pro Asp Lys Trp Lys Ser His
        195                 200                 205
```

```
Ser Ser Phe Ser Cys Leu Val Thr His Gln Gly Ser Thr Val Glu Lys
    210                 215                 220

Lys Val Ala Pro Ala Glu Cys Ser
225                 230

<210> SEQ ID NO 74
<211> LENGTH: 861
<212> TYPE: DNA
<213> ORGANISM: Canis familiaris
<220> FEATURE:
<221> NAME/KEY: CDS
<222> LOCATION: (1)..(696)

<400> SEQUENCE: 74 atg gcc tgg acc ctt ctt ctc ctt gga ttc ctg gct cac tgc aca ggt     48
Met Ala Trp Thr Leu Leu Leu Leu Gly Phe Leu Ala His Cys Thr Gly
1               5                   10                  15 tcc gtg gcc tcc tat gtg ctg act cag tca ccc tca gtg tca gtg acc     96
Ser Val Ala Ser Tyr Val Leu Thr Gln Ser Pro Ser Val Ser Val Thr
                20                  25                  30 ctg gga cag acg gcc agc atc acc tgt agg gga aac agc att gga agg    144
Leu Gly Gln Thr Ala Ser Ile Thr Cys Arg Gly Asn Ser Ile Gly Arg
            35                  40                  45 aaa gat gtt cat tgg tac cag cag aag ccg ggc caa gcc ccc ctg ctg    192
Lys Asp Val His Trp Tyr Gln Gln Lys Pro Gly Gln Ala Pro Leu Leu
        50                  55                  60 att atc tat aat gat aac agc cag ccc tca ggg atc cct gag cga ttc    240
Ile Ile Tyr Asn Asp Asn Ser Gln Pro Ser Gly Ile Pro Glu Arg Phe
65                  70                  75                  80 tct ggg acc aac tca ggg agc acg gcc acc ctg acc atc agt gag gcc    288
Ser Gly Thr Asn Ser Gly Ser Thr Ala Thr Leu Thr Ile Ser Glu Ala
                85                  90                  95 caa acc aac gat gag gct gac tat tac tgc cag aaa cat cgg ggt gca    336
Gln Thr Asn Asp Glu Ala Asp Tyr Tyr Cys Gln Lys His Arg Gly Ala
            100                 105                 110 ggt tgt tgg gta ttc ggt gaa ggg acc cag ctg acc gtc ctc ggt cag    384
Gly Cys Trp Val Phe Gly Glu Gly Thr Gln Leu Thr Val Leu Gly Gln
        115                 120                 125 ccc aag tcc tcc ccc ttg gtc aca ctc ttc ccg ccc tcc tct gag gag    432
Pro Lys Ser Ser Pro Leu Val Thr Leu Phe Pro Pro Ser Ser Glu Glu
    130                 135                 140 ctc ggc gcc aac aag gct acc ctg gtg tgc ctc atc agc gac ttc tac    480
Leu Gly Ala Asn Lys Ala Thr Leu Val Cys Leu Ile Ser Asp Phe Tyr
145                 150                 155                 160 ccc agt ggc ctg aaa gtg gct tgg aag gca gat ggc agc acc atc atc    528
Pro Ser Gly Leu Lys Val Ala Trp Lys Ala Asp Gly Ser Thr Ile Ile
                165                 170                 175 cag ggc gtg gaa acc acc aag ccc tcc aag cag agc aac aac aag tac    576
Gln Gly Val Glu Thr Thr Lys Pro Ser Lys Gln Ser Asn Asn Lys Tyr
            180                 185                 190 acg gcc agc agc tac ctg agc ctg acg cct gac aag tgg aaa tct cac    624
Thr Ala Ser Ser Tyr Leu Ser Leu Thr Pro Asp Lys Trp Lys Ser His
        195                 200                 205 agc agc ttc agc tgc ctg gtc acg cac cag ggg agc acc gtg gag aag    672
Ser Ser Phe Ser Cys Leu Val Thr His Gln Gly Ser Thr Val Glu Lys
    210                 215                 220 aag gtg gcc cct gca gag tgc tct taggtccctg agaattcctg agatggagcc    726
Lys Val Ala Pro Ala Glu Cys Ser
225                 230 ttcctcaccc agacacccct tcccagttc accttgtgcc cctgaaaacc caccctggac    786
```
cagctcagac caggcaggtc actcatcctc cctgtttcta cttgtgctca ataaagactt    846
tatcatttat cactg                                                    861

<210> SEQ ID NO 75
<211> LENGTH: 232
<212> TYPE: PRT
<213> ORGANISM: Canis familiaris

<400> SEQUENCE: 75

Met Ala Trp Thr Leu Leu Leu Leu Gly Phe Leu Ala His Cys Thr Gly
1               5                   10                  15

Ser Val Ala Ser Tyr Val Leu Thr Gln Ser Pro Ser Val Ser Val Thr
            20                  25                  30

Leu Gly Gln Thr Ala Ser Ile Thr Cys Arg Gly Asn Ser Ile Gly Arg
        35                  40                  45

Lys Asp Val His Trp Tyr Gln Gln Lys Pro Gly Gln Ala Pro Leu Leu
    50                  55                  60

Ile Ile Tyr Asn Asp Asn Ser Gln Pro Ser Gly Ile Pro Glu Arg Phe
65                  70                  75                  80

Ser Gly Thr Asn Ser Gly Ser Thr Ala Thr Leu Thr Ile Ser Glu Ala
                85                  90                  95

Gln Thr Asn Asp Glu Ala Asp Tyr Tyr Cys Gln Lys His Arg Gly Ala
            100                 105                 110

Gly Cys Trp Val Phe Gly Glu Gly Thr Gln Leu Thr Val Leu Gly Gln
        115                 120                 125

Pro Lys Ser Ser Pro Leu Val Thr Leu Phe Pro Ser Ser Glu Glu
    130                 135                 140

Leu Gly Ala Asn Lys Ala Thr Leu Val Cys Leu Ile Ser Asp Phe Tyr
145                 150                 155                 160

Pro Ser Gly Leu Lys Val Ala Trp Lys Ala Asp Gly Ser Thr Ile Ile
                165                 170                 175

Gln Gly Val Glu Thr Thr Lys Pro Ser Lys Gln Ser Asn Asn Lys Tyr
            180                 185                 190

Thr Ala Ser Ser Tyr Leu Ser Leu Thr Pro Asp Lys Trp Lys Ser His
        195                 200                 205

Ser Ser Phe Ser Cys Leu Val Thr His Gln Gly Ser Thr Val Glu Lys
    210                 215                 220

Lys Val Ala Pro Ala Glu Cys Ser
225                 230

<210> SEQ ID NO 76
<211> LENGTH: 858
<212> TYPE: DNA
<213> ORGANISM: Canis familiaris
<220> FEATURE:
<221> NAME/KEY: CDS
<222> LOCATION: (1)..(693)

<400> SEQUENCE: 76 atg gcc tgg acc ctt ctt ctc ctt gga ttc ctg gct cac tgc aca ggt    48
Met Ala Trp Thr Leu Leu Leu Leu Gly Phe Leu Ala His Cys Thr Gly
1               5                   10                  15 tcc gtg gcc tcc tat gtg ctg act cag tca ccc tca gtg tca gtg acc    96
Ser Val Ala Ser Tyr Val Leu Thr Gln Ser Pro Ser Val Ser Val Thr
            20                  25                  30 ctg gga cag acg gcc agc atc acc tgt agg gga aac agc att gga agg    144
Leu Gly Gln Thr Ala Ser Ile Thr Cys Arg Gly Asn Ser Ile Gly Arg
        35                  40                  45

```
              35                  40                  45
aaa gat gtt cat tgg tac cag cag aag ccg ggc caa gcc ccc ctg ctg        192
Lys Asp Val His Trp Tyr Gln Gln Lys Pro Gly Gln Ala Pro Leu Leu
         50                  55                  60 att atc tat aat gat aac agc cag ccc tca ggg atc cct gag cga ttc        240
Ile Ile Tyr Asn Asp Asn Ser Gln Pro Ser Gly Ile Pro Glu Arg Phe
 65                  70                  75                  80 tct ggg acc aac tca ggg agc acg gcc acc ctg acc atc agt gag gcc        288
Ser Gly Thr Asn Ser Gly Ser Thr Ala Thr Leu Thr Ile Ser Glu Ala
                 85                  90                  95 caa acc aac gat gag gct gac tat tac tgc cag gtg tcc ctt ggg tct        336
Gln Thr Asn Asp Glu Ala Asp Tyr Tyr Cys Gln Val Ser Leu Gly Ser
            100                 105                 110 tgt tgg gta ttc ggt gaa ggg acc cag ctg acc gtc ctc ggt cag ccc        384
Cys Trp Val Phe Gly Glu Gly Thr Gln Leu Thr Val Leu Gly Gln Pro
        115                 120                 125 aag tcc tcc ccc ttg gtc aca ctc ttc ccg ccc tcc tct gag gag ctc        432
Lys Ser Ser Pro Leu Val Thr Leu Phe Pro Pro Ser Ser Glu Glu Leu
    130                 135                 140 ggc gcc aac aag gct acc ctg gtg tgc ctc atc agc gac ttc tac ccc        480
Gly Ala Asn Lys Ala Thr Leu Val Cys Leu Ile Ser Asp Phe Tyr Pro
145                 150                 155                 160 agt ggc ctg aaa gtg gct tgg aag gca gat ggc agc acc atc atc cag        528
Ser Gly Leu Lys Val Ala Trp Lys Ala Asp Gly Ser Thr Ile Ile Gln
                165                 170                 175 ggc gtg gaa acc acc aag ccc tcc aag cag agc aac aac aag tac acg        576
Gly Val Glu Thr Thr Lys Pro Ser Lys Gln Ser Asn Asn Lys Tyr Thr
            180                 185                 190 gcc agc agc tac ctg agc ctg acg cct gac aag tgg aaa tct cac agc        624
Ala Ser Ser Tyr Leu Ser Leu Thr Pro Asp Lys Trp Lys Ser His Ser
        195                 200                 205 agc ttc agc tgc ctg gtc acg cac cag ggg agc acc gtg gag aag aag        672
Ser Phe Ser Cys Leu Val Thr His Gln Gly Ser Thr Val Glu Lys Lys
    210                 215                 220 gtg gcc cct gca gag tgc tct taggtccctg agaattcctg agatggagcc          723
Val Ala Pro Ala Glu Cys Ser
225                 230 ttcctcaccc agacacccct tcccagttc accttgtgcc cctgaaaacc cacctggac       783 cagctcagac caggcaggtc actcatcctc cctgtttcta cttgtgctca ataaagactt     843
tatcatttat cactg                                                      858

<210> SEQ ID NO 77
<211> LENGTH: 231
<212> TYPE: PRT
<213> ORGANISM: Canis familiaris

<400> SEQUENCE: 77

Met Ala Trp Thr Leu Leu Leu Gly Phe Leu Ala His Cys Thr Gly
 1               5                  10                  15

Ser Val Ala Ser Tyr Val Leu Thr Gln Ser Pro Ser Val Ser Val Thr
                20                  25                  30

Leu Gly Gln Thr Ala Ser Ile Thr Cys Arg Gly Asn Ser Ile Gly Arg
            35                  40                  45

Lys Asp Val His Trp Tyr Gln Gln Lys Pro Gly Gln Ala Pro Leu Leu
        50                  55                  60

Ile Ile Tyr Asn Asp Asn Ser Gln Pro Ser Gly Ile Pro Glu Arg Phe
 65                  70                  75                  80
```

```
Ser Gly Thr Asn Ser Gly Ser Thr Ala Thr Leu Thr Ile Ser Glu Ala
            85                  90                  95

Gln Thr Asn Asp Glu Ala Asp Tyr Tyr Cys Gln Val Ser Leu Gly Ser
            100                 105                 110

Cys Trp Val Phe Gly Glu Gly Thr Gln Leu Thr Val Leu Gly Gln Pro
            115                 120                 125

Lys Ser Ser Pro Leu Val Thr Leu Phe Pro Pro Ser Ser Glu Glu Leu
            130                 135                 140

Gly Ala Asn Lys Ala Thr Leu Val Cys Leu Ile Ser Asp Phe Tyr Pro
145                 150                 155                 160

Ser Gly Leu Lys Val Ala Trp Lys Ala Asp Gly Ser Thr Ile Ile Gln
                165                 170                 175

Gly Val Glu Thr Thr Lys Pro Ser Lys Gln Ser Asn Asn Lys Tyr Thr
            180                 185                 190

Ala Ser Ser Tyr Leu Ser Leu Thr Pro Asp Lys Trp Lys Ser His Ser
            195                 200                 205

Ser Phe Ser Cys Leu Val Thr His Gln Gly Ser Thr Val Glu Lys Lys
            210                 215                 220

Val Ala Pro Ala Glu Cys Ser
225                 230

<210> SEQ ID NO 78
<211> LENGTH: 858
<212> TYPE: DNA
<213> ORGANISM: Canis familiaris
<220> FEATURE:
<221> NAME/KEY: CDS
<222> LOCATION: (1)..(693)

<400> SEQUENCE: 78 atg gcc tgg acc ctt ctt ctc ctt gga ttc ctg gct cac tgc aca ggt      48
Met Ala Trp Thr Leu Leu Leu Leu Gly Phe Leu Ala His Cys Thr Gly
1               5                   10                  15 tcc gtg gcc tcc tat gtg ctg act cag tca ccc tca gtg tca gtg acc      96
Ser Val Ala Ser Tyr Val Leu Thr Gln Ser Pro Ser Val Ser Val Thr
            20                  25                  30 ctg gga cag acg gcc agc atc acc tgt agg gga aac agc att gga agg     144
Leu Gly Gln Thr Ala Ser Ile Thr Cys Arg Gly Asn Ser Ile Gly Arg
        35                  40                  45 aaa gat gtt cat tgg tac cag cag aag ccg ggc caa gcc ccc ctg ctg     192
Lys Asp Val His Trp Tyr Gln Gln Lys Pro Gly Gln Ala Pro Leu Leu
50                  55                  60 att atc tat aat gat aac agc cag ccc tca ggg atc cct gag cga ttc     240
Ile Ile Tyr Asn Asp Asn Ser Gln Pro Ser Gly Ile Pro Glu Arg Phe
65                  70                  75                  80 tct ggg acc aac tca ggg agc acg gcc acc ctg acc atc agt gag gcc     288
Ser Gly Thr Asn Ser Gly Ser Thr Ala Thr Leu Thr Ile Ser Glu Ala
            85                  90                  95 caa acc aac gat gag gct gac tat tac tgc cag gta ttg atg gga ggg     336
Gln Thr Asn Asp Glu Ala Asp Tyr Tyr Cys Gln Val Leu Met Gly Gly
            100                 105                 110 tgt tgg gta ttc ggt gaa ggg acc cag ctg acc gtc ctc ggt cag ccc     384
Cys Trp Val Phe Gly Glu Gly Thr Gln Leu Thr Val Leu Gly Gln Pro
            115                 120                 125 aag tcc tcc ccc ttg gtc aca ctc ttc ccg ccc tcc tct gag gag ctc     432
Lys Ser Ser Pro Leu Val Thr Leu Phe Pro Pro Ser Ser Glu Glu Leu
            130                 135                 140 ggc gcc aac aag gct acc ctg gtg tgc ctc atc agc gac ttc tac ccc     480
Gly Ala Asn Lys Ala Thr Leu Val Cys Leu Ile Ser Asp Phe Tyr Pro
```

| | | | | | | | | | | | | | | | | |
|---|---|---|---|---|---|---|---|---|---|---|---|---|---|---|---|---|
| | | 145 | | | 150 | | | | 155 | | | | 160 | | | |
| agt | ggc | ctg | aaa | gtg | gct | tgg | aag | gca | gat | ggc | agc | acc | atc | atc | cag | 528 |
| Ser | Gly | Leu | Lys | Val | Ala | Trp | Lys | Ala | Asp | Gly | Ser | Thr | Ile | Ile | Gln | |
| | | 165 | | | | | 170 | | | | | 175 | | | | |
| ggc | gtg | gaa | acc | acc | aag | ccc | tcc | aag | cag | agc | aac | aac | aag | tac | acg | 576 |
| Gly | Val | Glu | Thr | Thr | Lys | Pro | Ser | Lys | Gln | Ser | Asn | Asn | Lys | Tyr | Thr | |
| | | 180 | | | | | 185 | | | | | 190 | | | | |
| gcc | agc | agc | tac | ctg | agc | ctg | acg | cct | gac | aag | tgg | aaa | tct | cac | agc | 624 |
| Ala | Ser | Ser | Tyr | Leu | Ser | Leu | Thr | Pro | Asp | Lys | Trp | Lys | Ser | His | Ser | |
| | 195 | | | | | 200 | | | | | 205 | | | | | |
| agc | ttc | agc | tgc | ctg | gtc | acg | cac | cag | ggg | agc | acc | gtg | gag | aag | aag | 672 |
| Ser | Phe | Ser | Cys | Leu | Val | Thr | His | Gln | Gly | Ser | Thr | Val | Glu | Lys | Lys | |
| | 210 | | | | | 215 | | | | | 220 | | | | | |
| gtg | gcc | cct | gca | gag | tgc | tct | tag | gtccctg | agaattcctg | agatggagcc | | | | | | 723 |
| Val | Ala | Pro | Ala | Glu | Cys | Ser | | | | | | | | | | |
| 225 | | | | 230 | | | | | | | | | | | | |

| | | |
|---|---|---|
| ttcctcaccc agacacccct tccccagttc accttgtgcc cctgaaaacc caccctggac | | 783 |
| cagctcagac caggcaggtc actcatcctc cctgtttcta cttgtgctca ataaagactt | | 843 |
| tatcatttat cactg | | 858 |

<210> SEQ ID NO 79
<211> LENGTH: 231
<212> TYPE: PRT
<213> ORGANISM: Canis familiaris

<400> SEQUENCE: 79

| Met | Ala | Trp | Thr | Leu | Leu | Leu | Gly | Phe | Leu | Ala | His | Cys | Thr | Gly |
|---|---|---|---|---|---|---|---|---|---|---|---|---|---|---|
| 1 | | | | 5 | | | | | 10 | | | | | 15 |

| Ser | Val | Ala | Ser | Tyr | Val | Leu | Thr | Gln | Ser | Pro | Ser | Val | Ser | Val | Thr |
|---|---|---|---|---|---|---|---|---|---|---|---|---|---|---|---|
| | | | 20 | | | | | 25 | | | | | 30 | | |

| Leu | Gly | Gln | Thr | Ala | Ser | Ile | Thr | Cys | Arg | Gly | Asn | Ser | Ile | Gly | Arg |
|---|---|---|---|---|---|---|---|---|---|---|---|---|---|---|---|
| | | | 35 | | | | | 40 | | | | | 45 | | |

| Lys | Asp | Val | His | Trp | Tyr | Gln | Gln | Lys | Pro | Gly | Gln | Ala | Pro | Leu | Leu |
|---|---|---|---|---|---|---|---|---|---|---|---|---|---|---|---|
| | 50 | | | | | 55 | | | | | 60 | | | | |

| Ile | Ile | Tyr | Asn | Asp | Asn | Ser | Gln | Pro | Ser | Gly | Ile | Pro | Glu | Arg | Phe |
|---|---|---|---|---|---|---|---|---|---|---|---|---|---|---|---|
| 65 | | | | | 70 | | | | | 75 | | | | | 80 |

| Ser | Gly | Thr | Asn | Ser | Gly | Ser | Thr | Ala | Thr | Leu | Thr | Ile | Ser | Glu | Ala |
|---|---|---|---|---|---|---|---|---|---|---|---|---|---|---|---|
| | | | | 85 | | | | | 90 | | | | | 95 | |

| Gln | Thr | Asn | Asp | Glu | Ala | Asp | Tyr | Tyr | Cys | Gln | Val | Leu | Met | Gly | Gly |
|---|---|---|---|---|---|---|---|---|---|---|---|---|---|---|---|
| | | | 100 | | | | | 105 | | | | | 110 | | |

| Cys | Trp | Val | Phe | Gly | Glu | Gly | Thr | Gln | Leu | Thr | Val | Leu | Gly | Gln | Pro |
|---|---|---|---|---|---|---|---|---|---|---|---|---|---|---|---|
| | | | 115 | | | | | 120 | | | | | 125 | | |

| Lys | Ser | Ser | Pro | Leu | Val | Thr | Leu | Phe | Pro | Pro | Ser | Ser | Glu | Glu | Leu |
|---|---|---|---|---|---|---|---|---|---|---|---|---|---|---|---|
| | 130 | | | | | 135 | | | | | 140 | | | | |

| Gly | Ala | Asn | Lys | Ala | Thr | Leu | Val | Cys | Leu | Ile | Ser | Asp | Phe | Tyr | Pro |
|---|---|---|---|---|---|---|---|---|---|---|---|---|---|---|---|
| 145 | | | | | 150 | | | | | 155 | | | | | 160 |

| Ser | Gly | Leu | Lys | Val | Ala | Trp | Lys | Ala | Asp | Gly | Ser | Thr | Ile | Ile | Gln |
|---|---|---|---|---|---|---|---|---|---|---|---|---|---|---|---|
| | | | | 165 | | | | | 170 | | | | | 175 | |

| Gly | Val | Glu | Thr | Thr | Lys | Pro | Ser | Lys | Gln | Ser | Asn | Asn | Lys | Tyr | Thr |
|---|---|---|---|---|---|---|---|---|---|---|---|---|---|---|---|
| | | | 180 | | | | | 185 | | | | | 190 | | |

| Ala | Ser | Ser | Tyr | Leu | Ser | Leu | Thr | Pro | Asp | Lys | Trp | Lys | Ser | His | Ser |
|---|---|---|---|---|---|---|---|---|---|---|---|---|---|---|---|
| | | 195 | | | | | 200 | | | | | 205 | | | |

| Ser | Phe | Ser | Cys | Leu | Val | Thr | His | Gln | Gly | Ser | Thr | Val | Glu | Lys | Lys |
|---|---|---|---|---|---|---|---|---|---|---|---|---|---|---|---|
| | 210 | | | | | 215 | | | | | 220 | | | | |

| Val | Ala | Pro | Ala | Glu | Cys | Ser |
|---|---|---|---|---|---|---|

```
<210> SEQ ID NO 80
<211> LENGTH: 834
<212> TYPE: DNA
<213> ORGANISM: Canis familiaris
<220> FEATURE:
<221> NAME/KEY: CDS
<222> LOCATION: (1)..(669)

<400> SEQUENCE: 80 atg tcc tct ctt gca ggt tcc atg gct gcc aac aag ctg act caa tcc      48
Met Ser Ser Leu Ala Gly Ser Met Ala Ala Asn Lys Leu Thr Gln Ser
1               5                   10                  15 ctg ttt atg tca gtg gcc ctg gga cag atg gcc agg atc acc tgt ggg      96
Leu Phe Met Ser Val Ala Leu Gly Gln Met Ala Arg Ile Thr Cys Gly
            20                  25                  30 aga gac aac tct gga aga aaa agt gct cac tgg tac cag cag aag cca     144
Arg Asp Asn Ser Gly Arg Lys Ser Ala His Trp Tyr Gln Gln Lys Pro
        35                  40                  45 agc cag gct ccc gtg atg ctt atc gat gat gat tgc ttc cag ccc tca     192
Ser Gln Ala Pro Val Met Leu Ile Asp Asp Asp Cys Phe Gln Pro Ser
    50                  55                  60 gga ttc tct gag caa ttc tca ggc act aac tcg ggg aac aca gcc acc     240
Gly Phe Ser Glu Gln Phe Ser Gly Thr Asn Ser Gly Asn Thr Ala Thr
65                  70                  75                  80 ctg acc att agt ggg ccc cca gcg agg acg cag gtc agg tat gcc cag     288
Leu Thr Ile Ser Gly Pro Pro Ala Arg Thr Gln Val Arg Tyr Ala Gln
                85                  90                  95 ccc ggg gct cca ggg gca ggg act tgt tgg gta ttc ggt gaa ggg acc     336
Pro Gly Ala Pro Gly Ala Gly Thr Cys Trp Val Phe Gly Glu Gly Thr
            100                 105                 110 cag ctg acc gtc ctc ggt cag ccc aag tcc tcc ccc ttg gtc aca ctc     384
Gln Leu Thr Val Leu Gly Gln Pro Lys Ser Ser Pro Leu Val Thr Leu
        115                 120                 125 ttc ccg ccc tcc tct gag gag ctc ggc gcc aac aag gct acc ctg gtg     432
Phe Pro Pro Ser Ser Glu Glu Leu Gly Ala Asn Lys Ala Thr Leu Val
    130                 135                 140 tgc ctc atc agc gac ttc tac ccc agt ggc ctg aaa gtg gct tgg aag     480
Cys Leu Ile Ser Asp Phe Tyr Pro Ser Gly Leu Lys Val Ala Trp Lys
145                 150                 155                 160 gca gat ggc agc acc atc atc cag ggc gtg gaa acc acc aag ccc tcc     528
Ala Asp Gly Ser Thr Ile Ile Gln Gly Val Glu Thr Thr Lys Pro Ser
                165                 170                 175 aag cag agc aac aac aag tac acg gcc agc agc tac ctg agc ctg acg     576
Lys Gln Ser Asn Asn Lys Tyr Thr Ala Ser Ser Tyr Leu Ser Leu Thr
            180                 185                 190 cct gac aag tgg aaa tct cac agc agc ttc agc tgc ctg gtc acg cac     624
Pro Asp Lys Trp Lys Ser His Ser Ser Phe Ser Cys Leu Val Thr His
        195                 200                 205 cag ggg agc acc gtg gag aag aag gtg gcc cct gca gag tgc tct         669
Gln Gly Ser Thr Val Glu Lys Lys Val Ala Pro Ala Glu Cys Ser
    210                 215                 220 taggtccctg agaattcctg agatggagcc ttcctcaccc agacacccct tccccagttc   729
accttgtgcc cctgaaaacc cacccctggac cagctcagac caggcaggtc actcatcctc  789
cctgtttcta cttgtgctca ataaagactt tatcatttat cactg                   834

<210> SEQ ID NO 81
<211> LENGTH: 223
<212> TYPE: PRT
```

<213> ORGANISM: Canis familiaris

<400> SEQUENCE: 81

```
Met Ser Ser Leu Ala Gly Ser Met Ala Ala Asn Lys Leu Thr Gln Ser
1               5                   10                  15

Leu Phe Met Ser Val Ala Leu Gly Gln Met Ala Arg Ile Thr Cys Gly
            20                  25                  30

Arg Asp Asn Ser Gly Arg Lys Ser Ala His Trp Tyr Gln Gln Lys Pro
        35                  40                  45

Ser Gln Ala Pro Val Met Leu Ile Asp Asp Cys Phe Gln Pro Ser
    50                  55                  60

Gly Phe Ser Glu Gln Phe Ser Gly Thr Asn Ser Gly Asn Thr Ala Thr
65                  70                  75                  80

Leu Thr Ile Ser Gly Pro Pro Ala Arg Thr Gln Val Arg Tyr Ala Gln
                85                  90                  95

Pro Gly Ala Pro Gly Ala Gly Thr Cys Trp Val Phe Gly Glu Gly Thr
            100                 105                 110

Gln Leu Thr Val Leu Gly Gln Pro Lys Ser Ser Pro Leu Val Thr Leu
        115                 120                 125

Phe Pro Pro Ser Ser Glu Glu Leu Gly Ala Asn Lys Ala Thr Leu Val
    130                 135                 140

Cys Leu Ile Ser Asp Phe Tyr Pro Ser Gly Leu Lys Val Ala Trp Lys
145                 150                 155                 160

Ala Asp Gly Ser Thr Ile Ile Gln Gly Val Glu Thr Thr Lys Pro Ser
                165                 170                 175

Lys Gln Ser Asn Asn Lys Tyr Thr Ala Ser Ser Tyr Leu Ser Leu Thr
            180                 185                 190

Pro Asp Lys Trp Lys Ser His Ser Ser Phe Ser Cys Leu Val Thr His
        195                 200                 205

Gln Gly Ser Thr Val Glu Lys Lys Val Ala Pro Ala Glu Cys Ser
    210                 215                 220
```

<210> SEQ ID NO 82
<211> LENGTH: 780
<212> TYPE: DNA
<213> ORGANISM: Canis familiaris
<220> FEATURE:
<221> NAME/KEY: CDS
<222> LOCATION: (1)..(615)

<400> SEQUENCE: 82

```
atg tca gtg gcc ctg gga cag atg gcc agg atc acc tgt ggg aga gac     48
Met Ser Val Ala Leu Gly Gln Met Ala Arg Ile Thr Cys Gly Arg Asp
1               5                   10                  15 aac tct gga aga aaa agt gct cac tgg tac cag cag aag cca agc cag     96
Asn Ser Gly Arg Lys Ser Ala His Trp Tyr Gln Gln Lys Pro Ser Gln
            20                  25                  30 gct ccc gtg atg ctt atc gat gat gat tgc ttc cag ccc tca gga ttc    144
Ala Pro Val Met Leu Ile Asp Asp Asp Cys Phe Gln Pro Ser Gly Phe
        35                  40                  45 tct gag caa ttc tca ggc act aac tcg ggg aac aca gcc acc ctg acc    192
Ser Glu Gln Phe Ser Gly Thr Asn Ser Gly Asn Thr Ala Thr Leu Thr
    50                  55                  60 att aaa gaa atg gac gca ttc ctg gaa acc tcc ttc tat tgc tgg atg    240
Ile Lys Glu Met Asp Ala Phe Leu Glu Thr Ser Phe Tyr Cys Trp Met
65                  70                  75                  80 tgg cag cct gaa tca cag tgt tgg gta ttc ggt gaa ggg acc cag ctg    288
Trp Gln Pro Glu Ser Gln Cys Trp Val Phe Gly Glu Gly Thr Gln Leu
```

|  |  |  |  |  |  |  |  |  |  |  |  |  |  |  |  |
|---|---|---|---|---|---|---|---|---|---|---|---|---|---|---|---|
|  |  |  | 85 |  |  |  |  | 90 |  |  |  |  | 95 |  |  |
| acc | gtc | ctc | ggt | cag | ccc | aag | tcc | tcc | ccc | ttg | gtc | aca | ctc | ttc | ccg | 336 |
| Thr | Val | Leu | Gly | Gln | Pro | Lys | Ser | Ser | Pro | Leu | Val | Thr | Leu | Phe | Pro |
|  |  |  | 100 |  |  |  |  | 105 |  |  |  |  | 110 |  |  |
| ccc | tcc | tct | gag | gag | ctc | ggc | gcc | aac | aag | gct | acc | ctg | gtg | tgc | ctc | 384 |
| Pro | Ser | Ser | Glu | Glu | Leu | Gly | Ala | Asn | Lys | Ala | Thr | Leu | Val | Cys | Leu |
|  |  |  | 115 |  |  |  |  | 120 |  |  |  |  | 125 |  |  |
| atc | agc | gac | ttc | tac | ccc | agt | ggc | ctg | aaa | gtg | gct | tgg | aag | gca | gat | 432 |
| Ile | Ser | Asp | Phe | Tyr | Pro | Ser | Gly | Leu | Lys | Val | Ala | Trp | Lys | Ala | Asp |
|  |  |  | 130 |  |  |  |  | 135 |  |  |  |  | 140 |  |  |
| ggc | agc | acc | atc | atc | cag | ggc | gtg | gaa | acc | acc | aag | ccc | tcc | aag | cag | 480 |
| Gly | Ser | Thr | Ile | Ile | Gln | Gly | Val | Glu | Thr | Thr | Lys | Pro | Ser | Lys | Gln |
| 145 |  |  |  |  | 150 |  |  |  |  | 155 |  |  |  |  | 160 |
| agc | aac | aac | aag | tac | acg | gcc | agc | agc | tac | ctg | agc | ctg | acg | cct | gac | 528 |
| Ser | Asn | Asn | Lys | Tyr | Thr | Ala | Ser | Ser | Tyr | Leu | Ser | Leu | Thr | Pro | Asp |
|  |  |  |  | 165 |  |  |  |  | 170 |  |  |  |  | 175 |  |
| aag | tgg | aaa | tct | cac | agc | agc | ttc | agc | tgc | ctg | gtc | acg | cac | cag | ggg | 576 |
| Lys | Trp | Lys | Ser | His | Ser | Ser | Phe | Ser | Cys | Leu | Val | Thr | His | Gln | Gly |
|  |  |  |  | 180 |  |  |  |  | 185 |  |  |  |  | 190 |  |
| agc | acc | gtg | gag | aag | aag | gtg | gcc | cct | gca | gag | tgc | tct | taggtccctg |  |  | 625 |
| Ser | Thr | Val | Glu | Lys | Lys | Val | Ala | Pro | Ala | Glu | Cys | Ser |  |  |  |
|  |  |  | 195 |  |  |  |  | 200 |  |  |  |  | 205 |  |  | agaattcctg agatggagcc ttcctcaccc agacacccct tccccagttc accttgtgcc     685 cctgaaaacc caccctggac cagctcagac caggcaggtc actcatcctc cctgtttcta     745 cttgtgctca ataaagactt tatcatttat cactg     780

<210> SEQ ID NO 83
<211> LENGTH: 205
<212> TYPE: PRT
<213> ORGANISM: Canis familiaris

<400> SEQUENCE: 83

| Met | Ser | Val | Ala | Leu | Gly | Gln | Met | Ala | Arg | Ile | Thr | Cys | Gly | Arg | Asp |
|---|---|---|---|---|---|---|---|---|---|---|---|---|---|---|---|
| 1 |  |  |  | 5 |  |  |  |  | 10 |  |  |  |  | 15 |  |

| Asn | Ser | Gly | Arg | Lys | Ser | Ala | His | Trp | Tyr | Gln | Gln | Lys | Pro | Ser | Gln |
|---|---|---|---|---|---|---|---|---|---|---|---|---|---|---|---|
|  |  |  | 20 |  |  |  |  | 25 |  |  |  |  | 30 |  |  |

| Ala | Pro | Val | Met | Leu | Ile | Asp | Asp | Cys | Phe | Gln | Pro | Ser | Gly | Phe |
|---|---|---|---|---|---|---|---|---|---|---|---|---|---|---|
|  |  | 35 |  |  |  |  | 40 |  |  |  |  | 45 |  |  |

| Ser | Glu | Gln | Phe | Ser | Gly | Thr | Asn | Ser | Gly | Asn | Thr | Ala | Thr | Leu | Thr |
|---|---|---|---|---|---|---|---|---|---|---|---|---|---|---|---|
|  | 50 |  |  |  |  | 55 |  |  |  |  | 60 |  |  |  |  |

| Ile | Lys | Glu | Met | Asp | Ala | Phe | Leu | Glu | Thr | Ser | Phe | Tyr | Cys | Trp | Met |
|---|---|---|---|---|---|---|---|---|---|---|---|---|---|---|---|
| 65 |  |  |  |  | 70 |  |  |  |  | 75 |  |  |  |  | 80 |

| Trp | Gln | Pro | Glu | Ser | Gln | Cys | Trp | Val | Phe | Gly | Glu | Gly | Thr | Gln | Leu |
|---|---|---|---|---|---|---|---|---|---|---|---|---|---|---|---|
|  |  |  |  | 85 |  |  |  |  | 90 |  |  |  |  | 95 |  |

| Thr | Val | Leu | Gly | Gln | Pro | Lys | Ser | Ser | Pro | Leu | Val | Thr | Leu | Phe | Pro |
|---|---|---|---|---|---|---|---|---|---|---|---|---|---|---|---|
|  |  |  | 100 |  |  |  |  | 105 |  |  |  |  | 110 |  |  |

| Pro | Ser | Ser | Glu | Glu | Leu | Gly | Ala | Asn | Lys | Ala | Thr | Leu | Val | Cys | Leu |
|---|---|---|---|---|---|---|---|---|---|---|---|---|---|---|---|
|  |  | 115 |  |  |  |  | 120 |  |  |  |  | 125 |  |  |  |

| Ile | Ser | Asp | Phe | Tyr | Pro | Ser | Gly | Leu | Lys | Val | Ala | Trp | Lys | Ala | Asp |
|---|---|---|---|---|---|---|---|---|---|---|---|---|---|---|---|
|  | 130 |  |  |  |  | 135 |  |  |  |  | 140 |  |  |  |  |

| Gly | Ser | Thr | Ile | Ile | Gln | Gly | Val | Glu | Thr | Thr | Lys | Pro | Ser | Lys | Gln |
|---|---|---|---|---|---|---|---|---|---|---|---|---|---|---|---|
| 145 |  |  |  |  | 150 |  |  |  |  | 155 |  |  |  |  | 160 |

| Ser | Asn | Asn | Lys | Tyr | Thr | Ala | Ser | Ser | Tyr | Leu | Ser | Leu | Thr | Pro | Asp |
|---|---|---|---|---|---|---|---|---|---|---|---|---|---|---|---|
|  |  |  |  | 165 |  |  |  |  | 170 |  |  |  |  | 175 |  |

| Lys | Trp | Lys | Ser | His | Ser | Ser | Phe | Ser | Cys | Leu | Val | Thr | His | Gln | Gly |
|---|---|---|---|---|---|---|---|---|---|---|---|---|---|---|---|
|  |  |  |  | 180 |  |  |  |  | 185 |  |  |  |  | 190 |  |

-continued

```
Ser Thr Val Glu Lys Lys Val Ala Pro Ala Glu Cys Ser
        195                 200                 205

<210> SEQ ID NO 84
<211> LENGTH: 786
<212> TYPE: DNA
<213> ORGANISM: Canis familiaris
<220> FEATURE:
<221> NAME/KEY: CDS
<222> LOCATION: (1)..(621)

<400> SEQUENCE: 84 atg tca gtg gcc ctg gga cag atg gcc agg atc acc tgt ggg aga gac       48
Met Ser Val Ala Leu Gly Gln Met Ala Arg Ile Thr Cys Gly Arg Asp
1               5                   10                  15 aac tct gga aga aaa agt gct cac tgg tac cag cag aag cca agc cag       96
Asn Ser Gly Arg Lys Ser Ala His Trp Tyr Gln Gln Lys Pro Ser Gln
            20                  25                  30 gct ccc gtg atg ctt atc gat gat gat tgc ttc cag ccc tca gga ttc      144
Ala Pro Val Met Leu Ile Asp Asp Asp Cys Phe Gln Pro Ser Gly Phe
        35                  40                  45 tct gag caa ttc tca ggc act aac tcg ggg aac aca gcc acc ctg acc      192
Ser Glu Gln Phe Ser Gly Thr Asn Ser Gly Asn Thr Ala Thr Leu Thr
    50                  55                  60 att agt gtg tca aac att gac gac acg ctt tac ata tat aga acg gaa      240
Ile Ser Val Ser Asn Ile Asp Asp Thr Leu Tyr Ile Tyr Arg Thr Glu
65                  70                  75                  80 gtg agc aac att cct gaa tca cag tgt tgg gta ttc ggt gaa ggg acc      288
Val Ser Asn Ile Pro Glu Ser Gln Cys Trp Val Phe Gly Glu Gly Thr
                85                  90                  95 cag ctg acc gtc ctc ggt cag ccc aag tcc tcc ccc ttg gtc aca ctc      336
Gln Leu Thr Val Leu Gly Gln Pro Lys Ser Ser Pro Leu Val Thr Leu
            100                 105                 110 ttc ccg ccc tcc tct gag gag ctc ggc gcc aac aag gct acc ctg gtg      384
Phe Pro Pro Ser Ser Glu Glu Leu Gly Ala Asn Lys Ala Thr Leu Val
        115                 120                 125 tgc ctc atc agc gac ttc tac ccc agt ggc ctg aaa gtg gct tgg aag      432
Cys Leu Ile Ser Asp Phe Tyr Pro Ser Gly Leu Lys Val Ala Trp Lys
    130                 135                 140 gca gat ggc agc acc atc atc cag ggc gtg gaa acc acc aag ccc tcc      480
Ala Asp Gly Ser Thr Ile Ile Gln Gly Val Glu Thr Thr Lys Pro Ser
145                 150                 155                 160 aag cag agc aac aac aag tac acg gcc agc agc tac ctg agc ctg acg      528
Lys Gln Ser Asn Asn Lys Tyr Thr Ala Ser Ser Tyr Leu Ser Leu Thr
                165                 170                 175 cct gac aag tgg aaa tct cac agc agc ttc agc tgc ctg gtc acg cac      576
Pro Asp Lys Trp Lys Ser His Ser Ser Phe Ser Cys Leu Val Thr His
            180                 185                 190 cag ggg agc acc gtg gag aag aag gtg gcc cct gca gag tgc tct           621
Gln Gly Ser Thr Val Glu Lys Lys Val Ala Pro Ala Glu Cys Ser
        195                 200                 205 taggtccctg agaattcctg agatggagcc ttcctcaccc agacacccct tccccagttc    681
accttgtgcc cctgaaaacc caccctggac cagctcagac caggcaggtc actcatcctc    741
cctgtttcta cttgtgctca ataaagactt tatcatttat cactg                    786

<210> SEQ ID NO 85
<211> LENGTH: 207
<212> TYPE: PRT
<213> ORGANISM: Canis familiaris
```

<400> SEQUENCE: 85

Met Ser Val Ala Leu Gly Gln Met Ala Arg Ile Thr Cys Gly Arg Asp
1               5                   10                  15

Asn Ser Gly Arg Lys Ser Ala His Trp Tyr Gln Gln Lys Pro Ser Gln
            20                  25                  30

Ala Pro Val Met Leu Ile Asp Asp Asp Cys Phe Gln Pro Ser Gly Phe
        35                  40                  45

Ser Glu Gln Phe Ser Gly Thr Asn Ser Gly Asn Thr Ala Thr Leu Thr
    50                  55                  60

Ile Ser Val Ser Asn Ile Asp Asp Thr Leu Tyr Ile Tyr Arg Thr Glu
65                  70                  75                  80

Val Ser Asn Ile Pro Glu Ser Gln Cys Trp Val Phe Gly Glu Gly Thr
                85                  90                  95

Gln Leu Thr Val Leu Gly Gln Pro Lys Ser Ser Pro Leu Val Thr Leu
            100                 105                 110

Phe Pro Pro Ser Ser Glu Glu Leu Gly Ala Asn Lys Ala Thr Leu Val
        115                 120                 125

Cys Leu Ile Ser Asp Phe Tyr Pro Ser Gly Leu Lys Val Ala Trp Lys
    130                 135                 140

Ala Asp Gly Ser Thr Ile Ile Gln Gly Val Glu Thr Thr Lys Pro Ser
145                 150                 155                 160

Lys Gln Ser Asn Asn Lys Tyr Thr Ala Ser Ser Tyr Leu Ser Leu Thr
                165                 170                 175

Pro Asp Lys Trp Lys Ser His Ser Ser Phe Ser Cys Leu Val Thr His
            180                 185                 190

Gln Gly Ser Thr Val Glu Lys Lys Val Ala Pro Ala Glu Cys Ser
        195                 200                 205

<210> SEQ ID NO 86
<211> LENGTH: 783
<212> TYPE: DNA
<213> ORGANISM: Canis familiaris
<220> FEATURE:
<221> NAME/KEY: CDS
<222> LOCATION: (1)..(618)

<400> SEQUENCE: 86

```
atg tca gtg gcc ctg gga cag atg gcc agg atc acc tgt ggg aga gac     48
Met Ser Val Ala Leu Gly Gln Met Ala Arg Ile Thr Cys Gly Arg Asp
1               5                   10                  15 aac tct gga aga aaa agt gct cac tgg tac cag cag aag cca agc cag     96
Asn Ser Gly Arg Lys Ser Ala His Trp Tyr Gln Gln Lys Pro Ser Gln
            20                  25                  30 gct ccc gtg atg ctt atc gat gat gat tgc ttc cag ccc tca gga ttc    144
Ala Pro Val Met Leu Ile Asp Asp Asp Cys Phe Gln Pro Ser Gly Phe
        35                  40                  45 tct gag caa ttc tca ggc act aac tcg ggg aac aca gcc acc ctg acc    192
Ser Glu Gln Phe Ser Gly Thr Asn Ser Gly Asn Thr Ala Thr Leu Thr
    50                  55                  60 att agt gga cac cgt gca gaa cca gag gca gaa cat ttc tct ctg tgg    240
Ile Ser Gly His Arg Ala Glu Pro Glu Ala Glu His Phe Ser Leu Trp
65                  70                  75                  80 cca tgc aag tca gat cct ggt tgt tgg gta ttc ggt gaa ggg acc cag    288
Pro Cys Lys Ser Asp Pro Gly Cys Trp Val Phe Gly Glu Gly Thr Gln
                85                  90                  95 ctg acc gtc ctc ggt cag ccc aag tcc tcc ccc ttg gtc aca ctc ttc    336
Leu Thr Val Leu Gly Gln Pro Lys Ser Ser Pro Leu Val Thr Leu Phe
            100                 105                 110
```

```
ccg ccc tcc tct gag gag ctc ggc gcc aac aag gct acc ctg gtg tgc        384
Pro Pro Ser Ser Glu Glu Leu Gly Ala Asn Lys Ala Thr Leu Val Cys
        115                 120                 125 ctc atc agc gac ttc tac ccc agt ggc ctg aaa gtg gct tgg aag gca        432
Leu Ile Ser Asp Phe Tyr Pro Ser Gly Leu Lys Val Ala Trp Lys Ala
    130                 135                 140 gat ggc agc acc atc atc cag ggc gtg gaa acc acc aag ccc tcc aag        480
Asp Gly Ser Thr Ile Ile Gln Gly Val Glu Thr Thr Lys Pro Ser Lys
145                 150                 155                 160 cag agc aac aac aag tac acg gcc agc agc tac ctg agc ctg acg cct        528
Gln Ser Asn Asn Lys Tyr Thr Ala Ser Ser Tyr Leu Ser Leu Thr Pro
                165                 170                 175 gac aag tgg aaa tct cac agc agc ttc agc tgc ctg gtc acg cac cag        576
Asp Lys Trp Lys Ser His Ser Ser Phe Ser Cys Leu Val Thr His Gln
            180                 185                 190 ggg agc acc gtg gag aag aag gtg gcc cct gca gag tgc tct                618
Gly Ser Thr Val Glu Lys Lys Val Ala Pro Ala Glu Cys Ser
        195                 200                 205 taggtccctg agaattcctg agatggagcc ttcctcaccc agacacccct tccccagttc      678
accttgtgcc cctgaaaacc caccctggac cagctcagac caggcaggtc actcatcctc      738
cctgtttcta cttgtgctca ataaagactt tatcatttat cactg                     783

<210> SEQ ID NO 87
<211> LENGTH: 206
<212> TYPE: PRT
<213> ORGANISM: Canis familiaris

<400> SEQUENCE: 87

Met Ser Val Ala Leu Gly Gln Met Ala Arg Ile Thr Cys Gly Arg Asp
1               5                   10                  15

Asn Ser Gly Arg Lys Ser Ala His Trp Tyr Gln Gln Lys Pro Ser Gln
            20                  25                  30

Ala Pro Val Met Leu Ile Asp Asp Cys Phe Gln Pro Ser Gly Phe
        35                  40                  45

Ser Glu Gln Phe Ser Gly Thr Asn Ser Gly Asn Thr Ala Thr Leu Thr
    50                  55                  60

Ile Ser Gly His Arg Ala Glu Pro Glu Ala Glu His Phe Ser Leu Trp
65                  70                  75                  80

Pro Cys Lys Ser Asp Pro Gly Cys Trp Val Phe Gly Glu Gly Thr Gln
                85                  90                  95

Leu Thr Val Leu Gly Gln Pro Lys Ser Ser Pro Leu Val Thr Leu Phe
            100                 105                 110

Pro Pro Ser Ser Glu Glu Leu Gly Ala Asn Lys Ala Thr Leu Val Cys
        115                 120                 125

Leu Ile Ser Asp Phe Tyr Pro Ser Gly Leu Lys Val Ala Trp Lys Ala
    130                 135                 140

Asp Gly Ser Thr Ile Ile Gln Gly Val Glu Thr Thr Lys Pro Ser Lys
145                 150                 155                 160

Gln Ser Asn Asn Lys Tyr Thr Ala Ser Ser Tyr Leu Ser Leu Thr Pro
                165                 170                 175

Asp Lys Trp Lys Ser His Ser Ser Phe Ser Cys Leu Val Thr His Gln
            180                 185                 190

Gly Ser Thr Val Glu Lys Lys Val Ala Pro Ala Glu Cys Ser
        195                 200                 205
```

```
<210> SEQ ID NO 88
<211> LENGTH: 780
<212> TYPE: DNA
<213> ORGANISM: Canis familiaris
<220> FEATURE:
<221> NAME/KEY: CDS
<222> LOCATION: (1)..(615)

<400> SEQUENCE: 88 atg tca gtg gcc ctg gga cag atg gcc agg atc acc tgt ggg aga gac      48
Met Ser Val Ala Leu Gly Gln Met Ala Arg Ile Thr Cys Gly Arg Asp
1               5                   10                  15 aac tct gga aga aaa agt gct cac tgg tac cag cag aag cca agc cag      96
Asn Ser Gly Arg Lys Ser Ala His Trp Tyr Gln Gln Lys Pro Ser Gln
            20                  25                  30 gct ccc gtg atg ctt atc gat gat gat tgc ttc cag ccc tca gga ttc      144
Ala Pro Val Met Leu Ile Asp Asp Asp Cys Phe Gln Pro Ser Gly Phe
        35                  40                  45 tct gag caa ttc tca ggc act aac tcg ggg aac aca gcc acc ctg acc      192
Ser Glu Gln Phe Ser Gly Thr Asn Ser Gly Asn Thr Ala Thr Leu Thr
    50                  55                  60 att agt cag atc cca ccc tac tct gaa gtg act cgc ttc act cgg gcc      240
Ile Ser Gln Ile Pro Pro Tyr Ser Glu Val Thr Arg Phe Thr Arg Ala
65                  70                  75                  80 tgg gca gac act agc tgt tgt tgg gta ttc ggt gaa ggg acc cag ctg      288
Trp Ala Asp Thr Ser Cys Cys Trp Val Phe Gly Glu Gly Thr Gln Leu
                85                  90                  95 acc gtc ctc ggt cag ccc aag tcc tcc ccc ttg gtc aca ctc ttc ccg      336
Thr Val Leu Gly Gln Pro Lys Ser Ser Pro Leu Val Thr Leu Phe Pro
            100                 105                 110 ccc tcc tct gag gag ctc ggc gcc aac aag gct acc ctg gtg tgc ctc      384
Pro Ser Ser Glu Glu Leu Gly Ala Asn Lys Ala Thr Leu Val Cys Leu
        115                 120                 125 atc agc gac ttc tac ccc agt ggc ctg aaa gtg gct tgg aag gca gat      432
Ile Ser Asp Phe Tyr Pro Ser Gly Leu Lys Val Ala Trp Lys Ala Asp
    130                 135                 140 ggc agc acc atc atc cag ggc gtg gaa acc acc aag ccc tcc aag cag      480
Gly Ser Thr Ile Ile Gln Gly Val Glu Thr Thr Lys Pro Ser Lys Gln
145                 150                 155                 160 agc aac aac aag tac acg gcc agc agc tac ctg agc ctg acg cct gac      528
Ser Asn Asn Lys Tyr Thr Ala Ser Ser Tyr Leu Ser Leu Thr Pro Asp
                165                 170                 175 aag tgg aaa tct cac agc agc ttc agc tgc ctg gtc acg cac cag ggg      576
Lys Trp Lys Ser His Ser Ser Phe Ser Cys Leu Val Thr His Gln Gly
            180                 185                 190 agc acc gtg gag aag aag gtg gcc cct gca gag tgc tct taggtccctg      625
Ser Thr Val Glu Lys Lys Val Ala Pro Ala Glu Cys Ser
        195                 200                 205 agaattcctg agatggagcc ttcctcaccc agacacccct tccccagttc accttgtgcc    685
cctgaaaacc caccctggac cagctcagac caggcaggtc actcatcctc cctgtttcta    745
cttgtgctca ataaagactt tatcatttat cactg                              780

<210> SEQ ID NO 89
<211> LENGTH: 205
<212> TYPE: PRT
<213> ORGANISM: Canis familiaris

<400> SEQUENCE: 89

Met Ser Val Ala Leu Gly Gln Met Ala Arg Ile Thr Cys Gly Arg Asp
1               5                   10                  15
```

```
Asn Ser Gly Arg Lys Ser Ala His Trp Tyr Gln Gln Lys Pro Ser Gln
            20                  25                  30

Ala Pro Val Met Leu Ile Asp Asp Cys Phe Gln Pro Ser Gly Phe
        35                  40                  45

Ser Glu Gln Phe Ser Gly Thr Asn Ser Gly Asn Thr Ala Thr Leu Thr
 50                  55                  60

Ile Ser Gln Ile Pro Pro Tyr Ser Glu Val Thr Arg Phe Thr Arg Ala
 65                  70                  75                  80

Trp Ala Asp Thr Ser Cys Cys Trp Val Phe Gly Glu Gly Thr Gln Leu
                85                  90                  95

Thr Val Leu Gly Gln Pro Lys Ser Ser Pro Leu Val Thr Leu Phe Pro
            100                 105                 110

Pro Ser Ser Glu Glu Leu Gly Ala Asn Lys Ala Thr Leu Val Cys Leu
            115                 120                 125

Ile Ser Asp Phe Tyr Pro Ser Gly Leu Lys Val Ala Trp Lys Ala Asp
            130                 135                 140

Gly Ser Thr Ile Ile Gln Gly Val Glu Thr Thr Lys Pro Ser Lys Gln
145                 150                 155                 160

Ser Asn Asn Lys Tyr Thr Ala Ser Ser Tyr Leu Ser Leu Thr Pro Asp
                165                 170                 175

Lys Trp Lys Ser His Ser Ser Phe Ser Cys Leu Val Thr His Gln Gly
            180                 185                 190

Ser Thr Val Glu Lys Lys Val Ala Pro Ala Glu Cys Ser
            195                 200                 205

<210> SEQ ID NO 90
<211> LENGTH: 851
<212> TYPE: DNA
<213> ORGANISM: Canis familiaris
<220> FEATURE:
<221> NAME/KEY: CDS
<222> LOCATION: (24)..(716)

<400> SEQUENCE: 90
agcagaatca gggtgcctcc acc atg gcc tgg acc cac ctc ctc ctg agc ctc     53
                        Met Ala Trp Thr His Leu Leu Leu Ser Leu
                          1               5                  10 ctg gct ctc tgc aca ggt tct gtg gcc tcc tat gtg ctg aca cag ctg    101
Leu Ala Leu Cys Thr Gly Ser Val Ala Ser Tyr Val Leu Thr Gln Leu
            15                  20                  25 cca tcc aaa aat gtg acc ctg aag cag ccg gcc cac atc acc tgt ggg    149
Pro Ser Lys Asn Val Thr Leu Lys Gln Pro Ala His Ile Thr Cys Gly
        30                  35                  40 gga gac aac att gga agt aaa agt gtt cac tgg tac cag cag aag ctg    197
Gly Asp Asn Ile Gly Ser Lys Ser Val His Trp Tyr Gln Gln Lys Leu
    45                  50                  55 ggc cag gcc cct gta ctg att atc tat tat gat agc agc agg ccg aca    245
Gly Gln Ala Pro Val Leu Ile Ile Tyr Tyr Asp Ser Ser Arg Pro Thr
 60                  65                  70 ggg atc cct gag cga ttc tcc ggc gcc aac tcg ggg aac acg gcc acc    293
Gly Ile Pro Glu Arg Phe Ser Gly Ala Asn Ser Gly Asn Thr Ala Thr
 75                  80                  85                  90 ctg acc atc agc ggg gcc ctg gcc gag gac gag gct gac tat tac tgc    341
Leu Thr Ile Ser Gly Ala Leu Ala Glu Asp Glu Ala Asp Tyr Tyr Cys
                95                 100                 105 cag gtg tgg gac agc agt gct ctt gtg ttc ggc gga ggc acc cat ctg    389
Gln Val Trp Asp Ser Ser Ala Leu Val Phe Gly Gly Gly Thr His Leu
            110                 115                 120
```

```
acc gtc ctc ggt cag ccc aag gcc tcc ccc tcg gtc aca ctc ttc ccg      437
Thr Val Leu Gly Gln Pro Lys Ala Ser Pro Ser Val Thr Leu Phe Pro
            125                 130                 135 ccc tcc tct gag gag ctc ggc gcc aac aag gcc acc ctg gtg tgc ctc      485
Pro Ser Ser Glu Glu Leu Gly Ala Asn Lys Ala Thr Leu Val Cys Leu
    140                 145                 150 atc agc gac ttc tac ccc agt ggc gtg acg gtg gcc tgg aag gca gac      533
Ile Ser Asp Phe Tyr Pro Ser Gly Val Thr Val Ala Trp Lys Ala Asp
155                 160                 165                 170 ggc agc ccc gtc acc cag ggc gtg gag acc acc aag ccc tcc aag cag      581
Gly Ser Pro Val Thr Gln Gly Val Glu Thr Thr Lys Pro Ser Lys Gln
                175                 180                 185 agc aac aac aag tac gcg gcc agc agc tac ctg agc ctg acg cct gac      629
Ser Asn Asn Lys Tyr Ala Ala Ser Ser Tyr Leu Ser Leu Thr Pro Asp
            190                 195                 200 aag tgg aaa tct cac agc agc ttc agc tgc ctg gtc aca cac gag ggg      677
Lys Trp Lys Ser His Ser Ser Phe Ser Cys Leu Val Thr His Glu Gly
    205                 210                 215 agc acc gtg gag aag aag gtg gcc ccc gca gag tgc tct taggttcccg      726
Ser Thr Val Glu Lys Lys Val Ala Pro Ala Glu Cys Ser
220                 225                 230 acgccccgc ccacctaagg gggcccggag cctcaggacc tccaggagga tcttgcctcc     786
tatctgggtc atcccgccct tctccccaca cccaggcagc actcaataaa gtgttctttg   846
ttcaa                                                                851

<210> SEQ ID NO 91
<211> LENGTH: 231
<212> TYPE: PRT
<213> ORGANISM: Canis familiaris

<400> SEQUENCE: 91

Met Ala Trp Thr His Leu Leu Ser Leu Leu Ala Leu Cys Thr Gly
1               5                   10                  15

Ser Val Ala Ser Tyr Val Leu Thr Gln Leu Pro Ser Lys Asn Val Thr
            20                  25                  30

Leu Lys Gln Pro Ala His Ile Thr Cys Gly Gly Asp Asn Ile Gly Ser
        35                  40                  45

Lys Ser Val His Trp Tyr Gln Gln Lys Leu Gly Gln Ala Pro Val Leu
    50                  55                  60

Ile Ile Tyr Tyr Asp Ser Ser Arg Pro Thr Gly Ile Pro Glu Arg Phe
65                  70                  75                  80

Ser Gly Ala Asn Ser Gly Asn Thr Ala Thr Leu Thr Ile Ser Gly Ala
                85                  90                  95

Leu Ala Glu Asp Glu Ala Asp Tyr Tyr Cys Gln Val Trp Asp Ser Ser
            100                 105                 110

Ala Leu Val Phe Gly Gly Gly Thr His Leu Thr Val Leu Gly Gln Pro
        115                 120                 125

Lys Ala Ser Pro Ser Val Thr Leu Phe Pro Pro Ser Ser Glu Glu Leu
    130                 135                 140

Gly Ala Asn Lys Ala Thr Leu Val Cys Leu Ile Ser Asp Phe Tyr Pro
145                 150                 155                 160

Ser Gly Val Thr Val Ala Trp Lys Ala Asp Gly Ser Pro Val Thr Gln
                165                 170                 175

Gly Val Glu Thr Thr Lys Pro Ser Lys Gln Ser Asn Asn Lys Tyr Ala
            180                 185                 190

Ala Ser Ser Tyr Leu Ser Leu Thr Pro Asp Lys Trp Lys Ser His Ser
```

```
            195                 200                 205
Ser Phe Ser Cys Leu Val Thr His Glu Gly Ser Thr Val Glu Lys Lys
    210                 215                 220

Val Ala Pro Ala Glu Cys Ser
225                 230

<210> SEQ ID NO 92
<211> LENGTH: 881
<212> TYPE: DNA
<213> ORGANISM: Canis familiaris
<220> FEATURE:
<221> NAME/KEY: CDS
<222> LOCATION: (18)..(716)

<400> SEQUENCE: 92
atcagggtgc ctccacc atg gcc tgg acc cac ctc ctc ctg agc ctc ctg        50
                   Met Ala Trp Thr His Leu Leu Leu Ser Leu Leu
                    1               5                   10 gct ctc tgc aca ggt tct gtg gcc tcc tat gtg ctg aca cag ctg cca       98
Ala Leu Cys Thr Gly Ser Val Ala Ser Tyr Val Leu Thr Gln Leu Pro
             15                  20                  25 tcc aaa aat gtg acc ctg aag cag ccg gcc cac atc acc tgt ggg gga     146
Ser Lys Asn Val Thr Leu Lys Gln Pro Ala His Ile Thr Cys Gly Gly
         30                  35                  40 gac aac att gga agt aaa agt gtt cac tgg tac cag cag aag ctg ggc     194
Asp Asn Ile Gly Ser Lys Ser Val His Trp Tyr Gln Gln Lys Leu Gly
 45                  50                  55 cag gcc cct gta ctg att atc tat tat gat agc agc agg ccg aca ggg     242
Gln Ala Pro Val Leu Ile Ile Tyr Tyr Asp Ser Ser Arg Pro Thr Gly
 60                  65                  70                  75 atc cct gag cga ttc tcc ggc gcc aac tcg ggg aac acg gcc acc ctg     290
Ile Pro Glu Arg Phe Ser Gly Ala Asn Ser Gly Asn Thr Ala Thr Leu
                 80                  85                  90 acc atc agc ggg gcc ctg gcc gag gac gag gct gac tat tac tgc cag     338
Thr Ile Ser Gly Ala Leu Ala Glu Asp Glu Ala Asp Tyr Tyr Cys Gln
             95                 100                 105 gtg tgg gac agc agt ggt cat tgt tgg gta ttc ggt gaa ggg acc cag     386
Val Trp Asp Ser Ser Gly His Cys Trp Val Phe Gly Glu Gly Thr Gln
        110                 115                 120 ctg acc gtc ctc ggt cag ccc aag tcc tcc ccc ttg gtc aca ctc ttc     434
Leu Thr Val Leu Gly Gln Pro Lys Ser Ser Pro Leu Val Thr Leu Phe
125                 130                 135 ccg ccc tcc tct gag gag ctc ggc gcc aac aag gct acc ctg gtg tgc     482
Pro Pro Ser Ser Glu Glu Leu Gly Ala Asn Lys Ala Thr Leu Val Cys
140                 145                 150                 155 ctc atc agc gac ttc tac ccc agt ggc ctg aaa gtg gct tgg aag gca     530
Leu Ile Ser Asp Phe Tyr Pro Ser Gly Leu Lys Val Ala Trp Lys Ala
                160                 165                 170 gat ggc agc acc atc atc cag ggc gtg gaa acc acc aag ccc tcc aag     578
Asp Gly Ser Thr Ile Ile Gln Gly Val Glu Thr Thr Lys Pro Ser Lys
            175                 180                 185 cag agc aac aac aag tac acg gcc agc agc tac ctg agc ctg acg cct     626
Gln Ser Asn Asn Lys Tyr Thr Ala Ser Ser Tyr Leu Ser Leu Thr Pro
        190                 195                 200 gac aag tgg aaa tct cac agc agc ttc agc tgc ctg gtc acg cac cag     674
Asp Lys Trp Lys Ser His Ser Ser Phe Ser Cys Leu Val Thr His Gln
    205                 210                 215 ggg agc acc gtg gag aag aag gtg gcc cct gca gag tgc tct              716
Gly Ser Thr Val Glu Lys Lys Val Ala Pro Ala Glu Cys Ser
220                 225                 230
```

```
taggtccctg agaattcctg agatggagcc ttcctcaccc agacacccct tccccagttc    776
accttgtgcc cctgaaaacc caccctggac cagctcagac caggcaggtc actcatcctc    836
cctgtttcta cttgtgctca ataaagactt tatcatttat cactg                    881
```

<210> SEQ ID NO 93
<211> LENGTH: 233
<212> TYPE: PRT
<213> ORGANISM: Canis familiaris

<400> SEQUENCE: 93

```
Met Ala Trp Thr His Leu Leu Ser Leu Leu Ala Leu Cys Thr Gly
1               5                   10                  15

Ser Val Ala Ser Tyr Val Leu Thr Gln Leu Pro Ser Lys Asn Val Thr
            20                  25                  30

Leu Lys Gln Pro Ala His Ile Thr Cys Gly Gly Asp Asn Ile Gly Ser
        35                  40                  45

Lys Ser Val His Trp Tyr Gln Gln Lys Leu Gly Gln Ala Pro Val Leu
    50                  55                  60

Ile Ile Tyr Tyr Asp Ser Ser Arg Pro Thr Gly Ile Pro Glu Arg Phe
65                  70                  75                  80

Ser Gly Ala Asn Ser Gly Asn Thr Ala Thr Leu Thr Ile Ser Gly Ala
                85                  90                  95

Leu Ala Glu Asp Glu Ala Asp Tyr Tyr Cys Gln Val Trp Asp Ser Ser
            100                 105                 110

Gly His Cys Trp Val Phe Gly Glu Gly Thr Gln Leu Thr Val Leu Gly
        115                 120                 125

Gln Pro Lys Ser Ser Pro Leu Val Thr Leu Phe Pro Pro Ser Ser Glu
    130                 135                 140

Glu Leu Gly Ala Asn Lys Ala Thr Leu Val Cys Leu Ile Ser Asp Phe
145                 150                 155                 160

Tyr Pro Ser Gly Leu Lys Val Ala Trp Lys Ala Asp Gly Ser Thr Ile
                165                 170                 175

Ile Gln Gly Val Glu Thr Thr Lys Pro Ser Lys Gln Ser Asn Asn Lys
            180                 185                 190

Tyr Thr Ala Ser Ser Tyr Leu Ser Leu Thr Pro Asp Lys Trp Lys Ser
        195                 200                 205

His Ser Ser Phe Ser Cys Leu Val Thr His Gln Gly Ser Thr Val Glu
    210                 215                 220

Lys Lys Val Ala Pro Ala Glu Cys Ser
225                 230
```

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94

```
aattaaccct cactaaaggg                                                 20
```

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Synthetic

```
                T7 primer

<400> SEQUENCE: 95
taatacgact cactatagg                                                  19

<210> SEQ ID NO 96
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ctgaccgtcc tcggtcag                                                   18

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ccttcttctc cacggtgc                                                   18

<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
tggtaaccca tggcctgc                                                   18

<210> SEQ ID NO 99
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
accgtcttct ccacggtg                                                   18

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence: Synthetic
      GAPDH primer

<400> SEQUENCE: 100
gggctgcttt taactctg                                                   18

<210> SEQ ID NO 101
<211> LENGTH: 18
<212> TYPE: DNA
<213> ORGANISM: Artificial Sequence
<220> FEATURE:
<223> OTHER INFORMATION: Description of Artificial Sequence: Synthetic
      GAPDH primer
```

<400> SEQUENCE: 101
ccaggaaatg agcttgac				18

<210> SEQ ID NO 102
<211> LENGTH: 10
<212> TYPE: PRT
<213> ORGANISM: Mus musculus

<400> SEQUENCE: 102

Arg Asp Tyr Gly Tyr Gly Tyr Phe Asp Tyr
1               5                   10

<210> SEQ ID NO 103
<211> LENGTH: 17
<212> TYPE: PRT
<213> ORGANISM: Mus musculus

<400> SEQUENCE: 103

Asp Ile Asn Pro Asn Asn Gly Gly Thr Thr Tyr Asn Gln Lys Phe Lys
1               5                   10                  15

Gly

<210> SEQ ID NO 104
<211> LENGTH: 5
<212> TYPE: PRT
<213> ORGANISM: Mus musculus

<400> SEQUENCE: 104

Asp Tyr Tyr Met Lys
1               5

<210> SEQ ID NO 105
<211> LENGTH: 137
<212> TYPE: PRT
<213> ORGANISM: Mus musculus

<400> SEQUENCE: 105

Met Gly Trp Ser Cys Ile Met Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asp Tyr Tyr Met Lys Trp Met Lys Gln Ser His Gly Lys Ser Leu
    50                  55                  60

Glu Trp Ile Gly Asp Ile Asn Pro Asn Asn Gly Gly Thr Thr Tyr Asn
65                  70                  75                  80

Gln Lys Phe Lys Gly Lys Ala Thr Leu Thr Val Asp Lys Ser Ser Ser
                85                  90                  95

Thr Ala Tyr Met Gln Leu Asn Ser Leu Thr Ser Glu Asp Ser Ala Val
            100                 105                 110

Tyr Tyr Cys Ala Arg Asp Tyr Gly Tyr Gly Tyr Phe Asp Tyr Trp Gly
        115                 120                 125

Gln Gly Thr Thr Leu Thr Val Ser Ser
    130                 135

<210> SEQ ID NO 106
<211> LENGTH: 9
<212> TYPE: PRT

<213> ORGANISM: Mus musculus

<400> SEQUENCE: 106

Arg Ala Ser Glu Asn Ile Tyr Ser Asn
1               5

<210> SEQ ID NO 107
<211> LENGTH: 7
<212> TYPE: PRT
<213> ORGANISM: Mus musculus

<400> SEQUENCE: 107

Ala Ala Thr Asn Leu Ala Asp
1               5

<210> SEQ ID NO 108
<211> LENGTH: 8
<212> TYPE: PRT
<213> ORGANISM: Mus musculus

<400> SEQUENCE: 108

Gln His Phe Trp Gly Thr Trp Thr
1               5

<210> SEQ ID NO 109
<211> LENGTH: 126
<212> TYPE: PRT
<213> ORGANISM: Mus musculus

<400> SEQUENCE: 109

Met Ser Val Leu Thr Gln Val Leu Gly Leu Leu Leu Trp Leu Thr
1               5                   10                  15

Asp Ala Arg Cys Asp Ile Gln Met Thr Gln Ser Pro Ala Ser Leu Ser
            20                  25                  30

Val Ser Val Gly Glu Thr Val Thr Ile Thr Cys Arg Ala Ser Glu Asn
        35                  40                  45

Ile Tyr Ser Asn Leu Ala Trp Tyr Gln Gln Lys Gln Gly Lys Ser Pro
    50                  55                  60

Gln Leu Leu Val Tyr Ala Ala Thr Asn Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Phe Gly Ser Tyr Tyr Cys Gln His Phe Trp
            100                 105                 110

Gly Thr Trp Thr Phe Gly Gly Gly Thr Thr Leu Glu Ile Lys
        115                 120                 125

<210> SEQ ID NO 110
<211> LENGTH: 411
<212> TYPE: DNA
<213> ORGANISM: Mus musculus

<400> SEQUENCE: 110
atgggatgga gctgtatcat gctcttcctc ttgtcaggaa ctgcaggtgt cctctctgag    60
gtccagctgc aacaatctgg acctgagctg gtgaagcctg gggcttcagt gaagatgtcc   120
tgtaaggctt ctggatacac attcactgac tactacatga agtggatgaa gcagagtcat   180
ggaaagagcc ttgagtggat tgagatatt aatcctaaca atggtggtac tacctacaac   240
cagaagttca aggcaaggc cacattgact gtagacaaat cctccagcac agcctacatg   300

```
cagctcaaca gcctgacatc tgaggactct gcagtctatt actgtgcaag agactacggc        360
tacggctact ttgactactg gggccaaggc accactctca cagtctcctc a                 411
```

<210> SEQ ID NO 111
<211> LENGTH: 378
<212> TYPE: DNA
<213> ORGANISM: Mus musculus

<400> SEQUENCE: 111

```
atgagtgtgc tcactcaggt cctggggttg ctgctgctgt ggcttacaga tgccagatgt        60
gacatccaga tgactcagtc tccagcctcc ctatctgtat ctgtgggaga aactgtcacc        120
atcacatgtc gagcaagtga gaatatttat agtaatttag catggtatca gcagaaacag        180
ggaaaatctc ctcagctcct ggtctatgct gcaacaaact tagcagatgg tgtgccatca        240
aggttcagtg gcagtggatc aggcacacag tattccctca agatcaacag cctgcagtct        300
gaagattttg ggagttatta ctgtcaacat ttttggggta cttggacgtt cggtggaggc        360
accaccctgg aaatcaaa                                                      378
```

<210> SEQ ID NO 112
<211> LENGTH: 36
<212> TYPE: DNA
<213> ORGANISM: Mus musculus

<400> SEQUENCE: 112

```
actagtcgac atgggatgga gctrtatcat sytctt                                  36
```

<210> SEQ ID NO 113
<211> LENGTH: 33
<212> TYPE: DNA
<213> ORGANISM: Mus musculus

<400> SEQUENCE: 113

```
ggaagatcta gggaccaagg gatagacagt tgg                                     33
```

<210> SEQ ID NO 114
<211> LENGTH: 40
<212> TYPE: DNA
<213> ORGANISM: Mus musculus

<400> SEQUENCE: 114

```
actagtcgac atgagtgtgc tcactcaggt cctggsgttg                              40
```

<210> SEQ ID NO 115
<211> LENGTH: 30
<212> TYPE: DNA
<213> ORGANISM: Mus musculus

<400> SEQUENCE: 115

```
ggtgcatgcg gatacagttg gtgcagcatc                                         30
```

<210> SEQ ID NO 116
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116

```
agtcacgacg ttgta                                                         15
```

```
<210> SEQ ID NO 117
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
caggaaacag ctatgac                                                    17

<210> SEQ ID NO 118
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 118

His His His His His His
1               5

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 119

His His His His His His His His His His
1               5                   10

<210> SEQ ID NO 120
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Gly Gly Gly Ser Gly Gly Gly Gly Ser Gly Gly Gly Gly Ser
1               5                   10                  15

<210> SEQ ID NO 121
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tttttttttt tttttttttt tttttttttt                                      30
```

PHARMACEUTICAL COMPOSITION FOR TREATMENT AND PREVENTION OF CANCER

PRIORITY PARAGRAPH

This application is a divisional application of U.S. patent application Ser. No. 13/002,636, filed Feb. 15, 2011, now U.S. Pat. No. 10,611,835, issued on Apr. 7, 2020, which is a U.S. National Phase Application under 35 U.S.C. 371 of International Patent Application No. PCT/JP2009/062573 filed Jul. 10, 2009, which claims priority to Japanese Application Serial No. 2008-180057 filed on Jul. 10, 2008, and to Japanese Application Serial No. 2009-087379 filed on Mar. 31, 2009, the content of each of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Feb. 24, 2020, is named 2205705_121_US2_SL.txt and is 247,753 bytes in size.

TECHNICAL FIELD

The present invention relates to a novel pharmaceutical use of an antibody against CD179b or a fragment thereof, as an agent for therapy and/or prophylaxis of cancer.

BACKGROUND ART

Cancers are the commonest cause for death among all of the causes for death, and the therapies currently carried out therefor are mainly surgical treatment in combination with radiotherapy and chemotherapy. In spite of the developments of new surgical methods and discovery of new anti-cancer agents in recent years, treatment results of cancers are not improved very much at present except for some cancers. In recent years, by virtue of development in molecular biology and cancer immunology, cancer antigens recognized by antibodies and cytotoxic T cells which are specifically reactive with cancers, as well as the genes encoding the cancer antigens, were identified, and expectations for therapeutic methods specifically targeting cancer antigens have been raised (Non-patent Literature 1).

In a therapeutic method for cancer, to reduce side effects, it is desired that the peptide, polypeptide or protein recognized as the antigen exist hardly in normal cells and exist specifically in cancer cells. In 1991, Boon et al. in Ludwig Institute in Belgium isolated a human melanoma antigen MAGE 1 recognized by CD8-positive T cells by a cDNA-expression cloning method using an autologous cancer cell line and cancer-reactive T cells (Non-patent Literature 2). Thereafter, the SEREX (serological identifications of antigens by recombinant expression cloning) method, wherein tumor antigens recognized by antibodies produced in the living body of a cancer patient in response to the cancer of the patient himself are identified by application of a gene expression cloning method, was reported (Non-patent Literature 3; Patent Literature 1), and several cancer antigens which are hardly expressed in normal cells while being specifically expressed in cancer cells have been isolated by this method (Non-patent Literatures 4 to 9). Further, using a part thereof as targets, clinical tests for cell therapies using immunocytes specifically reactive with the cancer antigens, and cancer-specific immunotherapies such as those using vaccines containing the cancer antigens have been carried out.

On the other hand, in recent years, various antibody drugs for therapy of cancer have become conspicuous in the world, which drugs target antigen proteins on cancer cells. Since certain levels of pharmacological effects can be obtained with such antibody drugs as cancer-specific therapeutic agents, they are drawing attention, but most of the antigen proteins to be targeted are those also expressed in normal cells, so that, as a result of administration of the antibody, not only cancer cells, but also normal cells expressing the antigen are damaged, resulting in occurrence of side effects, which has been problematic. Thus, it is expected that identification of cancer antigens specifically expressed on the surfaces of cancer cells and employment of antibodies targeting these as drugs will allow therapy with antibody drugs with less side effects.

CD179b is known to be a part of the surrogate light chain of immunoglobulin and expressed on the membrane surfaces of precursor cells of B cells (pre-B cells and pro-B cells). It disappears upon differentiation of B cells and is not expressed in mature B cells. However, CD179b is known to be expressed in leukemia (pre-B cell leukemia) cells produced by cancerization of pre-B cells (Non-patent Literatures 10 and 11). Further, CD179b is known to be expressed also in lymphoma (pre-B cell lymphoma) cells produced by cancerization of pre-B cells, and able to be used as a diagnostic marker for pre-B cell lymphoma (Non-patent Literature 12). However, its specific expression has not been reported for leukemia cells other than pre-B cell leukemia cells, lymphomas other than pre-B cell lymphoma, breast cancer cells and the like. Further, there has been no report suggesting that antibodies against CD179b are useful for therapy and/or prophylaxis of cancer.

PRIOR ART LITERATURES

Patent Literature

Patent Literature 1: U.S. Pat. No. 5,698,396 B

Non-Patent Literatures

Non-patent Literature 1: Tsuyoshi Akiyoshi, "Cancer and Chemotherapy", 1997, Vol. 24, pp. 551-519
Non-patent Literature 2: Bruggen P. et al., Science, 254: 1643-1647 (1991)
Non-patent Literature 3: Proc. Natl. Acad. Sci. USA, 92:11810-11813 (1995)
Non-patent Literature 4: Int. J. Cancer, 72:965-971 (1997)
Non-patent Literature 5: Cancer Res., 58:1034-1041 (1998)
Non-patent Literature 6: Int. J. Cancer, 29:652-658 (1998)
Non-patent Literature 7: Int. J. Oncol., 14:703-708 (1999)
Non-patent Literature 8: Cancer Res., 56:4766-4772 (1996)
Non-patent Literature 9: Hum. Mol. Genet 6:33-39 (1997)
Non-patent Literature 10: Adv. Immunol., 63:1-41 (1996)
Non-patent Literature 11: Blood, 92:4317-4324 (1998)
Non-patent Literature 12: Modern Pathology, 17:423-429 (2004)

DISCLOSURE OF THE INVENTION

Problems to be Solved by the Invention

The present invention aims to identify cancer antigen proteins specifically expressed on the surfaces of cancer cells and provide uses of antibodies targeting them as agents for therapy and/or prophylaxis of cancer.

Means for Solving the Problems

The present inventors intensively studied to obtain, by the SEREX method using serum from a patient dog from which a canine breast cancer tissue-derived cDNA library was prepared, cDNA encoding a protein which binds to antibodies existing in the serum derived from the cancer-bearing living body, and, based on a human gene homologous to the obtained gene, human CD179b having the amino acid sequence shown in SEQ ID NO:3 was prepared. Further, the present inventors discovered that CD179b is hardly expressed in normal tissues, but specifically expressed in breast cancer, leukemia and lymphoma cells. Further, the present inventors discovered that antibodies against such CD179b damage cancer cells expressing CD179b, thereby completing the present invention.

Thus, the present invention has the following characteristics.

The present invention provides a pharmaceutical composition for therapy and/or prophylaxis of cancer comprising as an effective component an antibody or a fragment thereof, the antibody having immunoreactivity to a CD179b protein having the amino acid sequence shown in SEQ ID NO:3 or an amino acid sequence having a sequence identity of not less than 60% with the amino acid sequence, or to a fragment thereof comprising not less than 7 continuous amino acids.

In its mode, the above cancer is a cancer expressing the CD179b gene.

In another mode, the above cancer is breast cancer, leukemia or lymphoma.

In another mode, the antibody is a monoclonal antibody or a polyclonal antibody.

In another mode, the antibody is a human antibody, humanized antibody, chimeric antibody, single-chain antibody or bispecific antibody.

In another mode, the above antibody is an antibody comprising a heavy chain variable region having the amino acid sequences shown in SEQ ID NOs:103, 104 and 102 and a light chain variable region having the amino acid sequences shown in SEQ ID NOs:106, 107 and 108, the antibody having immunoreactivity to a CD179b protein.

In another mode, the above antibody is an antibody comprising a heavy chain variable region having the amino acid sequence shown in SEQ ID NO:105 and a light chain variable region having the amino acid sequence shown in SEQ ID NO:109, the antibody having immunoreactivity to a CD179b protein.

The present invention further provides the following antibodies.

(i) An antibody comprising a heavy chain variable region having the amino acid sequences shown in SEQ ID NOs: 103, 104 and 102 and a light chain variable region having the amino acid sequences shown in SEQ ID NOs:106, 107 and 108, the antibody having immunoreactivity to a CD179b protein.

(ii) An antibody comprising a heavy chain variable region having the amino acid sequence shown in SEQ ID NO:105 and a light chain variable region having the amino acid sequence shown in SEQ ID NO:109, the antibody having immunoreactivity to a CD179b protein.

(iii) The antibodies of the above (i) and (ii), having cytotoxic activity. In some embodiments, the antibody is conjugated to a cytotoxic moiety capable of inhibiting the proliferation and/or survival of the leukemia cells.

(iv) The antibodies of the above (i) and (ii), each of which is a humanized antibody, chimeric antibody, single-chain antibody or bispecific antibody.

The present invention further provides the following polypeptides or DNAs.

(v) A DNA encoding a polypeptide having the amino acid sequence shown in SEQ ID NO:105, or a DNA encoding the polypeptide.

(vi) A DNA encoding a polypeptide having the amino acid sequence shown in SEQ ID NO:109, or a DNA encoding the polypeptide.

(vii) A DNA having the base sequence shown in SEQ ID NO:110.

(viii) A DNA having the base sequence shown in SEQ ID NO:111.

(ix) A heavy-chain complementarity-determining region (CDR) polypeptide selected from the group consisting of the amino acid sequences shown in SEQ ID NOs:103, 104 and 102, or a DNA encoding the polypeptide.

(x) A light-chain complementarity-determining region (CDR) polypeptide selected from the group consisting of the amino acid sequences shown in SEQ ID NOs:106, 107 and 108, or a DNA encoding the polypeptide.

Effect of the Invention

The antibody against CD179b, which is used in the present invention damages cancer cells. Therefore, the antibody against CD179b is useful for therapy and/or prophylaxis of cancer.

BEST MODE FOR CARRYING OUT THE INVENTION

Figure 1:
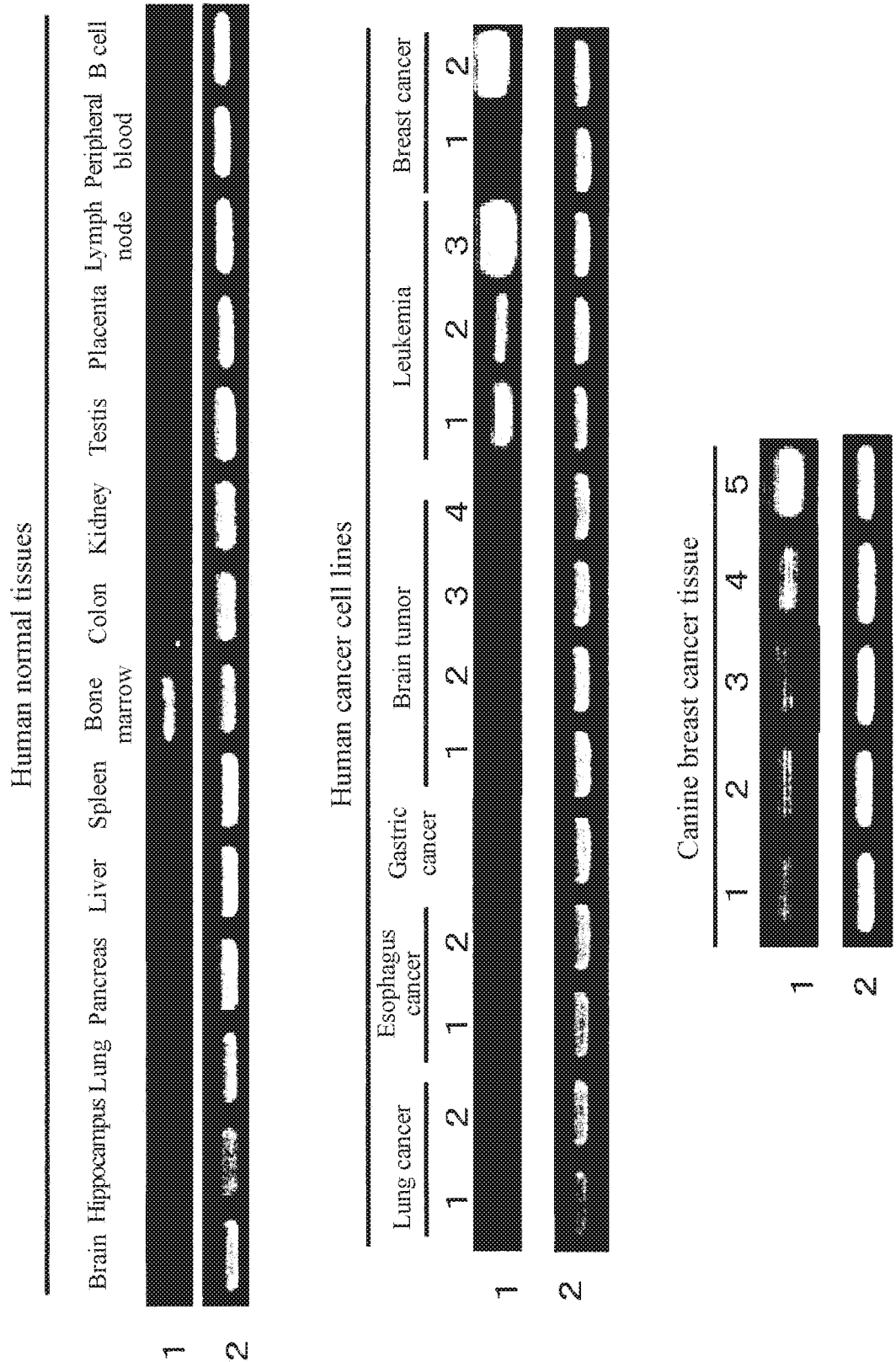
FIG. 1 is a diagram showing the expression patterns of the gene encoding the CD179b protein in normal tissues and tumor cell lines. Reference numeral 1 represents the expression pattern of the gene encoding the CD179b protein; and reference numeral 2 represents the expression pattern of the GAPDH gene.

The amino acid sequence shown in SEQ ID NO:3 in SEQUENCE LISTING disclosed in the present invention is the amino acid sequence of CD179b isolated, by the SEREX method using serum from a patient dog from which a canine mammary gland cancer tissue-derived cDNA library was prepared, as a human homologous factor (homologue) of a polypeptide which binds to antibodies specifically existing in the serum derived from the cancer-bearing dog (see Example 1). The antibody against CD179b used in the present invention may be any type of antibody as long as the antibody can exert an anti-tumor activity, and examples thereof include monoclonal antibodies, polyclonal antibodies, synthetic antibodies, multispecific antibodies, human antibodies, humanized antibodies, chimeric antibodies, single chain antibodies (scFv), and antibody fragments such as Fab and F(ab')2. These antibodies and fragments thereof can be prepared by methods known to those skilled in the art. In the present invention, the antibody can preferably specifically bind to a CD179b protein, and, in cases where the subject is a human, the antibody is preferably a human antibody or a humanized antibody in order to avoid or suppress rejection reaction.

Here, the term "specifically bind to a CD179b protein" means that the antibody specifically binds to a CD179b protein and does not substantially bind to other proteins.

In the present invention, the antibody against CD179b employed may be commercially available. Examples of known antibodies against human CD179b include clones such as GA170, H-60, HP6054, A-19, C-16, SLC1, SLC2, SLC3, SLC4 and HSL11, which are available.

The anti-tumor activity of the antibody which may be used in the present invention can be assayed in vitro by investigating whether or not the antibody shows cytotoxicity against tumor cells expressing the polypeptide via immunocytes or complement, as mentioned later.

Further, the subject of the present invention to be subjected to the therapy and/or prophylaxis of cancer is a mammal such as a human, pet animal, domestic animal or sport animal, and the subject is preferably human.

The terms "cancer" and "tumor" used in the present specification mean a malignant neoplasm, and are used interchangeably.

Preparation of antigens, preparation of antibodies, and pharmaceutical compositions, related to the present invention will now be described.

<Preparation of Antigens for Preparation of Antibodies>

The animal species from which the protein or a fragment thereof used as a sensitizing antigen to obtain an antibody against CD179b used in the present invention is derived is not restricted, and examples thereof include human, dog, bovine, mouse and rat. However, the animal species is preferably selected in consideration of the compatibility with the parent cells used for cell fusion, and, in general, a protein derived from a mammal, especially human, is preferred. For example, in cases where the CD179b is human CD179b, a human CD179b protein or a partial peptide thereof, cells expressing human CD179b, or the like may be used.

The base sequences and the amino acid sequences of human CD179b and homologues thereof can be obtained by, for example, accessing GENBANK$^{SM}$ (NCBI, USA) and using an algorithm such as BLAST or FASTA (Karlin and Altschul, Proc. Natl. Acad. Sci. U.S.A., 90:5873-5877, 1993; Altschul et al., Nucleic Acids Res., 25:3389-3402, 1997). CD179b is also called as λ5, IGLL1, Vpreb2, LOC608248 or the like, but "CD179b" is used as a representative in the present specification. For example, human CD179b is registered under the numbers such as NM_152855 and NM_020070; murine Vpreb2 is registered under the numbers such as NM_016983; and canine LOC608248 is registered under the numbers such as XM_845215.

In the present invention, in cases where the base sequence or the amino acid sequence of human CD179b is used as a standard, a nucleic acid or a protein is targeted which has a sequence showing a sequence identity of 50% to 100%, preferably 60% to 100%, more preferably 80% to 100%, still more preferably 90% to 100%, most preferably 95% to 100%, for example, 97% to 100%, 98% to 100%, 99% to 10% or 99.5% to 100% to the sequence shown in SEQ ID NO:1 or 3. Here, the term "% sequence identity" means the percentage (%) of identical amino acids (or bases) with respect to the total number of amino acids (or bases) when two sequences are aligned with each other such that the maximum similarity is achieved therebetween with or without introduction of a gap(s).

The length of the fragment of the CD179b protein is not less than the length of amino acids of the epitope (antigenic determinant), which is the shortest unit recognized by the antibody, and less than the total length of the protein. The length of the epitope is normally within the range of 7 to 12 continuous amino acids.

The above-described human CD179b protein and polypeptides containing its partial peptides can be synthesized by a chemical synthesis method such as the Fmoc method (fluorenyl-methyloxycarbonyl method) or the tBoc method (t-butyloxycarbonyl method). Further, they can be synthesized by conventional methods using various types of commercially available peptide synthesizers. Further, the polypeptide of interest can be obtained using known genetic engineering techniques, by preparing a polynucleotide encoding the above polypeptide and incorporating the polynucleotide into an expression vector, which is then introduced into a host cell, followed by allowing the polypeptide to be produced in the host cell.

The polynucleotide encoding the above polypeptide can be easily prepared by a known genetic engineering technique or a conventional method using a commercially available nucleic acid synthesizer. For example, DNA having the base sequence shown in SEQ ID NO:1 can be prepared by carrying out PCR using human chromosomal DNA or a human cDNA library as a template, and a pair of primers designed such that the base sequence shown in SEQ ID NO:1 can be amplified therewith. The reaction conditions for the PCR can be set appropriately, and examples thereof include, but are not limited to, repeating the reaction process of 94° C. for 30 seconds (denaturation), 55° C. for 30 seconds to 1 minute (annealing) and 72° C. for 2 minutes (extension) for, for example, 30 cycles, followed by the reaction at 72° C. for 7 minutes. Further, the desired DNA can be isolated by preparing an appropriate probe(s) or primer(s) based on the information of the base sequence and the amino acid sequence shown in SEQ ID NOs:1 and 3, respectively, in SEQUENCE LISTING in the present specification, and using the probe(s) or primer(s) for screening of a cDNA library of human or the like.

The cDNA library is preferably prepared from cells, an organ or a tissue expressing the protein of SEQ ID NO:3. Examples of such cells and a tissue include bone marrow, leukemia cells, breast cancer cells and lymphoma cells. The above-described operations such as preparation of the probe(s) or primer(s), construction of a cDNA library, screening of the cDNA library and cloning of the gene of interest are known to those skilled in the art, and can be carried out according to the methods described in, for example, Sambrook et al., Molecular Cloning, Second Edition, Current Protocols in Molecular Biology (1989). From the thus obtained DNA, a DNA encoding a human CD179b protein or a partial peptide thereof can be obtained.

The above-described host cells may be any cells as long as they can express the above polypeptide, and examples of prokaryotic cells include, but are not limited to, E. coli, and examples of eukaryotic cells include, but are not limited to, mammalian cultured cells such as the monkey kidney cells COS 1, Chinese hamster ovary cells CHO, human fetal kidney cell line HEK 293 and mouse embryonic skin cell line NIH3T3; yeast cells such as budding yeasts and fission yeasts; silkworm cells; and Xenopus egg cells.

In cases where prokaryotic cells are used as the host cells, the expression vector employed in the prokaryotic cells has a replication origin, promoter, ribosome binding site, multicloning site, terminator, drug resistant gene, nutrient complementary gene and/or the like. Examples of the expression vector for *E. coli* include the pUC system, pBluescriptII, pET expression system and pGEX expression system. By incorporating a DNA encoding the above polypeptide into such an expression vector and transforming prokaryotic host cells with the vector, followed by culturing the resulting transformants, the polypeptide encoded by the DNA can be expressed in the prokaryotic host cells. In this process, the polypeptide can also be expressed as a fusion protein with another protein (e.g., green fluorescent protein (GFP) or glutathione S-transferase (GST)).

In cases where eukaryotic cells are used as the host cells, an expression vector for eukaryotic cells having a promoter, splicing site, poly(A) addition site and/or the like is used as the expression vector. Examples of such an expression vector include pKA1, pCDM8, pSVK3, pMSG, pSVL, pBK-CMV, pBK-RSV, EBV vector, pRS, pcDNA3, pMSG and pYES2. In the same manner as described above, by incorporating a DNA encoding the above polypeptide into such an expression vector and transforming eukaryotic host cells with the vector, followed by culturing the resulting transformants, the polypeptide encoded by the DNA can be expressed in the eukaryotic host cells. In cases where pIND/V5-His, pFLAG-CMV-2, pEGFP-N1, pEGFP-C1 or the like is used as the expression vector, the above polypeptide can be expressed as a fusion protein to which a tag such as His tag (e.g., $(His)_6$ to $(His)_{10}$), FLAG tag, myc tag, HA tag or GFP was added.

For the introduction of the expression vector into the host cells, well-known methods such as electroporation, the calcium phosphate method, the liposome method, the DEAE dextran method and microinjection can be used.

Isolation and purification of the polypeptide of interest from the host cells can be carried out by a combination of known separation operations. Examples of the known separation operations include, but are not limited to, treatment with a denaturant such as urea, or a surfactant; ultrasonication treatment; enzyme digestion; salting-out or solvent fractional precipitation; dialysis; centrifugation; ultrafiltration; gel filtration; SDS-PAGE; isoelectric focusing; ion-exchange chromatography; hydrophobic chromatography; affinity chromatography; and reversed-phase chromatography.

<The Structure of an Antibody>

An antibody is usually a heteropolymeric glycoprotein having at least two heavy chains and two light chains. Except for IgM, it is a heterotetrameric glycoprotein of about 150 kDa constituted by two identical light (L) chains and two identical heavy (H) chains. Typically, each light chain is linked to a heavy chain via a single disulfide covalent bond, but the number of disulfide bonds between the heavy chains varies among various immunoglobulin isotypes. Each of the heavy chains and the light chains also has intrachain disulfide bonds. Each heavy chain has a variable domain (VH region) in its one end, and the variable domain is followed by several constant regions. Each light chain has a variable domain (VL region), and has one constant region at the opposite end thereof. The constant region of each light chain is aligned with the first constant region of a heavy chain, and each light chain variable domain is aligned with a heavy chain variable domain. Each variable domain of an antibody has particular regions showing particular variabilities, called the complementarity-determining regions (CDRs), which give a binding specificity to the antibody. Parts in each variable region, which parts are relatively conserved are called the framework regions (FRs). Each of the complete variable domains of the heavy chains and the light chains has four FRs linked via three CDRs. In each heavy chain, the three CDRs are called CDRH1, CDRH2 and CDRH3 in the order from the N-terminus, and, in each light chain, they are called CDRL1, CDRL2 and CDRL3 in a similar manner. For the binding specificity of an antibody against an antigen, CDRH3 is most important. Further, the CDRs in each strand are held together by the FR regions such that the CDRs are close to one another, thereby contributing to formation of an antigen-binding site together with the CDRs from another strand. Although the constant region does not directly contribute to binding of the antibody to an antigen, it shows various effector functions such as involvement in antibody-dependent cell-mediated cytotoxicity (ADCC), phagocytosis via binding to the Fcγ receptor, the half life/clearance rate via the Neonatal Fc receptor (FcRn), and complement-dependent cytotoxicity (CDC) via the C1q component of the complement cascade.

<Preparation of the Antibody>

The anti-CD179b antibody in the present invention means an antibody having an immunological reactivity with the total length of the CD179b protein or a fragment thereof. Here, the term "immunological reactivity" means a property by which the antibody and a CD179b antigen are bound to each other, and the function to damage (to cause death, suppression or regression of) tumors is exerted by such binding. That is, the type of the antibody used in the present invention is not restricted as long as the antibody can be bound to a CD179b protein to damage tumors such as breast cancer, leukemia, and lymphoma.

Examples of the antibody include monoclonal antibodies, polyclonal antibodies, synthetic antibodies, multispecific antibodies, human antibodies, humanized antibodies, chimeric antibodies, single chain antibodies, and antibody fragments (e.g., Fab and $(Aab')_2$). Further, the antibody belongs to an arbitrary class of an immunoglobulin molecule, such as IgG, IgE, IgM, IgA, IgD or IgY, or to an arbitrary subclass such as IgG1, IgG2, IgG3, IgG4, IgA1 or IgA2.

The antibody may be further modified by glycosylation, acetylation, formylation, amidation, phosphorylation, pegylation (PEG) and/or the like.

Preparation examples of various antibodies are described below.

In cases where the antibody is a monoclonal antibody, for example, a leukemia cell line Namalwa expressing CD179b is administered to a mouse to immunize the mouse, and spleen is extracted from the mouse. Cells are separated and fused with mouse myeloma cells, and, from the obtained fused cells (hybridomas), a clone producing an antibody having a cancer cell growth suppressing action is selected. By isolating the monoclonal antibody-producing hybridoma having a cancer cell growth suppressing action, and culturing the hybridoma, followed by purifying the antibody from the culture supernatant by a commonly-used affinity purification method, the antibody can be prepared.

A hybridoma which produces a monoclonal antibody can also be prepared, for example, as follows.

First, according to a known method, an animal is immunized with a sensitizing antigen. In general, the method is carried out by intraperitoneal or subcutaneous injection of the sensitizing antigen to a mammal. More particularly, the sensitizing antigen is diluted to an appropriate volume with PBS (Phosphate-Buffered Saline) or physiological saline and suspended, followed by mixing, as desired, an appropriate amount of a normal adjuvant such as Freund's complete adjuvant with the suspension. This is followed by emulsification, and then administration of the emulsion to a mammal every 4 to 21 days for several times. Further, it is also possible to use an appropriate carrier when the immunization with the sensitizing antigen is carried out.

After such immunization of a mammal and confirmation of increase in the serum level of the desired antibody, immunocytes are collected from the mammal and subjected to cell fusion. Examples of preferred immunocytes especially include spleen cells.

As the other parent cells to be fused with the immunocytes, mammalian myeloma cells are used. Examples of the myeloma cells preferably employed include various known cell lines such as P3U1 (P3-X63Ag8U1), P3 (P3x63Ag8.653) (J. Immnol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (deSt. Groth, S. F. et al., J. Immunol. Methods (1980) 35, 1-21), S194 (Trowbridge, I. S. J. Exp. Med. (1978) 148, 313-323) and R210 (Galfre, G. et al., Nature (1979) 277, 131-133).

The cell fusion between the immunocytes and the myeloma cells can be carried out basically according to a known method, for example, a method by Kohler and Milstein (Kohler. G. and Milstein, C., Methods Enzymol. (1981) 73, 3-46).

More particularly, the cell fusion is carried out, for example, in the presence of a cell fusion-promoting agent, in a normal nutrient medium. Examples of the fusion-promoting agent include polyethylene glycol (PEG) and Sendai virus (HVJ), and, in order to enhance the fusion efficiency, an auxiliary agent such as dimethylsulfoxide may also be added as desired.

The ratio between the immunocytes and the myeloma cells to be used may be arbitrarily set. For example, it is preferred to use 1 to 10 times more immunocytes than the myeloma cells. Examples of the medium which can be used for the cell fusion include the RPMI1640 medium which is preferred for the growth of the myeloma cell line; MEM medium; and other media normally used for this kind of cell culture. Further, a serum replacement such as fetal calf serum (FCS) can also be used in combination.

During the cell fusion, prescribed amounts of the immunocytes and the myeloma cells are mixed together well in the medium, and a PEG solution (with an average molecular weight of about 1000 to 6000, for example) preheated to about 37° C. is added to a concentration of normally 30 to 60% (w/v), followed by mixing the resulting mixture to form the hybridoma of interest. Subsequently, by repeating the operation of successive addition of an appropriate medium and removal of the supernatant by centrifugation, cell fusion agents and the like which are not preferred for the growth of the hybridoma are removed.

The thus obtained hybridoma is selected by being cultured in a normal selection medium such as the HAT medium (a medium containing hypoxanthine, aminopterin and thymidine). The culture in the above HAT medium is continued for a length of time sufficient for the cells other than the hybridoma of interest (unfused cells) to die (normally, for several days to several weeks). Thereafter, a normal limiting dilution method is carried out for screening and cloning of a single hybridoma producing the antibody of interest.

In addition to the method in which the above hybridoma is obtained by immunizing a non-human animal with the antibody, there is also a method in which human lymphocytes, such as human lymphocytes infected with EB virus, are sensitized in vitro with a protein, protein-expressing cells or a lysate thereof, and the sensitized lymphocytes are fused with human-derived myeloma cells having a permanent division potential, for example, U266 (registration number TIB196), to obtain a hybridoma producing a human antibody having a desired activity (cell growth suppression activity, for example).

The thus prepared hybridoma producing a monoclonal antibody can be subcultured in a normal medium, and can be stored in liquid nitrogen for a long period.

That is, the hybridoma can be prepared by a process wherein the desired antigen or cells expressing the desired antigen is/are used as a sensitizing antigen to carry out immunization according a conventional immunization method, thereby obtaining immunocytes, which are then fused with known parent cells by a conventional cell fusion method, followed by screening of monoclonal antibody-producing cells (hybridomas) by a conventional screening method.

Another example of the antibody which can be used in the present invention is a polyclonal antibody. The polyclonal antibody can be obtained, for example, as follows.

A naturally occurring CD179b protein, or a recombinant CD179b protein expressed as a fusion protein with GST in a microorganism such as *E. coli*, or a partial peptide thereof is used for immunization of a small animal such as a mouse, human antibody-producing mouse or rabbit, and serum is obtained from the small animal. A polyclonal antibody is prepared by purifying the serum by, for example, ammonium sulfate precipitation, protein A and protein G columns, DEAE ion-exchange chromatography, or an affinity column coupled with a CD179b protein or a synthetic peptide.

Here, known examples of the human antibody-producing mouse include the KM mouse (Kirin Pharma/Medarex) and XENOMOUSE™ (AMGEN™,SM). When such a mouse is immunized with a CD179b protein or a fragment thereof, a complete human polyclonal antibody can be obtained from blood. Further, by removing spleen cells from the immunized mouse and subjecting the cells to the fusion method with myeloma cells, a human-type monoclonal antibody can be prepared.

The antigen can be prepared according to a method using animal cells (Japanese Translated PCT Patent Application Laid-open No. 2007-530068), a method using a baculovirus (e.g., WO98/46777), or the like. In cases where the immunogenicity of the antigen is low, the immunization may be carried out after binding the antigen to a macromolecule having immunogenicity, such as albumin.

Further, a gene recombinant antibody can also be used, which antibody was prepared by cloning the antibody gene from the hybridoma and incorporating it into an appropriate vector, which was then transfected to a host, followed by allowing the host to produce the antibody by the genetic recombination technique (for example, see Carl, A. K. Borrebaeck, James, W. Larrick, THERAPEUTIC MONOCLONAL ANTIBODIES, Published in the United Kingdom by MACMILLAN PUBLISHERS LTD, 1990).

More particularly, cDNA of the variable region (V region) of the antibody is synthesized from mRNA of the hybridoma using a reverse transcriptase. After obtaining the DNA encoding the V region of the antibody of interest, the DNA is linked to DNA encoding the antibody constant region (C region) of interest, and the resultant is incorporated into an expression vector. Alternatively, the DNA encoding the V region of the antibody may be incorporated into an expression vector having the DNA of the antibody C region. The incorporation is carried out such that the expression is allowed under the controls by expression control regions such as an enhancer and/or a promoter. Subsequently, host cells can be transformed with this expression vector to allow expression of the antibody.

The anti-CD179b antibody of the present invention is preferably a monoclonal antibody. However, it may also be a polyclonal antibody, genetically modified antibody (such as a chimeric antibody or humanized antibody) or the like.

Examples of the monoclonal antibody include human monoclonal antibodies and non-human animal monoclonal antibodies (e.g., mouse monoclonal antibodies, rat monoclonal antibodies and chicken monoclonal antibodies). The monoclonal antibody can be prepared by culturing a hybridoma obtained by fusion of spleen cells from a non-human mammal (e.g., mouse or human antibody-producing mouse) immunized with a CD179b protein, with myeloma cells. In Examples below, a mouse monoclonal antibody #8 was prepared, with which an anti-tumor effect was confirmed. The antibody #8 has a heavy chain variable (VH) region having the amino acid sequence shown in SEQ ID NO:105 and a light chain variable region (VL) having the amino acid sequence shown in SEQ ID NO:109. Here, the VH region has the amino acid sequences shown in SEQ ID NO:103 (CDR1), SEQ ID NO:104 (CDR2) and SEQ ID NO:102 (CDR3); and the VL region has the amino acid sequences shown in SEQ ID NO:106 (CDR1), SEQ ID NO:107 (CDR2) and SEQ ID NO:108 (CDR3).

A chimeric antibody is an antibody prepared by combining sequences derived from different animals. Examples thereof include an antibody having variable regions of the heavy chain and the light chain of a mouse antibody and the constant regions of the heavy chain and the light chain of a human antibody. Preparation of the chimeric antibody can be carried out using a known method. For example, it can be obtained by linking a DNA encoding an antibody V region to a DNA encoding a human antibody C region, followed by incorporating the resultant to an expression vector and transfecting the vector to a host, thereby allowing production of a chimeric antibody.

Examples of the Polyclonal Antibody Include Antibodies Obtained by Immunizing a Human Antibody-Producing Animal (Mouse, for Example) with a CD179b Protein A humanized antibody is a modified antibody also called as a reshaped human antibody. A humanized antibody can be constructed by transplantation of the CDRs of an antibody derived from an immunized animal to the complementarity-determining regions of a human antibody. A common genetic recombination technique therefor is known.

More particularly, a DNA sequence designed such that the CDRs of a mouse antibody are linked to the framework regions (FRs) of a human antibody is synthesized by the PCR method from several oligonucleotides prepared such that the oligonucleotides have overlapped regions in their ends. The obtained DNA is linked to a DNA encoding the human antibody constant region, and the resultant is incorporated into an expression vector, followed by introducing the vector to a host, to obtain a humanized antibody (see European Patent Application Publication No. EP 239400 and International Patent Application Publication No. WO96/02576). The FRs of the human antibody linked via the CDRs are selected such that the complementarity-determining regions form a good antigen-binding site. As required, amino acids in the framework regions in the variable regions of the antibody may be substituted such that the complementarity-determining regions of the reshaped human antibody form an appropriate antigen-binding site (Sato, K. et al., Cancer Res. (1993) 53, 851-856). Further, the framework regions may be substituted with framework regions derived from various human antibodies (see International Patent Application Publication No. WO99/51743).

After preparation of a chimeric antibody or a humanized antibody, amino acids in the variable regions (FRs, for example) and/or the constant regions may be substituted with other amino acids.

The number of the amino acids to be substituted is, for example, less than 15, less than 10, not more than 8, not more than 7, not more than 6, not more than 5, not more than 4, not more than 3 or not more than 2, preferably 1 to 5, more preferably 1 or 2, and the substituted antibody should be functionally equivalent to the unsubstituted antibody. The substitutions are preferably conservative amino acid substitutions, which are substitutions among amino acids having similar properties of charges, side chains, polarities, aromaticities and/or the like. The amino acids having similar properties can be classified, for example, into basic amino acids (arginine, lysine and histidine), acidic amino acids (aspartic acid and glutamic acid), uncharged polar amino acids (glycine, asparagine, glutamine, serine, threonine, cysteine and tyrosine), nonpolar amino acids (leucine, isoleucine, alanine, valine, proline, phenylalanine, tryptophan and methionine), branched chain amino acids (threonine, valine and isoleucine) and aromatic amino acids (phenylalanine, tyrosine, tryptophan and histidine).

Examples of the modified antibody include antibodies bound to various molecules such as polyethylene glycol (PEG). In the modified antibody of the present invention, the substance to which the antibody is bound is not restricted. Such a modified antibody can be obtained by chemical modification of the obtained antibody. These methods are already established in the art.

Here, the term "functionally equivalent" means, for example, that the subject antibody has a similar biological or biochemical activity, more particularly, a function to damage tumors, and does not essentially cause the rejection reaction when it is applied to human. Examples of such an activity may include a cell growth suppressing activity and a binding activity.

As a method well-known to those skilled in the art for preparation of a polypeptide functionally equivalent to a certain polypeptide, introduction of a mutation(s) to a polypeptide is known. For example, those skilled in the art can use site-directed mutagenesis (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, TA (1985) Proc Natl Acad Sci USA. 82, 488-492; Kunkel (1988) Methods Enzymol. 85, 2763-2766) or the like to introduce, as appropriate, a mutation(s) to the antibody of the present invention, to prepare an antibody functionally equivalent to this antibody.

The antibody which recognizes the epitope of the CD179b protein to be recognized by the above-described anti-CD179b antibody can be obtained by a method known to those skilled in the art. Examples of the method by which it can be obtained include a method wherein the epitope of the CD179b protein recognized by the anti-CD179b antibody is determined by a normal method (e.g., epitope mapping) and an antibody is prepared using as an immunogen a polypeptide having an amino acid sequence included in the epitope; and a method wherein the epitope of the antibody is determined by a normal method, followed by selecting an antibody having the same epitope as that of the anti-CD179b antibody. Here, the term "epitope" means a polypeptide fragment having antigenicity or immunogenicity in a mammal, preferably human, and its minimum unit has about 7 to 12 amino acids.

The affinity constant Ka ($K_{on}/K_{off}$) of the antibody of the present invention is preferably at least $10^7$ M$^{-1}$, at least $10^8$ M$^{-1}$, at least $5 \times 10^8$ M$^{-1}$, at least $10^9$ M$^{-1}$, at least $5 \times 10^9$ M$^{-1}$, at least $10^{10}$ M$^{-1}$, at least $5 \times 10^{10}$ M$^{-1}$, at least $10^{11}$ M$^{-1}$, at least $5 \times 10^{11}$ M$^{-1}$, at least $10^{12}$ M$^{-1}$, at least $10^{13}$ M$^{-1}$.

The antibody of the present invention can be conjugated with an antitumor agent. The binding between the antibody and the antitumor agent can be carried out via a spacer having a group (e.g., succinimidyl group, formyl group, 2-pyridyldithio group, maleimidyl group, alkoxycarbonyl group or hydroxy group) reactive with an amino group, carboxyl group, hydroxy group, thiol group and/or the like.

Examples of the antitumor agent include the following antitumor agents known in literatures and the like, that is, paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethiylenethiophosphoramide, trimethylolomelamine, bullatacin, bullatacinone, camptothecin, bryostatin, callystatin, cryptophycin 1, cryptophycin 8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxyhydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, carminomycin, carzinophilin, chromomycin, dactinomycin, detorbicin, 6-diazo-5-oxo-L-norleucine, ADRIAMYCIN™, epirubicin, esorubicin, idarubicin, marcellomycin, mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine and floxuridine; androgens such as calusterone, dromostanolone propionate, epitiostanol, mepitiostane, testolactone, aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, epothilone, etoglucid, lentinan, lonidamine, maytansine, ansamitocine, mitoguazone, mitoxantrone, mopidanmol, nitraerine, pentostatin, phenamet, pirarubicin, losoxantrone, podophyllinic acid, 2-ethylhydrazide, procarbazine, razoxane, rhizoxin, schizophyllan, spirogermanium, tenuazonic acid, triaziquone, roridine A, anguidine, urethane, vindesine, dacarbazine, mannomustine, mitobronitol, mitolactol, pipobroman, gacytosine, doxetaxel, chlorambucil, gemcitabine, 6-thioguanine, mercaptopurine, cisplatin, oxaliplatin, carboplatin, vinblastine, etoposide, ifosfamide, mitoxantrone, vincristine, vinorelbine, novantrone, teniposide, edatrexate, daunomycin, aminopterin, xeloda, ibandronate, irinotecan, topoisomerase inhibitors, difluoromethylornithine (DMFO), retinoic acid and capecitabine, and pharmaceutically acceptable salts and derivatives thereof.

Alternatively, the antibody of the present invention can be linked to a known radioisotope described in a literature or the like, such as At$^{211}$, I$^{131}$, I$^{125}$, Y$^{90}$, Re$^{186}$, Re$^{188}$, Sm$^{153}$, Bi$^{212}$, P$^{32}$ or Lu. The radioisotope is preferably effective for therapy and/or diagnosis of a tumor.

The antibody of the present invention is an antibody having an immunological reactivity with CD179b, or an antibody which specifically recognizes CD179b. The antibody should be an antibody having a structure by which the rejection reaction can be mostly or completely avoided in the subject animal to which the antibody was administered. Examples of such an antibody include, for example, in cases where the subject animal is human, human antibodies, humanized antibodies, chimeric antibodies (e.g., human-mouse chimeric antibodies), single chain antibodies and bispecific antibodies. Each of these antibodies is a recombinant antibody wherein: each variable region in the heavy chain and the light chain is derived from a human antibody; each variable region in the heavy chain and the light chain is constituted by the complementarity-determining regions (CDR1, CDR2 and CDR3) of an antibody derived from a non-human animal and the framework regions derived from a human antibody; or each variable region in the heavy chain and the light chain is derived from a non-human animal; which recombinant antibody has human antibody-derived constant regions in the heavy chain and the light chain. The first two antibodies are preferred.

These recombinant antibodies can be prepared as follows. A DNA encoding a monoclonal antibody (for example, human monoclonal antibody, mouse monoclonal antibody, rat monoclonal antibody or chicken monoclonal antibody) against human CD179b is cloned from antibody-producing cells such as hybridomas, and, using this as a template, DNAs encoding the light chain variable region and the heavy chain variable region of the antibody is prepared by, for example, the RT-PCR method, followed by determining the sequence of the variable region or the sequences of CDR1, CDR2 and CDR3 in each of the light chain and the heavy chain according to the Kabat EU numbering system (Kabat et al., Sequences of Proteins of Immunological Interest, 5Th Ed. Public Health Service, National Institute of Health, Bethesda, Md. (1991)). Further, DNAs encoding the respective variable regions or DNAs encoding the respective CDRs are prepared using the genetic recombination technique (Sambrook et al., Molecular Cloning, Second Edition, Current Protocols in Molecular Biology (1989)) or a DNA synthesizer. Here, the above-described human monoclonal antibody-producing hybridoma can be prepared by immunizing a human antibody-producing animal (e.g., mouse) with human CD179b, followed by fusing spleen cells excised from the immunized animal with myeloma cells. In addition, as required, DNAs encoding the variable region and the constant region in the light chain or the heavy chain derived from a human antibody are prepared using the genetic recombination technique or a DNA synthesizer.

In the case of a humanized antibody, a DNA encoding the humanized antibody can be prepared by a process wherein the CDR sequences in a DNA encoding the variable region of the light chain or the heavy chain derived from a human antibody are substituted with the corresponding CDR sequences of an antibody derived from a non-human animal (e.g., mouse, rat or chicken) to prepare a DNA, and the thus obtained DNA is linked to a DNA encoding the constant region in the light chain or the heavy chain, respectively, derived from a human antibody.

In the case of a chimeric antibody, a DNA encoding the chimeric antibody can be prepared by a process wherein a DNA encoding the variable region in the light chain or the heavy chain derived from a non-human animal (e.g., mouse, rat or chicken) is linked to a DNA encoding the constant region of the light chain or the heavy chain, respectively, derived from a human antibody In the case of a single-chain antibody, which is an antibody having a heavy chain variable region and a light chain variable region linearly linked to each other via a linker, a DNA encoding the single-chain antibody can be prepared by a process wherein a DNA encoding the heavy chain variable region, a DNA encoding the linker and a DNA encoding the light chain variable region are linked together. Here, each of the heavy chain variable region and the light chain variable region is either derived from a human antibody or derived from a human antibody in which only the CDRs were replaced by the CDRs of an antibody derived from a non-human animal (e.g., mouse, rat or chicken). Further, the linker has 12 to 19 amino acids, and examples thereof include $(G_4S)_3$ having 15 amino acids (Kim, G B. et al., Protein Engineering Design and Selection 2007, 20(9):425-432).

In the case of a bispecific antibody (diabody), which is an antibody capable of binding specifically to two different epitopes, a DNA encoding the bispecific antibody can be prepared, for example, by a process wherein a DNA encoding a heavy chain variable region A, a DNA encoding a light chain variable region B, a DNA encoding a heavy chain variable region B and a DNA encoding a light chain variable region A are linked together in this order (however, the DNA encoding a light chain variable region B and the DNA encoding a heavy chain variable region B are linked to each other via a DNA encoding a linker as described above). Here, each of the heavy chain variable region and the light chain variable region is either derived from a human antibody or derived from a human antibody in which only the CDRs were replaced by the CDRs of an antibody derived from a non-human animal (e.g., mouse, rat or chicken).

A recombinant antibody can be prepared by incorporating the thus prepared recombinant DNA(s) into one or more appropriate vector(s) and introducing the resulting vector(s) into host cells (e.g., mammalian cells, yeast cells and insect cells), followed by allowing (co-)expression of the recombinant DNA(s) (P. J. Delves, ANTIBODY PRODUCTION ESSENTIAL TECHNIQUES, 1997 WILEY; P. Shepherd and C. Dean, Monoclonal Antibodies, 2000 OXFORD UNIVERSITY PRESS; J. W. Goding, Monoclonal Antibodies: principles and practice, 1993 ACADEMIC PRESS).

The antibody of the present invention prepared by the above method is an antibody comprising, for example, a heavy chain variable region having the amino acid sequences shown in SEQ ID NOs:103, 104 and 102 and a light chain variable region having the amino acid sequences shown in SEQ ID NOs:106, 107 and 108. Here, the amino acid sequences shown in SEQ ID NOs:103, 104 and 102 are those for CDR1, CDR2 and CDR3, respectively, of a mouse antibody heavy chain variable region, and the amino acid sequences shown in SEQ ID NOs:106, 107 and 108 are those for CDR1, CDR2 and CDR3, respectively, of a mouse antibody light chain variable region. Therefore, the humanized antibody, chimeric antibody, single-chain antibody or bispecific antibody of the present invention is the following antibody, for example.

(i) An antibody comprising: a heavy chain variable region having the amino acid sequences shown in SEQ ID NOs: 103, 104 and 102 and the amino acid sequences of the framework regions derived from a human antibody; and a light chain variable region having the amino acid sequences shown in SEQ ID NOs:106, 107 and 108 and the amino acid sequences of the framework regions derived from a human antibody.

(ii) An antibody comprising: a heavy chain variable region having the amino acid sequences shown in SEQ ID NOs:103, 104 and 102 and the amino acid sequences of the framework regions derived from a human antibody; a heavy chain constant region having an amino acid sequence derived from a human antibody; a light chain variable region having the amino acid sequences shown in SEQ ID NOs: 106, 107 and 108 and the amino acid sequences of the framework regions derived from a human antibody; and a light chain constant region having an amino acid sequence derived from a human antibody.

(iii) An antibody comprising: a heavy chain variable region having the amino acid sequence shown in SEQ ID NO:105; and a light chain variable region having the amino acid sequence shown in SEQ ID NO: 109.

(iv) An antibody comprising: a heavy chain variable region having the amino acid sequence shown in SEQ ID NO:105; a heavy chain constant region having an amino acid sequence derived from a human antibody; a light chain variable region having the amino acid sequence shown in SEQ ID NO:109; and a light chain constant region having an amino acid sequence derived from a human antibody.

Sequences of the constant regions and the variable regions of human antibody heavy chains and light chains can be obtained from, for example, NCBI (USA: GENBANK$^{SM}$, UNIGENE and the like). Examples of the sequences which may be referred to include the accession number J00228 for the human IgG1 heavy chain constant region, the accession number J00230 for the human IgG2 heavy chain constant region, the accession number X03604 for the human IgG3 heavy chain constant region, the accession number K01316 for the human IgG4 heavy chain constant region, the accession numbers V00557, X64135, X64133 and the like for the human light chain κconstant region, and the accession numbers X64132, X64134 and the like for the human light chain λ constant region.

The above antibody preferably has cytotoxic activity and therefore can exert an anti-tumor effect.

Further, the specific sequences of the variable regions of the heavy chain and the light chain and the CDRs in the above antibodies are presented for the illustration purpose only, and it is apparent that they are not restricted to the specific sequences. A hybridoma which can produce another human antibody or non-human animal antibody (e.g., mouse antibody) against human CD179b is prepared, and the monoclonal antibody produced by the hybridoma is recovered, followed by judging whether or not it is an antibody of interest using as indices its immunological affinity and cytotoxicity to human CD179b. By this, a monoclonal antibody-producing hybridoma of interest is identified, and DNAs encoding the variable regions of the heavy chain and the light chain of the antibody of interest are prepared from the hybridoma as described above, followed by determining the sequences of the DNAs and then using the DNAs for preparation of the another antibody.

Further, the above antibody of the present invention may have substitution, deletion and/or addition of 1 or several (preferably, 1 or 2) amino acid(s) especially in a framework region sequence(s) and/or constant region sequence(s) in each of the antibodies (i) to (iv) above, as long as the antibody has a specificity allowing specific recognition of CD179b. Here, the term "several" means 2 to 5, preferably 2 or 3.

The present invention further provides a DNA encoding the above antibody of the present invention, a DNA encoding the heavy chain or the light chain of the above antibody or a DNA encoding the variable region of the heavy chain or the light chain of the above antibody. Examples of such a DNA include: DNAs encoding heavy chain variable regions having the base sequences encoding the amino acid sequences shown in SEQ ID NOs:103, 104 and 102; DNAs encoding light chain variable regions having the base sequences encoding the amino acid sequences shown in SEQ ID NOs:106, 107 and 108; and the like.

Since the complementarity-determining regions (CDRs) encoded by DNAs having these sequences are regions which determine the specificity of the antibody, the sequences encoding the other regions in the antibody (that is, the constant regions and the framework regions) may be those derived from another antibody. Here, although the another antibody includes antibodies derived from non-human organisms, it is preferably derived from human in view of reduction of side effects. That is, in the above-described DNA, the regions encoding the respective framework regions and the constant regions of the heavy chain and the light chain preferably have base sequences encoding corresponding amino acid sequences derived from a human antibody.

Other examples of the DNA encoding the antibody of the present invention include DNAs encoding the heavy chain variable region having a base sequence encoding the amino acid sequence shown in SEQ ID NO:105 and DNAs wherein the region encoding the light chain variable region has a base sequence encoding the amino acid sequence shown in SEQ ID NO:109. Here, examples of the base sequence encoding the amino acid sequence shown in SEQ ID NO:105 include the base sequence shown in SEQ ID NO:110. Further, examples of the base sequence encoding the amino acid sequence shown in SEQ ID NO: 109 include the base sequence shown in SEQ ID NO:111. Among these DNAs, preferred are those comprising the region encoding the constant region of each of the heavy chain and the light chain, having a base sequence encoding a corresponding amino acid sequence derived from a human antibody.

The DNA of the present invention can be obtained by, for example, the above method or the following method. First, from a hybridoma related to the antibody of the present invention, total RNA is prepared using a commercially available RNA extraction kit, and cDNA is synthesized by a reverse transcriptase using random primers or the like. Subsequently, by the PCR method using as primers oligonucleotides having sequences conserved in the variable region of each of a known mouse antibody heavy chain gene and light chain gene, cDNAs encoding the antibody are amplified. The sequence encoding each constant region can be obtained by amplifying a known sequence by the PCR method. The base sequences of the DNAs can be determined by a conventional method by, for example, incorporating the sequences into plasmids or phages for sequence determination.

The anti-tumor effect of the anti-CD179b antibody used in the present invention against CD179b-expressing cancer cells is considered to be caused by the following mechanism.

The antibody-dependent cell-mediated cytotoxicity (ADCC) by effector cells against CD179b-expressing cells; and the complement-dependent cytotoxicity (CDC) against CD179b-expressing cells.

Thus, evaluation of the activity of the anti-CD179b antibody used in the present invention can be carried out, as particularly shown in Examples below, by measuring the above-described ADCC activity or CDC activity against cancer cells expressing CD179b in vitro.

Since the anti-CD179b antibody used in the present invention binds to a CD179b protein on cancer cells and exhibits an anti-tumor action due to the above activities, the antibody is considered to be effective for therapy and/or prophylaxis of cancer. That is, the present invention provides a pharmaceutical composition for therapy and/or prophylaxis of cancer comprising as an effective component an anti-CD179b antibody. In cases where the anti-CD179b antibody is used for the purpose of administration to a human body (antibody therapy), the antibody is preferably prepared as a human antibody or a humanized antibody in order to reduce its immunogenicity.

A higher binding affinity of the anti-CD179b antibody to the CD179b protein on the cancer cell surface causes a stronger anti-tumor activity by the anti-CD179b antibody. Thus, if an anti-CD179b antibody having a higher binding affinity to the CD179b protein can be obtained, a higher anti-tumor effect can be expected, and therefore the antibody can be applied as a pharmaceutical composition for the purpose of therapy and/or prophylaxis of cancer. In terms of the higher binding affinity, the affinity constant Ka ($K_{on}/K_{off}$) is preferably at least $10^7$ $M^{-1}$, at least $10^8$ $M^{-1}$, at least $5 \times 10^8$ $M^{-1}$, at least $10^9$ $M^{-1}$, at least $5 \times 10^9$ $M^{-1}$, at least $10^{10}$ $M^{-1}$, at least $5 \times 10^{10}$ $M^{-1}$, at least $10^{11}$ $M^{-1}$, at least $5 \times 10^{11}$ $M^{-1}$, at least $10^{12}$ $M^{-1}$, at least $10^{13}$ $M^{-1}$, as previously mentioned.

<Pharmaceutical Composition>

The target of the pharmaceutical composition of the present invention for therapy and/or prophylaxis of cancer is not restricted as long as it is a cancer (cell) expressing the CD179b gene, and preferably a cancer (cell) selected from the group consisting of leukemia, lymphoma and breast cancer, including also mammary gland cancer, combined mammary gland cancer, mammary gland malignant mixed tumor, intraductal papillary adenocarcinoma, mastocytoma, chronic lymphocytic leukemia, gastrointestinal lymphoma, digestive organ lymphoma and small/medium cell lymphoma.

Further, the antibody or a fragment thereof used in the present invention can be used for therapy and/or prophylaxis of the above-described cancers.

When the antibody used in the present invention is used as a pharmaceutical composition, it can be formulated by a method known to those skilled in the art. For example, it can be parenterally used in the form of an injection solution containing a sterile solution or suspension prepared with another pharmaceutically acceptable liquid. For example, the composition may be used in combination with a pharmaceutically acceptable carrier(s) and/or medium/media, such as sterile water, physiological saline, vegetable oil, emulsifier, suspending agent, surfactant, stabilizer, flavoring agent, excipient, vehicle, antiseptic and/or binder, which is/are mixed into the form of a unit dose required for carrying out formulation which is generally accepted. The amount of the effective component in the formulation is determined such that an appropriate volume is obtained within the prescribed range.

The sterile composition for injection can be prescribed using a vehicle such as distilled water for injection, according to a conventional formulation method.

Examples of the aqueous solution include isotonic solutions containing physiological saline, glucose and/or an adjunct(s) such as D-sorbitol, D-mannose, D-mannitol and/or sodium chloride, which may be used in combination with an appropriate solubilizer(s) such as an alcohol, in particular, ethanol; polyalcohol such as propylene glycol; polyethylene glycol; nonionic surfactant such as polysorbate 80 ™; and/or HCO-60.

Examples of the oily liquid include sesame oils and soybean oils, which may be used in combination with benzyl benzoate or benzyl alcohol as a solubilizer. Further, a buffering agent such as phosphate buffer or sodium acetate buffer; soothing agent such as procaine hydrochloride; and/or stabilizer such as benzyl alcohol, phenol or antioxidant may also be blended. The prepared injection solution is usually filled into an appropriate ampoule.

The administration is carried out orally or parenterally, preferably parenterally, and particular examples thereof include the injection solution type, nasal administration type, pulmonary administration type and percutaneous administration type. Examples of the injection solution type include intravenous injection, intramuscular injection, intraperitoneal administration and subcutaneous injection, by which the injection solution can be administered systemically or topically.

Further, the method of administration can be appropriately selected depending on the age, symptom, sex and the like of the patient. The dose of the pharmaceutical composition containing the antibody or a fragment thereof can be selected within the range of, for example, 0.0001 mg to 1000 mg per 1 kg of the body weight per one time. Alternatively, the dose can be selected within the range of 0.001 to 100000 mg/body per patient, but the dose is not restricted to these values. The dose and the method of administration vary depending on the body weight, age, symptom and the like of the patient, and those skilled in the art can appropriately select them.

<Polypeptide and DNA>

The present invention further provides the following polypeptides and DNAs related to the above antibody.

(i) A polypeptide having the amino acid sequence shown in SEQ ID NO:105, and a DNA encoding the polypeptide.

(ii) A polypeptide having the amino acid sequence shown in SEQ ID NO:109, and a DNA encoding the polypeptide.

(iii) A DNA having the base sequence shown in SEQ ID NO:110.

(iv) A DNA having the base sequence shown in SEQ ID NO:111.

(v) A heavy chain CDR polypeptide selected from the group consisting of the amino acid sequences shown in SEQ ID NOs:103, 104 and 102, and a DNA encoding the polypeptide.

(vi) A light chain CDR polypeptide selected from the group consisting of the amino acid sequences shown in SEQ ID NOs:106, 107 and 108, and a DNA encoding the polypeptide.

These polypeptides and DNAs may be prepared using the genetic recombination technique as described above.

EXAMPLES

The present invention will now be described concretely by way of Examples, but the scope of the present invention is not restricted by these particular examples.

Example 1: Identification of a Novel Cancer Antigen by the SEREX Method (1) Preparation of a cDNA Library From a canine mammary gland cancer tissue removed by surgery, total RNA was extracted by the Acid guanidium-Phenol-Chloroform method, and poly(A)$^+$ RNA was purified using the Oligotex-dT30 mRNA purification Kit (manufactured by Takara Shuzo Co., Ltd.) according to the protocol described in the attached instructions.

Using the thus obtained mRNA (5 µg), a canine mammary gland cancer-derived cDNA phage library was synthesized. For preparation of the cDNA phage library, cDNA Synthesis Kit, ZAP-cDNA Synthesis Kit and ZAP-cDNA GigapackIII Gold Cloning Kit (manufactured by STRATAGENE) were used according to the protocols described in the attached instructions. The size of the prepared cDNA phage library was $2.99 \times 10^5$ pfu/ml.

(2) Screening of the cDNA Library by Serum

Using the canine mammary gland cancer-derived cDNA phage library prepared as described above, immunoscreening was carried out. More particularly, host E. coli (XL1-Blue MRF') was infected with the library such that 2340 clones were included in Φ90×15 mm NZY agarose plate, followed by culture at 42° C. for 3 to 4 hours to allow formation of plaques. The plate was covered with a nitrocellulose membrane (HYBOND™ C Extra; manufactured by GE Healthcare Bio-Science) impregnated with IPTG (isopropyl-β-D-thiogalactoside) at 37° C. for 4 hours, to allow induction and expression of proteins, thereby transferring the proteins to the membrane. Thereafter, the membrane was recovered and soaked in TBS (10 mM Tris-HCl, 150 mM NaCl pH 7.5) supplemented with 0.5% non-fat dry milk, followed by being shaken at 4° C. overnight to suppress nonspecific reactions. This filter was allowed to react with 500-fold diluted patient dog serum at room temperature for 2 to 3 hours.

As the above-described patient dog serum, a total of 3 serum samples were used which were collected from each of the dog from which the above mammary gland cancer was removed and another mammary gland cancer patient dog. These sera were stored at −80° C. and pretreated immediately before use. The pretreatment of the sera was carried out by the following method. That is, host E. coli (XL1-BLue MRF') was infected with λ ZAP Express phage into which no exogenous gene was inserted, and cultured on a NZY plate at 37° C. overnight. Subsequently, 0.2 M NaHCO$_3$ buffer (pH 8.3) containing 0.5 M NaCl was added to the plate, and the plate was left to stand at 4° C. for 15 hours, followed by recovering the supernatant as an E. coli/phage extract. Thereafter, the recovered E. coli/phage extract was passed through a NHS-column (manufactured by GE Healthcare Bio-Science) to immobilize the proteins derived from the E. coli/phage. The serum from the patient dog was passed through this protein-immobilized column and allowed to react with the proteins, thereby removing antibodies that adsorb to E. coli and the phage from the serum. The serum fraction passed through the column without being adsorbed was 500-fold diluted with TBS supplemented with 0.5% non-fat dry milk, and the resulting dilution was used as a material for the immunoscreening.

The membrane to which the thus treated serum and the above-described fusion proteins were blotted was washed with TBS-T (0.05% Tween 20/TBS) 4 times, and a goat anti-dog IgG (Goat anti Dog IgG-h+l HRP conjugated; manufactured by BETHYL Laboratories, Inc.) which was 5000-fold diluted with TBS supplemented with 0.5% non-fat dry milk was allowed, as a secondary antibody, to react at room temperature for 1 hour. Detection was carried out by an enzymatic coloring reaction using the NBT/BCIP reaction solution (manufactured by Roche), and colonies whose positions were identical to those of positive sites of the coloring reaction were collected from the Φ90×15 mm NZY agarose plate, and dissolved into 500 µl of SM buffer (100 mM NaCl, 10 mM MgClSO₄, 50 mM Tris-HCl, 0.01% gelatin, pH7.5). The second and third screenings were carried out by repeating the same method as described above until the colonies positive in the coloring reaction became single colonies, thereby isolating 45 positive clones after screening of 92820 phage clones reactive with IgG in the serum.

Homology Search of the Isolated Antigen Genes

To subject the 45 positive clones isolated by the above method to sequence analysis, an operation to convert the phage vector to a plasmid vector was carried out. More particularly, 200 µl of a solution prepared such that the host E. coli (XL1-Blue MRF') was contained to an absorbance $OD_{600}$ of 1.0, 250 µl of the purified phage solution and 1 µl of ExAssist helper phage (manufactured by STRATAGENE) were mixed together, and the resulting mixture was allowed to react at 37° C. for 15 minutes, followed by adding 3 ml of LB broth thereto and culturing the resultant at 37° C. for 2.5 to 3 hours. This was immediately followed by 20 minutes of incubation in a water bath at 70° C. and centrifugation at 1000×g for 15 minutes, after which the supernatant was collected as a phagemid solution. Subsequently, 200 µl of a solution prepared such that the phagemid host E. coli (SOLR) was contained to an absorbance $OD_{600}$ of 1.0 and 10 µl of the purified phagemid solution were mixed together, and the resulting mixture was allowed to react at 37° C. for 15 minutes, followed by plating a 50 µl aliquot of the resultant on LB agar medium supplemented with ampicillin (50 µg/ml final concentration) and culturing at 37° C. overnight. Single colonies of the transformed SOLR were picked up and cultured in LB medium supplemented with ampicillin (50 µg/ml final concentration) at 37° C., followed by purifying plasmid DNAs having inserts of interest using QIAGEN™ plasmid Miniprep Kit (manufactured by QIAGEN™).

Each purified plasmid was subjected to analysis of the full-length sequence of the insert by the primer walking method using the T3 primer shown in SEQ ID NO:94 and the T7 primer shown in SEQ ID NO:95. By this sequence analysis, the gene sequences shown in the even number IDs of SEQ ID NOs:4 to 92 were obtained. Using the base sequences and the amino acid sequences (odd number IDs of SEQ ID NOs: 5 to 93) of these genes, homology search against known genes were carried out using a homology search program BLAST (http://www.ncbi.nlm.nih.gov/BLAST/), and, as a result, it was revealed that all the obtained 45 genes were those encoding CD179b. The homologies among the 45 genes were 94 to 99% in terms of the base sequences and 96 to 99% in terms of the amino acid sequences. The homologies between these genes and the gene encoding a human homologous factor were 62 to 82% in terms of the base sequences and 69 to 80% in terms of the amino acid sequences, in the region translated to a protein. The base sequence of the human homologous factor is shown in SEQ ID NO:1, and the amino acid sequences of the human homologous factor are shown in SEQ ID NOs:2 and 3.

(4) Analysis of Gene Expression in Each Tissue

Expressions of the genes obtained by the above method in dog and human normal tissues and various cell lines were investigated by the RT-PCR (Reverse Transcription-PCR) method. The reverse transcription reaction was carried out as follows. That is, from 50 to 100 mg of each tissue or 5-10×10⁶ cells of each cell line, total RNA was extracted using the TRIZOL reagent (manufactured by INVITROGEN) according to the protocol described in the attached instructions. Using this total RNA, cDNA was synthesized by the Superscript First-Strand Synthesis System for RT-PCR (manufactured by INVITROGEN) according to the protocol described in the attached instructions. As the cDNAs of human normal tissues (brain, hippocampus, testis, colon and placenta), Gene Pool cDNA (manufactured by INVITROGEN), QUICK-Clone cDNA (manufactured by CLONETECH) and Large-Insert cDNA Library (manufactured by CLONETECH) were used. The PCR reaction was carried out as follows, using primers specific to the obtained dog genes (shown in SEQ ID NOs:96 and 97) and their human homologous gene (shown in SEQ ID NOs:98 and 99). That is, reagents and an attached buffer were mixed such that concentrations/amounts of 0.25 µl of a sample prepared by the reverse transcription reaction, 2 µM each of the above primers, 0.2 mM each of dNTPs, and 0.65 U ExTaq polymerase (manufactured by Takara Shuzo Co., Ltd.) were attained in a total volume of 25 µl, and the reaction was carried out by repeating 30 cycles of 94° C. for 30 seconds, 60° C. for 30 seconds and 72° C. for 30 seconds using a THERMAL CYCLER (manufactured by Bio-Rad Laboratories, Inc.). The above-described primers specific to genes having the base sequences shown in SEQ ID NOs: 96 and 97 were for amplification of the positions 32 to 341 in the base sequence shown in SEQ ID NO:4, and for amplification of the region common to all the dog CD179b genes shown in the even number IDs of SEQ ID NOs: 4 to 92. Further, the primers specific to genes having the base sequences shown in SEQ ID NOs:98 and 99 were for amplification of the positions 216 to 738 in the base sequence shown in SEQ ID NO:1. As a control for comparison, primers specific to GAPDH (shown in SEQ ID NOs:100 and 101) were used at the same time. As a result, as shown in FIG. 1, the obtained dog genes did not show expression in normal dog tissues at all, but showed strong expression in canine breast cancer tissues. In terms of expression of the human homologous gene, bone marrow was the only human normal tissue wherein its expression was confirmed, but, in human cancer cells, its expression was detected in leukemia cell lines and breast cancer cell lines, so that specific expression of CD179b in the leukemia cell lines and the breast cancer cell lines was confirmed.

In FIG. 1, reference numeral 1 in the ordinate represents the expression pattern of the gene identified as above, and reference numeral 2 represents the expression pattern of the GAPDH gene as the control for comparison.

(5) Analysis of Expression of the Antigen Protein on Cancer Cells

Subsequently, each cancer cell line wherein expression of the CD179b gene was confirmed was investigated for whether or not the CD179b protein is expressed on the cell surface. In a 1.5 ml microcentrifuge tube, 10⁶ cells of each human cancer cell line for which expression of the gene was observed were placed, which tube was then centrifuged. To this tube, 5 µl of mouse anti-human CD179b antibody (clone name: GA170; manufactured by Santa Cruz Biotechnology) was added, and the resultant was suspended in 95 µl of PBS supplemented with 0.1% fetal calf serum, followed by leaving the resulting suspension to stand on ice for 1 hour. After washing the cells with PBS, the cells were suspended in 5 µl of FITC-labeled rabbit anti-mouse IgG2a monoclonal antibody (manufactured by BD Pharmingen) and 95 µl of PBS supplemented with 0.1% fetal bovine serum, and left to stand on ice for 1 hour. After washing the cells with PBS, fluorescence intensity was measured by FACSCalibur manufactured by Beckton Dickinson. On the other hand, the same operation as described above was carried out to prepare the cells as a control, using mouse IgG2a Isotype control (manufactured by MBL) instead of the mouse anti-human CD179b antibody. As a result, the cells to which the anti-human CD179b antibody was added showed a fluorescence intensity not less than 10% higher than that of the control, and therefore it was confirmed that the CD179b protein is expressed on the cell membrane surface of the above human cancer cell line.

Example 2: Anti-Tumor Effect, Against Cancer Cells, of the Antibody Against CD179b (1) The ADCC Activity Thereafter, whether or not the antibody against CD179b can damage tumor cells expressing CD179b was studied. The evaluation was carried out using a commercially available mouse antibody against human CD179b (clone name: GA170). Into a 50 ml centrifuge tube, $10^6$ cells belonging to each of the 3 types of human leukemia cells, Namalwa, BDCM and RPMI1788 (all of these were purchased from ATCC), whose expression of CD179b was confirmed in Example 1(5), were collected, and 100 µCi of chromium 51 was added to the tube, followed by incubation at 37° C. for 2 hours. Thereafter, the cells were washed 3 times with RPMI medium supplemented with 10% fetal calf serum, and placed in a 96-well V-bottom plate in an amount of $10^3$ cells/well. To each well, 1 µg of GA170 was added, and $2 \times 10^5$ lymphocytes separated from mouse spleen were further added thereto, followed by culture under the conditions of 37° C., 5% $CO_2$ for 4 hours. Thereafter, the amount of chromium 51 in the culture supernatant released from damaged tumor cells was measured, and the ADCC activity by GA170 against each type of cancer cells was calculated. As a result, ADCC activities of 32.6%, 32.3% and 28.3% were confirmed for Namalwa, BDCM and RPMI1788, respectively. On the other hand, when an isotype control (clone name: 6H3) of GA170 was used for the same operation, the above activity was not detected. Thus, it was revealed that, by the ADCC activity induced using an antibody against CD179b, tumor cells expressing CD179b can be damaged.

The cytotoxic activity was obtained as a result of a process wherein the antibody against CD179b used in the present invention, mouse lymphocytes, and $10^3$ cells of each leukemia cell line were mixed together, followed by culturing the cells for 4 hours, measuring the amount of chromium 51 released into the medium after the culture, and calculating the cytotoxic activity against the leukemia cell line according to the following calculation equation*.

*Equation: Cytotoxic activity (%)=the amount of chromium 51 released from Namalwa, BDCM or RPMI1788 upon addition of the antibody against CD179b and mouse lymphocytes/the amount of chromium 51 released from the target cells upon addition of 1N hydrochloric acid×100.

(2) The CDC Activity

Blood collected from a rabbit was placed in an EPPENDORF TUBE™, and left to stand at room temperature for 60 minutes, followed by centrifugation at 3000 rpm for 5 minutes to prepare serum for measurement of the CDC activity. Into a 50 ml centrifuge tube, $10^6$ cells belonging to each of the 3 types of human leukemia cells, Namalwa, BDCM and RPMI1788 were collected, and 100 µCi of chromium 51 was added to the tube, followed by incubation at 37° C. for 2 hours and washing the cells 3 times with RPMI medium supplemented with 10% fetal calf serum. Thereafter, the cells were suspended in RPMI medium containing the rabbit serum prepared as above in an amount of 50%, and placed in a 96-well V-bottom plate in an amount of $10^3$ cells/well. To each well, 1 µg of GA170 was added, followed by culture under the conditions of 37° C., 5% $CO_2$ for 4 hours. Thereafter, the amount of chromium 51 in the culture supernatant released from damaged tumor cells was measured, and the CDC activity by GA170 against each cancer cells was calculated. As a result, CDC activities of 30.5%, 21.2% and 30.5% were confirmed for Namalwa, BDCM and RPMI1788, respectively. On the other hand, when an isotype control (clone name: 6H3) of GA170 was used for the same operation, the above activity was not detected. Thus, it was revealed that, by the CDC activity induced using an antibody against CD179b, tumor cells expressing CD179b can be damaged.

The cytotoxic activity was obtained, as in the above (1), as a result of calculation of the cytotoxic activity against each leukemia cell line according to the following calculation equation*.

*Equation: Cytotoxic activity (%)=the amount of chromium 51 released from Namalwa, BDCM or RPMI1788 upon addition of the antibody against CD179b, and rabbit serum/the amount of chromium 51 released from the target cells upon addition of 1N hydrochloric acid×100.

Example 3: Preparation of a Monoclonal Antibody (1) Preparation of an Antigen Protein The human CD179b protein was prepared by the method of lipofection to animal cells. The human CD179b gene (SEQ ID NO:22) was introduced to a vector encoding the human IgG1Fc region, the SRaIgG1Fc vector, via restriction sites XhoI and BamHI. The SRaIgG1Fc vector is a vector prepared by introduction of the gene for the human IgG1Fc region into the pcDL-SRa296 vector (manufactured by DNAX). Subsequently, 24 µg of the plasmid was mixed with 60 µl of LIPOFECTIN™ 2000 (manufactured by Invitrogen), and OPTI-MEM™ (manufactured by Invitrogen) was added to the resulting mixture to attain a total volume of 3 ml, followed by leaving the mixture to stand at room temperature for not less than 20 minutes. To CHO-K1 cells preliminarily prepared to $2 \times 10^6$ cells/12 ml OPTI-MEM™, 3 ml of the above-mentioned mixed solution of the plasmid was added, followed by 8 hours of culture under the conditions of 37° C. and 5% $CO_2$. The medium was replaced with 10 ml of CHO—S-SFM medium (manufactured by Invitrogen), and culture was then carried out for 4 to 5 days. Purification of the antigen protein produced in the obtained culture supernatant was carried out using ProteinA SEPHAROSE® HP (manufactured by GE Healthcare). ProteinA SEPHAROSE® HP was sufficiently equilibrated with 20 mM phosphate buffer (pH 7.4)/0.15 M NaCl (equilibration buffer/washing buffer), and a solution prepared by mixing the culture supernatant with the equilibration buffer at a ratio of 1:1 was introduced thereto. Subsequently, the column was washed sufficiently with the washing buffer, and elution was carried out with 0.2 M Glycine buffer (pH 2.5). The eluted solution was neutralized by addition of 1 M Tris (pH 9), and the buffer was exchanged by ultrafiltration using 20 mM phosphate buffer (pH 7.4)/0.15 M NaCl, to prepare the human CD179b protein.

(2) Obtaining Hybridomas

With an equal amount of the MPL+TDM adjuvant (manufactured by Sigma), 100 µg of the antigen protein (human CD179b protein) prepared in (1) was mixed, to prepare an antigen solution for each individual of mouse. The antigen solution was intraperitoneally administered to a Balb/c mouse (Japan SLC, Inc.) of 6 weeks old, and 3 more times of administrations were then carried out at intervals of 1 week, thereby completing immunization. Spleen removed 3 days after the last immunization was placed between 2 sterile slide glasses and ground, followed by repeating 3 times of operations wherein the cells were washed with PBS(−) (manufactured by Nissui Pharmaceutical Co., Ltd.) and centrifuged at 1500 rpm for 10 minutes to remove the supernatant, thereby obtaining spleen cells. The obtained spleen cells and mouse myeloma cells SP2/0 (purchased from ATCC) were mixed together at a ratio of 10:1, and a PEG solution warmed to 37° C. prepared by mixing 200 µl of RPMI1640 medium supplemented with 10% fetal calf serum and 800 µl of PEG1500 (manufactured by Boehringer) together was added to the resulting mixture, followed by leaving the mixture to stand for 5 minutes, thereby carrying out cell fusion. The supernatant was removed by 5 minutes of centrifugation at 1700 rpm, and the cells were suspended in 150 ml of RPMI1640 medium (HAT selection medium) supplemented with 15% fetal calf serum, to which 2% equivalent of HAT solution manufactured by Gibco was added. On each well of 15 96-well plates (manufactured by Nunc), 100 µl of the cell suspension was seeded. The cells were cultured for 7 days under the environment of 37° C., 5% $CO_2$, to obtain hybridomas produced by fusion of the spleen cells and the myeloma cells.

(3) Selection of the Hybridomas

Using as indices the binding affinities, against the human CD179b protein, of the antibodies produced by the prepared hybridomas, hybridomas were selected. In each well of a 96-well plate, 100 µl of 1 µg/ml solution of the human CD179b protein prepared in the above (1) was placed, and the solution was left to stand at 4° C. for 18 hours. Each well was washed with PBS-T 3 times, and 400 µl of 0.5% BSA (Bovine Serum Albumin) solution (manufactured by Sigma) was added to each well, followed by leaving the plate to stand at room temperature for 3 hours. The solution was removed, and the wells were washed 3 times with 400 µl/well of PBS-T, followed by adding 100 µl/well of the culture supernatant of each of the hybridomas obtained in the above (2) and leaving the plate at room temperature for 2 hours. After washing the wells 3 times with PBS-T, 100 µl of an HRP-labeled anti-mouse IgG (H+L) antibody (manufactured by Invitrogen) 5000-fold diluted with PBS was added to each well, and the plate was left to stand at room temperature for 1 hour. The wells were washed 3 times with PBS-T, and 100 µl of TMB substrate solution (manufactured by Thermo) was added to each well, followed by leaving the plate to stand for 15 to 30 minutes to carry out coloring reaction. After allowing coloration, 100 µl of 1 N sulfuric acid was added to each well to stop the reaction, and the absorbance at 450 nm to 595 nm was measured using an absorption spectrometer. As a result, hybridomas producing the antibodies showing the highest absorbance was selected.

The selected hybridomas were placed in a 96-well plate such that each well contains 0.5 cell, and cultured. One week later, hybridomas forming single colonies in the wells were observed. The cells in these wells were further cultured to obtain 60 cloned hybridoma cell lines.

Subsequently, a hybridoma cell line was selected using as indices the binding affinities, against leukemia cells, of the antibodies produced by the above 60 hybridoma cell lines. In each well of a 96-well plate, 100 µl of 1 mg/ml poly-L-lysine (manufactured by Sigma)-PBS solution was placed, and the plate was left to stand at room temperature for 30 minutes. After removing the poly-L-lysine-PBS solution, an operation of filling sterile distilled water in each well and discarding it was repeated 3 times, followed by air-drying of the plate in a clean bench. Namalwa, a human leukemia cell line for which expression of CD179b was confirmed was suspended in PBS(−) such that a cell density of $10^6$ cells/ml was attained, and 100 µl of the resulting suspension was added to each well of the above plate, followed by leaving the plate to stand at room temperature for 15 minutes. After centrifugation at 1700 rpm for 5 minutes, the supernatant was removed, and 100 µl of 0.05% glutaraldehyde (manufactured by Sigma)-PBS solution was added to each well, followed by leaving the plate to stand at room temperature for 10 minutes. Each well was washed with PBS-T 3 times, and 300 µl of 0.5% BSA solution was added to each well, followed by leaving the plate to stand at 4° C. for 18 hours. After washing the wells 3 times with PBS-T, 100 µl of the culture supernatant of each of the 60 hybridoma cell lines obtained as above was added to the well, and the plate was left to stand at room temperature for 2 hours. The supernatant was removed and the wells were washed 3 times with PBS-T, followed by adding 100 µl of an HRP-labeled anti-mouse IgG (H+L) antibody 5000-fold diluted with PBS to each well and leaving the plate to stand at room temperature for 1 hour. The wells were washed 3 times with PBS-T, and 100 µl of TMB substrate solution (manufactured by Thermo) was added to each well, followed by leaving the plate to stand for 30 minutes to carry out coloring reaction. After allowing coloration, 100 µl of 1 N sulfuric acid was added to each well to stop the reaction, and the absorbance at 450 nm to 595 nm was measured using an absorption spectrometer. As a result, the hybridoma cell line #8, which produces the antibody showing the highest absorbance, was selected.

The isotype of the anti-CD179b monoclonal antibody #8 produced by the hybridoma cell strain #8 selected as described above was determined by the ELISA method. The culture supernatant of the hybridoma cell strain #8 was evaluated with the sub-isotyping kit (COSMO BIO Co., Ltd.) according to the protocols described in the attached instructions, and, as a result, the anti-CD179b monoclonal antibody was revealed to be IgG3.

Example 4: The Anti-Tumor Effect of the Anti-CD179b Monoclonal Antibody #8

(1) Preparation of the Anti-CD179b Monoclonal Antibody #8

The hybridoma cell strain #8 was cultured in Hybridoma SFM (manufactured by Invitrogen). The culture fluid was centrifuged at 1500 rpm for 10 minutes, and passed through a filter system 0.22 µm. For purification of the antibody, a Hitrap Protein A Sepharose® FF (manufactured by GE Healthcare) column was used. The column was washed with PBS for equilibration. Subsequently, the culture supernatant was introduced to the column, followed by washing the column with PBS. Elution was carried out with 0.1M Glycine-HCl (pH2.5) to obtain a purified antibody.

The Anti-Tumor Effect In Vitro (on Cells)

The ADCC Activity

Whether or not the anti-CD179b monoclonal antibody #8 can damage tumor cells expressing human CD179b was studied. Human leukemia cells Namalwa, for which expression of human CD179b was confirmed, were collected into a 50 ml centrifuge tube in an amount of $10^6$ cells, and 10 µCi of chromium 51 was added to the tube, followed by incubation at 37° C. for 2 hours. Thereafter, the cells were washed 3 times with RPMI medium supplemented with 10% fetal calf serum, and placed in a 96-well V-bottom plate in an amount of $10^3$ cells/well. To each well, 2 µg of the anti-CD179b monoclonal antibody #8 was added, and $2\times10^5$ lymphocytes separated from mouse spleen were further added thereto, followed by culture under the conditions of 37° C., 5% C02 for 4 hours. Thereafter, the amount of chromium 51 in the culture supernatant released from damaged tumor cells was measured, and the ADCC activity by the anti-CD179b monoclonal antibody #8 against the Namalwa cells was calculated. As a result, an ADCC activity of 60.6% was confirmed for Namalwa in each well. On the other hand, when an isotype control (clone name: ME07) was used in a similar operation, the above activity was not detected. Thus, it was revealed that the anti-CD179 monoclonal antibody #8 can damage tumor cells expressing CD179b by its ADCC activity.

The CDC Activity

Blood collected from a rabbit was placed in an Eppendorf tube, and left to stand at room temperature for 60 minutes, followed by centrifugation at 3000 rpm for 5 minutes to prepare serum for measurement of the CDC activity. Into a 50 ml centrifuge tube, $10^6$ cells of Namalwa, which are human leukemia cells, were collected, and 100 µCi of chromium 51 was added to the tube, followed by incubation at 37° C. for 2 hours and washing the cells 3 times with RPMI medium supplemented with 10% fetal calf serum. Thereafter, the cells were suspended in RPMI medium containing the rabbit serum prepared as described above in an amount of 50%, and placed in a 96-well V-bottom plate in an amount of $10^3$ cells/well. To each well, 2 µg of the anti-CD179b monoclonal antibody #8 was added, followed by culture under the conditions of 37° C., 5% $CO_2$ for 4 hours. Thereafter, the amount of chromium 51 in the culture supernatant released from damaged tumor cells was measured, and the CDC activity by the anti-CD179b monoclonal antibody #8 against the Namalwa cells was calculated. As a result, a CDC activity of 30.5% was confirmed for Namalwa. On the other hand, when an isotype control (clone name: ME07) was used in a similar operation, the above activity was not detected. Thus, it was revealed that the anti-CD179b monoclonal antibody #8 can damage tumor cells expressing CD179b by its CDC activity.

(3) The Anti-Tumor Effect in the Living Body of a Mouse

The anti-tumor activity of the anti-CD179b monoclonal antibody #8 in the living body of a tumor-bearing mouse was evaluated. The antibody used was prepared by purifying the culture supernatant of the hybridoma cell strain #8 by a column in the same manner as described above.

Figure 2:
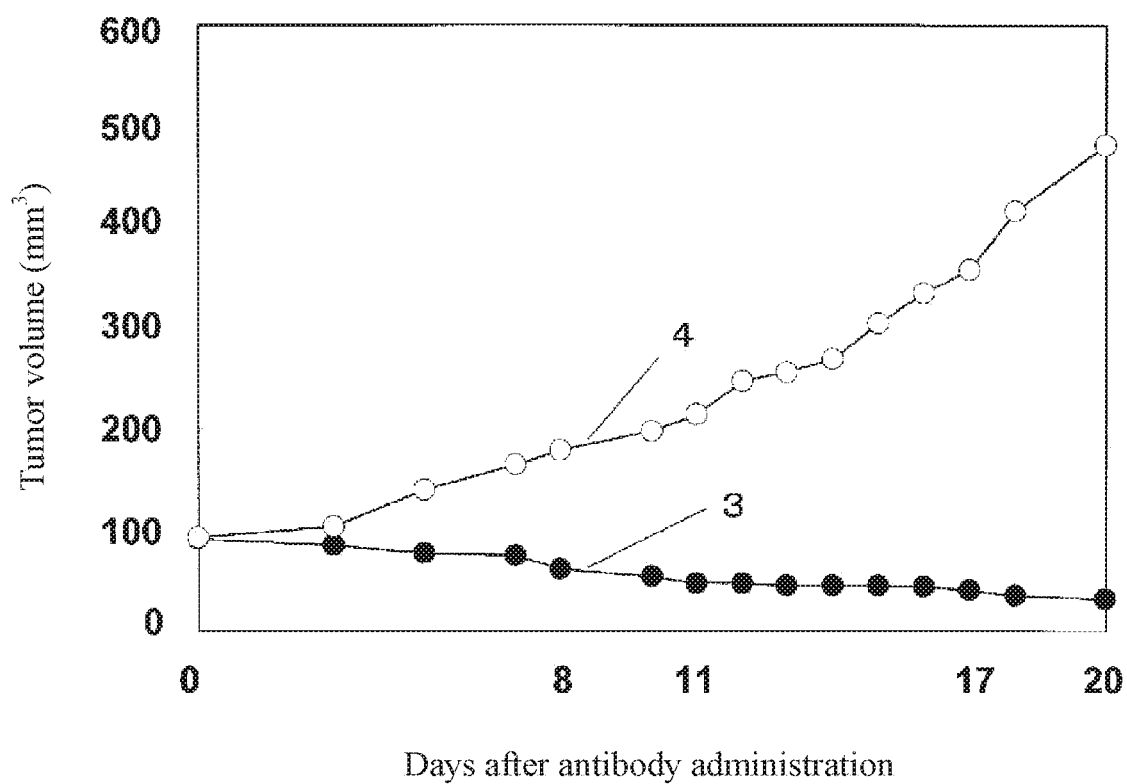
FIG. 2 is a diagram showing an anti-tumor effect of an antibody against CD179b (anti-CD179b monoclonal antibody #8) in nude mice to which a human cancer cell line Namalwa expressing CD179b was transplanted. Reference numeral 3 represents the size of the tumor in mice to which the anti-CD179b monoclonal antibody #8 was administered; and reference numeral 4 represents the size of the tumor in mice to which PBS(-) was administered.

Using a tumor-bearing mouse to which a cancer cell line derived from human which expresses CD179b was transplanted, the anti-tumor activity of the anti-CD179b monoclonal antibody #8 was evaluated. The Namalwa cells were subcutaneously transplanted to the back of each of 20 nude mice (BALB/c Slc-nu/nu, derived from Japan SLC, Inc.) in an amount of $10^6$ cells, and the tumor was allowed to grow to a size of about 7 mm in diameter. Among these mice, each of 10 tumor-bearing mice was subjected to administration of $10^7$ lymphocytes separated from peripheral blood of BALB/c mice (BALB/c Cr Slc, derived from Japan SLC, Inc.) and 300 µg of the anti-CD179b monoclonal antibody #8 from a caudal vein. Thereafter, the same amounts of the mouse lymphocytes and the antibody were administered to each tumor-bearing mouse from a caudal vein a total of 3 times in 2 days, and the size of the tumor was measured every day, thereby evaluating the anti-tumor effect. On the other hand, to each of the remaining 10 tumor-bearing mice, PBS(−) was administered instead of the above antibody, to provide a control group. As a result of this study, in the group wherein the anti-CD179b antibody was administered, the tumor volume reduced to 65% on Day 8 with respect to the tumor volume at the beginning of the administration of the antibody, which was defined as 100%. On Day 11, Day 17 and Day 20, the tumor regressed to 52%, 45% and 35%, respectively (see FIG. 2). On the other hand, in the control group, on Day 8, Day 11, Day 17 and Day 20, the tumor grew to about 180%, 220%, 350% and 420% (see FIG. 2). From these results, it was shown that the obtained anti-CD179b monoclonal antibody #8 exerts a strong anti-tumor effect in the living body, against cancer cells expressing CD179b. In terms of the size of the tumor, the volume was calculated using the calculation equation: longer diameter× shorter diameter×shorter diameter×0.5.

Example 5: Cloning of the Gene for the Variable Region of the Anti-CD179b Monoclonal Antibody #8

From the hybridoma cell line #8, mRNA was extracted, and the genes for the heavy chain variable (VH) region and the light chain variable (VL) region of the anti-CD179b monoclonal antibody #8 were obtained by the RT-PCR method using primers specific to a mouse leader sequence and the antibody constant region of IgG3. For determination of their sequences, these genes were cloned into the pCR2.1 vector (manufactured by Invitrogen).

(1) RT-PCR

From $10^6$ cells of the hybridoma cell strain #8, mRNA was prepared using the mRNA micro purification kit (manufactured by GE Healthcare), and the obtained mRNA was reverse-transcribed to synthesize cDNA using the SuperScript II 1st strand synthesis kit (manufactured by Invitrogen). These operations were carried out according to the protocols described in the attached instructions of the respective kits.

Using the obtained cDNA, the antibody genes were amplified by the PCR method. To obtain the gene for the VH region, a primer specific to the mouse leader sequence (SEQ ID NO:112) and a primer specific to the mouse IgG3 constant region (SEQ ID NO:113) were used. Further, to obtain the gene for the VL region, a primer specific to the mouse leader sequence (SEQ ID NO:114) and a primer specific to the mouse κchain constant region (SEQ ID NO:115) were used. These primers were designed referring to Jones S T and Bending M M Bio/technology 9, 88-89 (1991). For the PCR, Ex Taq (manufactured by TAKARA BIO INC.) was used. To 5 µl of 10×EX Taq Buffer, 4 µl of dNTP Mixture (2.5 mM), 2 µl each of the primers (1.0 µM) and 0.25 µl of Ex Taq (5 units/µl), a cDNA sample was added, and sterile water was added to the resulting mixture to a total volume of 50 µl. The reaction was carried out under the conditions of 2 minutes of treatment at 94° C. followed by 30 cycles of the combination of denaturation at 94° C. for 1 minute, annealing at 58° C. for 30 seconds and the extension reaction at 72° C. for 1 minute.

(2) Cloning

Using each of the PCR products obtained as described above, electrophoresis was carried out with agarose gel, and the DNA band corresponding to each of the VH region and the VL region was excised. Each DNA fragment was processed using the QIAquick Gel purification kit (manufactured by QIAGEN™) according to the protocol described in the attached instructions. Each purified DNA was cloned into the pCR2.1 vector using the TA cloning kit (manufactured by Invitrogen). The vector to which the DNA was linked was used for transformation of DH5a competent cells (manufactured by TOYOBO™) according to a conventional method. Ten clones each of the transformants were cultured in a medium (100 µg/ml ampicillin) at 37° C. overnight, and each plasmid DNA was purified using the Qiaspin Miniprep kit (manufactured by QIAGEN™).

29

(3) Determination of the Sequences

The analysis of the gene sequences of the VH region and the VL region was carried out by analyzing the plasmid DNAs in (2) using the M13 forward primer (SEQ ID NO:116) and the M13 reverse primer (SEQ ID NO:117), by a fluorescent sequencer (DNA sequencer 3130XL manufactured by ABI), using the BIGDYE™ Terminator Ver. 3.1 Cycle Sequencing kit according to the protocol in the attached instructions. As a result, the respective gene sequences were determined (identical among the 10 clones for each gene). The amino acid sequence of the VH region of the anti-CD179b monoclonal antibody #8 is shown in SEQ ID NO:105, and the amino acid sequence of the VL region of the antibody is shown in SEQ ID NO:109.

30

INDUSTRIAL APPLICABILITY

The antibody of the present invention is useful for therapy and/or prophylaxis of cancer.

SEQUENCE LISTING FREE TEXT

SEQ ID NOs:94, 96 to 99: primers
SEQ ID NO:95: T7 primer
SEQ ID NOs:100 and 101: GAPDH primers
SEQ ID NOs:116 and 117: primers

The invention claimed is:

1. A method for therapy of human leukemia expressing CD179b protein comprising administering to a human patient having said leukemia an effective amount of an antibody, said antibody having immunoreactivity to a CD179b protein having the amino acid sequence shown in SEQ ID NO:3, wherein the antibody has an Fc effector domain capable of mediating antibody-dependent cell-mediated cytotoxicity (ADCC) by effector cells and complement-dependent cytotoxicity (CDC) against CD179b-expressing cells sufficient to suppress or regress tumors in a living body, and wherein said leukemia is chronic lymphocyte leukemia, wherein said antibody comprises a heavy chain variable region having the amino acid sequence shown in SEQ ID NO: 105 and a light chain variable region having the amino acid sequence shown in SEQ ID NO: 109.

2. The method according to claim 1, further comprising administering a pharmaceutically acceptable carrier.

3. The method according to claim 1, wherein said antibody is a human antibody, humanized antibody, chimeric antibody, single-chain antibody or bispecific antibody.

4. The method according to claim 1, wherein said antibody is a monoclonal antibody.

5. The method according to claim 1, wherein said antibody is conjugated to a cytotoxic moiety capable of inhibiting the proliferation and/or survival of the leukemia cells.

* * * * *